US010752927B2

(12) United States Patent
Boville et al.

(10) Patent No.: US 10,752,927 B2
(45) Date of Patent: Aug. 25, 2020

(54) METHOD FOR THE SYNTHESIS OF TRYPTOPHAN ANALOGS IN AQUEOUS SOLVENTS AT REDUCED TEMPERATURES

(71) Applicant: California Institute of Technology, Pasadena, CA (US)

(72) Inventors: Christina E. Boville, Pasadena, CA (US); David K. Romney, Pasadena, CA (US); Patrick J. Almhjell, Pasadena, CA (US); Michaela M. Sieben, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 16/290,695

(22) Filed: Mar. 1, 2019

(65) Prior Publication Data

US 2019/0271016 A1 Sep. 5, 2019

Related U.S. Application Data

(60) Provisional application No. 62/637,262, filed on Mar. 1, 2018.

(51) Int. Cl.
*C12P 17/10* (2006.01)
*C12N 9/88* (2006.01)

(52) U.S. Cl.
CPC ........... *C12P 17/10* (2013.01); *C12N 9/88* (2013.01); *C12Y 402/0102* (2013.01)

(58) Field of Classification Search
None
See application file for complete search history.

(56) References Cited

U.S. PATENT DOCUMENTS

| 5,374,543 | A | 12/1994 | Murdock |
| 6,441,274 | B1 | 8/2002 | Cahoon et al. |
| 9,522,947 | B2 | 12/2016 | Kawahata et al. |
| 2011/0183885 | A1 | 7/2011 | Richelson et al. |
| 2016/0298152 | A1 | 10/2016 | Buller et al. |
| 2018/0057806 | A1 | 3/2018 | Romney et al. |
| 2018/0327793 | A1 | 11/2018 | Boville et al. |

FOREIGN PATENT DOCUMENTS

| WO | 1995/034657 A2 | 12/1995 |
| WO | 2018/039495 A1 | 3/2018 |

OTHER PUBLICATIONS

Ahmed, et al. "Aliphatic Alcohols Stabilize an Alternative Conformation of the Tryptophan Synthase $\alpha_2\beta_2$ Complex from *Salmonella typhimurium*," *The Journal of Biological Chemistry*, 269:23, pp. 16486-16492, Jun. 10, 1994.
Boville et al., "Improved Synthesis of 4-Cyanotryptophan and Other Tryptophan Analogues in Aqueous Solvent Using Variants of TrpB From Thermotoga Maritima," *The Journal of Organic Chemistry*, 83(14), pp. 7447-7452, Apr. 13, 2018.
Brzovic, et al. "Substitution of Glutamic Acid 109 by Aspartic Acid Alters the Substrate Specificity and Catalytic Activity of the β-Subunit in the Tryptophan Synthase Bienzyme Complex from *Salmonella typhimurium*," *Biochemistry*, 31, pp. 1180-1190, 1992.
Bucher, "Structural Insights Into the Basis and Evolution of Interactions in Multi-Subunit Protein Assemblies: Tryptophan Synthase and Titin FNIII-Repeats," University of Basel, Doctoral Thesis, Available Online at, <http://edoc.unibas.ch/diss/DissB_8209>, Nov. 20, 2009, 196 pages.
Buller, et al. "Tryptophan Synthase Uses an Atypical Mechanism to Achieve Substrate Specificity," *Biochemistry* 55, 7043-7046, 2016.
Buller, et al. "Directed evolution of the tryptophan synthase β-subunit for stand-alone function recapitulates allosteric activation," *Proc. Natl. Acad. Sci. USA*, 112(47) 14599-14604, 2015.
Evran, et al. "Directed evolution of $(\beta\alpha)_8$-barrel enzymes: establishing phosphoribosylanthranilate isomerization activity on the scaffold of the tryptophan synthase a-subunit," *Protein Engineering, Design & Selection*, 25(6), pp. 285-293, 2012.
Ferrari, et al. "βD305A Mutant of Tryptophan Synthase Shows Strongly Perturbed Allosteric Regulation and Substrate Specificity," *Biochemistry*, 40, pp. 7421-7432, Jun. 1, 2001.
Francis, et al. "An Engineered Tryptophan Synthase Opens New Enzymatic Pathways to b-Methyltryptophan and Derivatives." *ChemBioChem*, 18, 382-386, 2017.
Goss, et al. "A convenient enzymatic synthesis of L-halotryptophans," *Chem Comm*, 47, pp. 4924-4925, 2006.
Herger, et al. "Synthesis of β-Branched Tryptophan Analogues Using an Engineered Subunit of Tryptophan Synthase." *J. Am. Chem. Soc.*, 138, 8388-8391, 2016.
Hilaire et al., "Blue Fluorescent Amino Acid for Biological Spectroscopy and Microscopy", Proceedings of the National Academy of Sciences of the United States of America, 114(23), pp. 6005-6009, May 22, 2017.
Murciano-Calles, et al. "A Panel of TrpB Biocatalysts Derived from Tryptophan Synthase through the Transfer of Mutations that Mimic Allosteric Activation." *Angew. Chem. Int. Ed.*, 55, 11577-11581, 2016.
Murciano-Calles, et al. "Directed Evolution of an Allosteric Tryptophan Synthase to Create a Platform for Synthesis of Noncanonical Amino Acids." In: Alcalde M. (eds) *Directed Enzyme Evolution: Advances and Applications*. Chapter 1, pp. 1-16, Springer-International Publishing AG, 2017.

(Continued)

*Primary Examiner* — Kagnew H Gebreyesus
(74) *Attorney, Agent, or Firm* — Kilpatrick Townsend & Stockton LLP

(57) ABSTRACT

The present disclosure provides methods for preparing tryptophans and tryptophan derivatives. The methods include: combining i) an indole substrate or azulene substrate, ii) a serine substrate, and iii) an engineered tryptophan synthase β-subunit (TrpB); and maintaining the resulting mixture under conditions sufficient to form the product compound. The engineered TrpB comprises a PLP binding loop mutation, a helix 1 mutation, a strand 7-8 mutation, or a combination thereof. New TrpB variants are also described.

13 Claims, 4 Drawing Sheets
Specification includes a Sequence Listing.

(56) References Cited

OTHER PUBLICATIONS

Phillips, et al. "Synthetic applications of tryptophan synthase," *Tetrahedron Asymmetry*, 15(18), pp. 2787-2792, 2004.
Romney, et al. "Unlocking Reactivity of TrpB: A General Biocatalytic Platform for Synthesis of Tryptophan Analogues." *J. Am. Chem. Soc.*, 139, 10769-10776, 2017.
Rowlett, et al., "Mutations in the contact region between the alpha and beta subunits of tryptophan synthase alter subunit interaction and intersubunit communication," *Biochemistry*, 37(9), pp. 2961-2968, 1998.
Smith, et al., "The first one-pot synthesis of L-7-iodotryptophan from 7-iodoindole and serine, and an improved synthesis of other L-7-halotryptophans," *Org. Lett.*, 16(10), pp. 2622-2625, 2014.
Van Wilderen et al., "Cyano-Tryptophans As Dual Infrared and Fluorescence Spectroscopic Labels to Assess Structural Dynamics in Proteins," *Physical Chemistry Chemical Physics*, 20(26), pp. 19906-19915, 2018.
PCT/US2019/020406, "International Search Report and Written Opinion," dated Jul. 29, 2019, 14 pages.

pyridoxal 5'-phosphate amino-acrylate

| variant | 1 | 2 | 3 | 4 | 5 |
|---|---|---|---|---|---|
| Tm2F3 : | 65% | 2.6% | 21% | 34% | 2.3% |
| Tm9D8 : | 71% | 2.5% | 5.3% | 94% | 20% |
| Tm9D8* : | 75% | ND | 7.5% | 92% | 18% |

SEQUENCE LISTING

<160> NUMBER OF SEQ IDS NOS: 30

<210> SEQ ID NO 1
<211> LENGTH: 389
<212> TYPE: PRT
<213> ORGANISM: Thermotoga maritima

<400> SEQUENCE: 1

Met Lys Gly Tyr Phe Gly Pro Tyr Gly Gln Tyr Val Pro Glu Ile
1               5                   10                  15

Leu Met Pro Ala Leu Glu Glu Leu Glu Ala Ala Tyr Glu Glu Ile Met
                20                  25                  30

Lys Asp Glu Ser Phe Trp Lys Glu Phe Asn Asp Leu Leu Arg Asp Tyr
            35                  40                  45

Ala Gly Arg Pro Thr Pro Leu Tyr Phe Ala Arg Leu Ser Glu Lys
        50                  55                  60

Tyr Gly Ala Arg Ile Tyr Leu Lys Arg Glu Asp Leu Leu His Thr Gly
65                  70                  75                  80

Ala His Lys Ile Asn Asn Ala Ile Gly Gln Val Leu Leu Ala Lys Lys

-continued

Met Gly Lys Thr Arg Ile Ile Ala Glu Thr Gly Ala Gly Gln His Gly
            85                  90                  95

Val Ala Thr Ala Thr Ala Ala Leu Phe Gly Met Glu Cys Val Ile
            100                 105                 110

Tyr Met Gly Glu Glu Asp Thr Ile Arg Gln Lys Pro Asn Val Glu Arg
            115                 120                 125

Met Lys Leu Leu Gly Ala Lys Val Val Pro Val Lys Ser Gly Ser Arg
130                 135                 140

Thr Leu Lys Asp Ala Ile Asn Glu Ala Leu Arg Asp Trp Ile Thr Asn
145                 150                 155                 160

Leu Gln Thr Thr Tyr Tyr Val Ile Gly Ser Val Val Gly Pro His Pro
                165                 170                 175

Tyr Pro Ile Ile Val Arg Asn Phe Gln Lys Val Ile Gly Glu Glu Thr
            180                 185                 190

Lys Lys Gln Ile Leu Glu Lys Glu Gly Arg Leu Pro Asp Tyr Ile Val
            195                 200                 205

Ala Cys Val Gly Gly Gly Ser Asn Ala Ala Gly Ile Phe Tyr Pro Phe
225                 210                 215                 220

Ile Asp Ser Gly Val Lys Leu Ile Gly Val Glu Ala Gly Gly Glu Gly
            230                 235                 240

Leu Glu Thr Gly Lys His Ala Ala Ser Leu Leu Lys Gly Lys Ile Gly
            245                 250                 255

Tyr Leu His Gly Ser Lys Thr Phe Val Leu Gln Asp Asp Trp Gly Gln
            260                 265                 270

Val Gln Val Thr His Ser Val Ser Ala Gly Leu Asp Tyr Ser Gly Val
275                 280                 285

Gly Pro Glu His Ala Tyr Trp Arg Glu Thr Gly Lys Val Leu Tyr Asp
            290                 295                 300

Ala Val Thr Asp Glu Glu Ala Leu Asp Ala Phe Ile Glu Leu Ser Arg
305                 310                 315                 320

Leu Glu Gly Ile Ile Pro Ala Leu Glu Ser Ser His Ala Leu Ala Tyr
            325                 330                 335

Leu Lys Lys Ile Asn Ile Lys Gly Lys Val Val Val Asn Leu Ser
            340                 345                 350

Gly Arg Gly Asp Lys Asp Leu Glu Ser Val Leu Asn His Pro Tyr Val
            355                 360                 365

Arg Glu Arg Ile Arg
            370                 375                 380
385

<210> SEQ ID NO 2
<211> LENGTH: 388
<212> TYPE: PRT
<213> ORGANISM: Pyrococcus furiosus

<400> SEQUENCE: 2

Met Trp Phe Gly Glu Phe Gly Gly Gln Tyr Val Pro Glu Thr Leu Ile
1               5                   10                  15

Glu Pro Leu Lys Glu Leu Glu Lys Ala Tyr Lys Arg Phe Lys Asp Asp
            20                  25                  30

Glu Glu Phe Asn Arg Gln Leu Asn Tyr Tyr Leu Lys Thr Trp Ala Gly
            35                  40                  45

Arg Pro Thr Pro Leu Tyr Tyr Ala Lys Arg Leu Thr Glu Lys Ile Gly
        50                  55                  60

```
Gly Ala Lys Ile Tyr Leu Lys Arg Glu Asp Leu Val His Gly Gly Ala
 65                  70                  75                  80

His Lys Thr Asn Asn Ala Ile Gly Gln Ala Leu Leu Ala Lys Phe Met
                 85                  90                  95

Gly Lys Thr Arg Leu Ile Ala Glu Thr Gly Ala Gly Gln His Gly Val
            100                 105                 110

Ala Thr Ala Met Ala Gly Ala Leu Leu Gly Met Lys Val Asp Ile Tyr
        115                 120                 125

Met Gly Ala Glu Asp Val Glu Arg Gln Lys Met Asn Val Phe Arg Met
    130                 135                 140

Lys Leu Leu Gly Ala Asn Val Ile Pro Val Asn Ser Gly Ser Arg Thr
145                 150                 155                 160

Leu Lys Asp Ala Ile Asn Glu Ala Leu Arg Asp Trp Val Ala Thr Phe
                165                 170                 175

Glu Tyr Thr His Tyr Leu Ile Gly Ser Val Val Gly Pro His Pro Tyr
            180                 185                 190

Pro Thr Ile Val Arg Asp Phe Gln Ser Val Ile Gly Arg Glu Ala Lys
        195                 200                 205

Ala Gln Ile Leu Glu Ala Glu Gly Gln Leu Pro Asp Val Ile Val Ala
    210                 215                 220

Cys Val Gly Gly Gly Ser Asn Ala Met Gly Ile Phe Tyr Pro Phe Val
225                 230                 235                 240

Asn Asp Lys Lys Val Lys Leu Val Gly Val Glu Ala Gly Gly Lys Gly
                245                 250                 255

Leu Glu Ser Gly Lys His Ser Ala Ser Leu Asn Ala Gly Gln Val Gly
            260                 265                 270

Val Phe His Gly Met Leu Ser Tyr Phe Leu Gln Asp Glu Glu Gly Gln
        275                 280                 285

Ile Lys Pro Thr His Ser Ile Ala Pro Gly Leu Asp Tyr Pro Gly Val
    290                 295                 300

Gly Pro Glu His Ala Tyr Leu Lys Lys Ile Gln Arg Ala Glu Tyr Val
305                 310                 315                 320

Thr Val Thr Asp Glu Glu Ala Leu Lys Ala Phe His Glu Leu Ser Arg
                325                 330                 335

Thr Glu Gly Ile Ile Pro Ala Leu Glu Ser Ala His Ala Val Ala Tyr
            340                 345                 350

Ala Met Lys Leu Ala Lys Glu Met Ser Arg Asp Glu Ile Ile Ile Val
        355                 360                 365

Asn Leu Ser Gly Arg Gly Asp Lys Asp Leu Asp Ile Val Leu Lys Val
    370                 375                 380

Ser Gly Asn Val
385

<210> SEQ ID NO 3
<211> LENGTH: 389
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Lys Gly Tyr Phe Gly Pro Tyr Gly Gly Gln Tyr Val Pro Glu Ile
1               5                   10                  15

Leu Met Gly Ala Leu Glu Glu Leu Glu Ala Ala Tyr Glu Gly Ile Met
            20                  25                  30
```

Lys Asp Glu Ser Phe Trp Lys Glu Phe Asn Asp Leu Leu Arg Asp Tyr
            35                  40                  45

Ala Gly Arg Pro Thr Pro Leu Tyr Phe Ala Arg Arg Leu Ser Glu Lys
 50                  55                  60

Tyr Gly Ala Arg Val Tyr Leu Lys Arg Glu Asp Leu Leu His Thr Gly
 65                  70                  75                  80

Ala His Lys Ile Asn Asn Ala Ile Gly Gln Val Leu Leu Ala Lys Leu
                 85                  90                  95

Met Gly Lys Thr Arg Ile Ile Ala Glu Thr Gly Ala Gly Gln His Gly
            100                 105                 110

Val Ala Thr Ala Thr Ala Ala Leu Phe Gly Met Glu Cys Val Ile
        115                 120                 125

Tyr Met Gly Glu Glu Asp Thr Ile Arg Gln Lys Leu Asn Val Glu Arg
    130                 135                 140

Met Lys Leu Leu Gly Ala Lys Val Val Pro Val Lys Ser Gly Ser Arg
145                 150                 155                 160

Thr Leu Lys Asp Ala Ile Asp Glu Ala Leu Arg Asp Trp Ile Thr Asn
                165                 170                 175

Leu Gln Thr Thr Tyr Tyr Val Ile Gly Ser Val Val Gly Pro His Pro
            180                 185                 190

Tyr Pro Ile Ile Val Arg Asn Phe Gln Lys Val Ile Gly Glu Glu Thr
        195                 200                 205

Lys Lys Gln Ile Pro Glu Lys Glu Gly Arg Leu Pro Asp Tyr Ile Val
    210                 215                 220

Ala Cys Val Ser Gly Gly Ser Asn Ala Ala Gly Ile Phe Tyr Pro Phe
225                 230                 235                 240

Ile Asp Ser Gly Val Lys Leu Ile Gly Val Glu Ala Gly Gly Glu Gly
                245                 250                 255

Leu Glu Thr Gly Lys His Ala Ala Ser Leu Leu Lys Gly Lys Ile Gly
            260                 265                 270

Tyr Leu His Gly Ser Lys Thr Phe Val Leu Gln Asp Asp Trp Gly Gln
        275                 280                 285

Val Gln Val Ser His Ser Val Ser Ala Gly Leu Asp Tyr Ser Gly Val
    290                 295                 300

Gly Pro Glu His Ala Tyr Trp Arg Glu Thr Gly Lys Val Leu Tyr Asp
305                 310                 315                 320

Ala Val Thr Asp Glu Glu Ala Leu Asp Ala Phe Ile Glu Leu Ser Arg
                325                 330                 335

Leu Glu Gly Ile Ile Pro Ala Leu Glu Ser Ser His Ala Leu Ala Tyr
            340                 345                 350

Leu Lys Lys Ile Asn Ile Lys Gly Lys Val Val Val Asn Leu Ser
        355                 360                 365

Gly Arg Gly Asp Lys Asp Leu Glu Ser Val Leu Asn His Pro Tyr Val
370                 375                 380

Arg Glu Arg Ile Arg
385

<210> SEQ ID NO 4
<211> LENGTH: 389
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Met Lys Gly Tyr Phe Gly Pro Tyr Gly Gln Tyr Val Pro Glu Ile
1               5                   10                  15

Leu Met Gly Ala Leu Glu Glu Leu Glu Ala Ala Tyr Glu Gly Ile Met
            20                  25                  30

Lys Asp Glu Ser Phe Trp Lys Glu Phe Asn Asp Leu Leu Arg Asp Tyr
                35                  40                  45

Ala Gly Arg Pro Thr Pro Leu Tyr Phe Ala Arg Arg Leu Ser Glu Lys
50                  55                      60

Tyr Gly Ala Arg Val Tyr Leu Lys Arg Glu Asp Leu Leu His Thr Gly
65                  70                  75                  80

Ala His Lys Ile Asn Asn Ala Ile Gly Gln Val Leu Leu Ala Lys Leu
                85                  90                  95

Met Gly Lys Thr Arg Ile Ile Ala Glu Thr Gly Ala Gly Gln His Gly
                100                 105                 110

Val Ala Thr Ala Thr Ala Ala Ala Leu Phe Gly Met Glu Cys Val Ile
                115                 120                 125

Tyr Met Gly Glu Glu Asp Thr Ile Arg Gln Lys Leu Asn Val Glu Arg
130                 135                     140

Met Lys Leu Leu Gly Ala Lys Val Val Pro Val Lys Ser Gly Ser Arg
145                 150                 155                 160

Thr Leu Lys Asp Ala Ile Asp Glu Ala Leu Arg Asp Trp Ile Thr Asn
                165                 170                 175

Leu Gln Thr Thr Tyr Tyr Val Phe Gly Ser Val Val Gly Pro His Pro
                180                 185                 190

Tyr Pro Ile Ile Val Arg Asn Phe Gln Lys Val Ile Gly Glu Glu Thr
                195                 200                 205

Lys Lys Gln Ile Pro Glu Lys Glu Gly Arg Leu Pro Asp Tyr Ile Val
210                 215                     220

Ala Cys Val Ser Gly Gly Ser Asn Ala Ala Gly Ile Phe Tyr Pro Phe
225                 230                 235                 240

Ile Asp Ser Gly Val Lys Leu Ile Gly Val Glu Ala Gly Gly Glu Gly
                245                 250                 255

Leu Glu Thr Gly Lys His Ala Ala Ser Leu Leu Lys Gly Lys Ile Gly
                260                 265                 270

Tyr Leu His Gly Ser Lys Thr Phe Val Leu Gln Asp Asp Trp Gly Gln
                275                 280                 285

Val Gln Val Ser His Ser Val Ser Ala Gly Leu Asp Tyr Ser Gly Val
290                 295                     300

Gly Pro Glu His Ala Tyr Trp Arg Glu Thr Gly Lys Val Leu Tyr Asp
305                 310                 315                 320

Ala Val Thr Asp Glu Glu Ala Leu Asp Ala Phe Ile Glu Leu Ser Arg
                325                 330                 335

Leu Glu Gly Ile Ile Pro Ala Leu Glu Ser Ser His Ala Leu Ala Tyr
                340                 345                 350

Leu Lys Lys Ile Asn Ile Lys Gly Lys Val Val Val Asn Leu Ser
                355                 360                 365

Gly Arg Gly Asp Lys Asp Leu Glu Ser Val Leu Asn His Pro Tyr Val
370                 375                     380

Arg Glu Arg Ile Arg
385
```

<210> SEQ ID NO 5

<211> LENGTH: 397
<212> TYPE: PRT
<213> ORGANISM: Archaeoglobus fulgidus

<400> SEQUENCE: 5

```
Met Arg Cys Trp Leu Glu Asn Leu Ser Gly Gly Arg Lys Met Lys Phe
1               5                   10                  15

Gly Glu Phe Gly Gly Arg Phe Val Pro Glu Val Leu Ile Pro Pro Leu
            20                  25                  30

Glu Glu Leu Glu Lys Ala Tyr Asp Arg Phe Lys Asp Glu Glu Phe
        35                  40                  45

Lys Ala Arg Leu Glu Tyr Tyr Leu Lys Ser Tyr Ala Gly Arg Pro Thr
50                  55                  60

Pro Leu Tyr Phe Ala Glu Asn Leu Ser Arg Glu Leu Gly Val Lys Ile
65                  70                  75                  80

Tyr Leu Lys Arg Glu Asp Leu Leu His Gly Ala His Lys Ile Asn
                85                  90                  95

Asn Thr Ile Gly Gln Ala Leu Leu Ala Lys Phe Met Gly Lys Lys Arg
            100                 105                 110

Val Ile Ala Glu Thr Gly Ala Gly Gln His Gly Val Ala Thr Ala Met
        115                 120                 125

Ala Ala Ala Leu Leu Gly Leu Glu Ala Glu Ile Tyr Met Gly Ala Glu
130                 135                 140

Asp Tyr Glu Arg Gln Lys Met Asn Val Phe Arg Met Glu Leu Leu Gly
145                 150                 155                 160

Ala Lys Val Thr Ala Val Glu Ser Gly Ser Arg Thr Leu Lys Asp Ala
                165                 170                 175

Ile Asn Glu Ala Leu Arg Asp Trp Val Glu Ser Phe Glu His Thr His
            180                 185                 190

Tyr Leu Ile Gly Ser Val Val Gly Pro His Pro Phe Pro Thr Ile Val
        195                 200                 205

Arg Asp Phe Gln Ala Val Ile Gly Lys Glu Ala Arg Arg Gln Ile Ile
210                 215                 220

Glu Ala Glu Gly Gly Met Pro Asp Ala Ile Ile Ala Cys Val Gly Gly
225                 230                 235                 240

Gly Ser Asn Ala Met Gly Ile Phe His Pro Phe Leu Asn Asp Asp Val
                245                 250                 255

Arg Leu Ile Gly Val Glu Ala Gly Gly Glu Gly Ile Glu Ser Gly Arg
            260                 265                 270

His Ser Ala Ser Leu Thr Ala Gly Ser Lys Gly Val Leu His Gly Met
        275                 280                 285

Leu Ser Tyr Phe Leu Gln Asp Glu Glu Gly Met Met Leu Asp Thr His
290                 295                 300

Ser Val Ser Ala Gly Leu Asp Tyr Pro Gly Val Gly Pro Glu His Ala
305                 310                 315                 320

Tyr Leu Lys Glu Thr Gly Arg Cys Glu Tyr Val Thr Val Asn Asp Glu
                325                 330                 335

Glu Ala Leu Arg Ala Phe Lys Thr Leu Ser Lys Leu Glu Gly Ile Ile
            340                 345                 350

Pro Ala Leu Glu Ser Ala His Ala Ile Ala Tyr Ala Met Lys Met Ala
        355                 360                 365

Glu Glu Met Gln Arg Asp Asp Val Leu Val Val Asn Leu Ser Gly Arg
370                 375                 380

Gly Asp Lys Asp Met Asp Ile Val Arg Arg Arg Leu Ala
```

```
385             390             395
```

<210> SEQ ID NO 6
<211> LENGTH: 397
<212> TYPE: PRT
<213> ORGANISM: Escherichia coli

<400> SEQUENCE: 6

```
Met Thr Thr Leu Leu Asn Pro Tyr Phe Gly Glu Phe Gly Met Tyr
 1               5                  10                  15

Val Pro Gln Ile Leu Met Pro Ala Leu Arg Gln Leu Glu Glu Ala Phe
                20                  25                  30

Val Ser Ala Gln Lys Asp Pro Glu Phe Gln Ala Gln Phe Asn Asp Leu
            35                  40                  45

Leu Lys Asn Tyr Ala Gly Arg Pro Thr Ala Leu Thr Lys Cys Gln Asn
        50                  55                  60

Ile Thr Ala Gly Thr Asn Thr Thr Leu Tyr Leu Lys Arg Glu Asp Leu
65                  70                  75                  80

Leu His Gly Gly Ala His Lys Thr Asn Gln Val Leu Gly Gln Ala Leu
                85                  90                  95

Leu Ala Lys Arg Met Gly Lys Thr Glu Ile Ile Ala Glu Thr Gly Ala
            100                 105                 110

Gly Gln His Gly Val Ala Ser Ala Leu Ala Ser Ala Leu Leu Gly Leu
        115                 120                 125

Lys Cys Arg Ile Tyr Met Gly Ala Lys Asp Val Glu Arg Gln Ser Pro
130                 135                 140

Asn Val Phe Arg Met Arg Leu Met Gly Ala Glu Val Ile Pro Val His
145                 150                 155                 160

Ser Gly Ser Ala Thr Leu Lys Asp Ala Cys Asn Glu Ala Leu Arg Asp
                165                 170                 175

Trp Ser Gly Ser Tyr Glu Thr Ala His Tyr Met Leu Gly Thr Ala Ala
            180                 185                 190

Gly Pro His Pro Tyr Pro Thr Ile Val Arg Glu Phe Gln Arg Met Ile
        195                 200                 205

Gly Glu Glu Thr Lys Ala Gln Ile Leu Glu Arg Glu Gly Arg Leu Pro
210                 215                 220

Asp Ala Val Ile Ala Cys Val Gly Gly Gly Ser Asn Ala Ile Gly Met
225                 230                 235                 240

Phe Ala Asp Phe Ile Asn Glu Thr Asn Val Gly Leu Ile Gly Val Glu
                245                 250                 255

Pro Gly Gly His Gly Ile Glu Thr Gly Glu His Gly Ala Pro Leu Lys
            260                 265                 270

His Gly Arg Val Gly Ile Tyr Phe Gly Met Lys Ala Pro Met Met Gln
        275                 280                 285

Thr Glu Asp Gly Gln Ile Glu Glu Ser Tyr Ser Ile Ser Ala Gly Leu
290                 295                 300

Asp Phe Pro Ser Val Gly Pro Gln His Ala Tyr Leu Asn Ser Thr Gly
305                 310                 315                 320

Arg Ala Asp Tyr Val Ser Ile Thr Asp Asp Glu Ala Leu Glu Ala Phe
                325                 330                 335

Lys Thr Leu Cys Leu His Glu Gly Ile Ile Pro Ala Leu Glu Ser Ser
            340                 345                 350

His Ala Leu Ala His Ala Leu Lys Met Met Arg Glu Asn Pro Asp Lys
        355                 360                 365
```

Glu Gln Leu Leu Val Val Asn Leu Ser Gly Arg Gly Asp Lys Asp Ile
370                 375                 380

Phe Thr Val His Asp Ile Leu Lys Ala Arg Gly Glu Ile
385                 390                 395

<210> SEQ ID NO 7
<211> LENGTH: 397
<212> TYPE: PRT
<213> ORGANISM: Salmonella typhimurium

<400> SEQUENCE: 7

Met Thr Thr Leu Leu Asn Pro Tyr Phe Gly Glu Phe Gly Gly Met Tyr
1               5                   10                  15

Val Pro Gln Ile Leu Met Pro Ala Leu Asn Gln Leu Glu Glu Ala Phe
            20                  25                  30

Val Ser Ala Gln Lys Asp Pro Glu Phe Gln Ala Gln Phe Ala Asp Leu
        35                  40                  45

Leu Lys Asn Tyr Ala Gly Arg Pro Thr Ala Leu Thr Lys Cys Gln Asn
    50                  55                  60

Ile Thr Ala Gly Thr Arg Thr Thr Leu Tyr Leu Lys Arg Glu Asp Leu
65                  70                  75                  80

Leu His Gly Gly Ala His Lys Thr Asn Gln Val Leu Gly Gln Ala Leu
                85                  90                  95

Leu Ala Lys Arg Met Gly Lys Ser Glu Ile Ile Ala Glu Thr Gly Ala
            100                 105                 110

Gly Gln His Gly Val Ala Ser Ala Leu Ala Ser Ala Leu Leu Gly Leu
        115                 120                 125

Lys Cys Arg Ile Tyr Met Gly Ala Lys Asp Val Glu Arg Gln Ser Pro
    130                 135                 140

Asn Val Phe Arg Met Arg Leu Met Gly Ala Glu Val Ile Pro Val His
145                 150                 155                 160

Ser Gly Ser Ala Thr Leu Lys Asp Ala Cys Asn Glu Ala Leu Arg Asp
                165                 170                 175

Trp Ser Gly Ser Tyr Glu Thr Ala His Tyr Met Leu Gly Thr Ala Ala
            180                 185                 190

Gly Pro His Pro Tyr Pro Thr Ile Val Arg Glu Phe Gln Arg Met Ile
        195                 200                 205

Gly Glu Glu Thr Lys Ala Gln Ile Leu Asp Lys Glu Gly Arg Leu Pro
    210                 215                 220

Asp Ala Val Ile Ala Cys Val Gly Gly Gly Ser Asn Ala Ile Gly Met
225                 230                 235                 240

Phe Ala Asp Phe Ile Asn Asp Thr Ser Val Gly Leu Ile Gly Val Glu
                245                 250                 255

Pro Gly Gly His Gly Ile Glu Thr Gly Glu His Gly Ala Pro Leu Lys
            260                 265                 270

His Gly Arg Val Gly Ile Tyr Phe Gly Met Lys Ala Pro Met Met Gln
        275                 280                 285

Thr Ala Asp Gly Gln Ile Glu Glu Ser Tyr Ser Ile Ser Ala Gly Leu
    290                 295                 300

Asp Phe Pro Ser Val Gly Pro Gln His Ala Tyr Leu Asn Ser Ile Gly
305                 310                 315                 320

Arg Ala Asp Tyr Val Ser Ile Thr Asp Asp Glu Ala Leu Glu Ala Phe
                325                 330                 335

Lys Thr Leu Cys Arg His Glu Gly Ile Ile Pro Ala Leu Glu Ser Ser
            340                 345                 350

His Ala Leu Ala His Ala Leu Lys Met Met Arg Glu Gln Pro Glu Lys
          355                 360                 365

Glu Gln Leu Leu Val Val Asn Leu Ser Gly Arg Gly Asp Lys Asp Ile
370                 375                 380

Phe Thr Val His Asp Ile Leu Lys Ala Arg Gly Glu Ile
385                 390                 395

<210> SEQ ID NO 8
<211> LENGTH: 389
<212> TYPE: PRT
<213> ORGANISM: Thermotoga naphthophila

<400> SEQUENCE: 8

Met Lys Gly Tyr Phe Gly Pro Tyr Gly Gly Gln Tyr Val Pro Glu Ile
1               5                   10                  15

Leu Met Pro Ala Leu Glu Glu Leu Glu Ala Ala Tyr Glu Gly Ile Met
            20                  25                  30

Lys Asp Gly Ser Phe Trp Arg Glu Phe Asn Asp Leu Leu Arg Asp Tyr
        35                  40                  45

Ala Gly Arg Pro Thr Pro Leu Tyr Phe Ala Arg Leu Ser Glu Lys
    50                  55                  60

Tyr Asn Ala Arg Ile Tyr Leu Lys Arg Glu Asp Leu Leu His Thr Gly
65                  70                  75                  80

Ala His Lys Ile Asn Asn Ala Ile Gly Gln Val Leu Leu Ala Lys Arg
                85                  90                  95

Met Gly Lys Thr Arg Ile Ile Ala Glu Thr Gly Ala Gly Gln His Gly
            100                 105                 110

Val Ala Thr Ala Thr Ala Ala Ala Leu Phe Gly Met Glu Cys Val Ile
        115                 120                 125

Tyr Met Gly Glu Glu Asp Thr Ile Arg Gln Lys Pro Asn Val Glu Arg
130                 135                 140

Met Lys Leu Leu Gly Ala Lys Val Val Pro Val Lys Ser Gly Ser Arg
145                 150                 155                 160

Thr Leu Lys Asp Ala Ile Asn Glu Ala Leu Arg Asp Trp Ile Thr Asn
                165                 170                 175

Leu Gln Thr Thr Tyr Tyr Val Ile Gly Ser Val Val Gly Pro His Pro
            180                 185                 190

Tyr Pro Ile Ile Val Arg Asn Phe Gln Lys Val Ile Gly Glu Glu Thr
        195                 200                 205

Lys Lys Gln Ile Leu Glu Lys Glu Gly Arg Leu Pro Asp Tyr Ile Val
    210                 215                 220

Ala Cys Val Gly Gly Gly Ser Asn Ala Ala Gly Ile Phe Tyr Pro Phe
225                 230                 235                 240

Ile Asp Ser Gly Val Lys Leu Ile Gly Val Glu Ala Gly Gly Glu Gly
                245                 250                 255

Leu Glu Thr Gly Lys His Ala Ala Ser Leu Leu Lys Gly Lys Ile Gly
            260                 265                 270

Tyr Leu His Gly Ser Lys Thr Phe Val Leu Gln Asp Asp Trp Gly Gln
        275                 280                 285

Val Gln Val Thr His Ser Val Ser Ala Gly Leu Asp Tyr Ser Gly Val
    290                 295                 300

Gly Pro Glu His Ala Tyr Trp Arg Glu Thr Gly Lys Val Leu Tyr Asp
305                 310                 315                 320

Ala Val Thr Asp Glu Glu Ala Leu Asp Ala Phe Ile Glu Leu Ser Arg

```
            325                 330                 335
Leu Glu Gly Ile Ile Pro Ala Leu Glu Ser Ser His Ala Leu Ala Tyr
            340                 345                 350

Leu Lys Lys Ile Asn Ile Lys Gly Lys Val Val Val Asn Leu Ser
            355                 360                 365

Gly Arg Gly Asp Lys Asp Leu Glu Ser Val Leu Asn His Pro Tyr Val
    370                 375                 380

Arg Glu Arg Ile Gly
385

<210> SEQ ID NO 9
<211> LENGTH: 389
<212> TYPE: PRT
<213> ORGANISM: Thermotoga petrophila

<400> SEQUENCE: 9

Met Lys Gly Tyr Phe Gly Pro Tyr Gly Gly Gln Tyr Val Pro Glu Ile
1               5                   10                  15

Leu Met Pro Ala Leu Glu Glu Leu Glu Ala Ala Tyr Glu Gly Ile Met
            20                  25                  30

Lys Asp Gly Ser Phe Trp Arg Glu Phe Asn Asp Leu Leu Arg Asp Tyr
        35                  40                  45

Ala Gly Arg Pro Thr Pro Leu Tyr Phe Ala Arg Arg Leu Ser Glu Lys
    50                  55                  60

Tyr Asn Ala Arg Ile Tyr Leu Lys Arg Glu Asp Leu Leu His Thr Gly
65                  70                  75                  80

Ala His Lys Ile Asn Asn Ala Ile Gly Gln Val Leu Leu Ala Lys Arg
                85                  90                  95

Met Gly Lys Thr Arg Ile Ile Ala Glu Thr Gly Ala Gly Gln His Gly
            100                 105                 110

Val Ala Thr Ala Thr Ala Ala Ala Leu Phe Gly Met Glu Cys Val Ile
        115                 120                 125

Tyr Met Gly Glu Glu Asp Thr Ile Arg Gln Lys Pro Asn Val Glu Arg
130                 135                 140

Met Lys Leu Leu Gly Ala Lys Val Val Pro Val Lys Ser Gly Ser Arg
145                 150                 155                 160

Thr Leu Lys Asp Ala Ile Asn Glu Ala Leu Arg Asp Trp Ile Thr Asn
                165                 170                 175

Leu Gln Thr Thr Tyr Tyr Val Ile Gly Ser Val Val Gly Pro His Pro
            180                 185                 190

Tyr Pro Ile Ile Val Arg Asn Phe Gln Lys Val Ile Gly Glu Glu Thr
        195                 200                 205

Lys Lys Gln Ile Leu Glu Lys Glu Gly Arg Leu Pro Asp Tyr Ile Val
    210                 215                 220

Ala Cys Val Gly Gly Gly Ser Asn Ala Ala Gly Ile Phe Tyr Pro Phe
225                 230                 235                 240

Ile Asp Ser Gly Val Lys Leu Ile Gly Val Glu Ala Gly Gly Glu Gly
                245                 250                 255

Leu Glu Thr Gly Lys His Ala Ala Ser Leu Leu Lys Gly Lys Ile Gly
            260                 265                 270

Tyr Leu His Gly Ser Lys Thr Phe Val Leu Gln Asp Asp Trp Gly Gln
        275                 280                 285

Val Gln Val Thr His Ser Val Ser Ala Gly Leu Asp Tyr Ser Gly Val
    290                 295                 300
```

```
Gly Pro Glu His Ala Tyr Trp Arg Glu Thr Gly Lys Val Leu Tyr Asp
305                 310                 315                 320

Ala Val Thr Asp Glu Glu Ala Leu Asp Ala Phe Ile Glu Leu Ser Arg
            325                 330                 335

Leu Glu Gly Ile Ile Pro Ala Leu Glu Ser Ser His Ala Leu Ala Tyr
        340                 345                 350

Leu Lys Lys Ile Asn Ile Lys Gly Lys Val Val Val Asn Leu Ser
    355                 360                 365

Gly Arg Gly Asp Lys Asp Leu Glu Ser Val Leu Asn His Pro Tyr Val
370                 375                 380

Arg Glu Arg Ile Gly
385
```

<210> SEQ ID NO 10
<211> LENGTH: 389
<212> TYPE: PRT
<213> ORGANISM: Thermotoga neapolitana

<400> SEQUENCE: 10

```
Met Lys Gly Tyr Phe Gly Pro Tyr Gly Gly Gln Tyr Val Pro Glu Ile
1               5                   10                  15

Leu Met Pro Ala Leu Glu Glu Leu Glu Glu Ala Tyr Glu Ser Ile Thr
            20                  25                  30

Lys Asp Glu Ser Phe Trp Glu Glu Phe Asn Arg Leu Leu Met Asp Tyr
        35                  40                  45

Ala Gly Arg Pro Thr Pro Leu Tyr Phe Ala Glu Arg Leu Ser Lys Lys
    50                  55                  60

Tyr Gly Ala Lys Ile Tyr Leu Lys Arg Glu Asp Leu Leu His Thr Gly
65                  70                  75                  80

Ala His Lys Ile Asn Asn Ala Leu Gly Gln Val Leu Leu Ala Lys Arg
                85                  90                  95

Met Gly Lys Thr Arg Ile Ile Ala Glu Thr Gly Ala Gly Gln His Gly
            100                 105                 110

Val Ala Thr Ala Thr Ala Ala Ala Leu Phe Gly Met Glu Cys Val Ile
        115                 120                 125

Tyr Met Gly Glu Glu Asp Thr Ile Arg Gln Lys Pro Asn Val Glu Arg
130                 135                 140

Met Lys Leu Leu Gly Ala Lys Val Val Pro Val Lys Ser Gly Ser Arg
145                 150                 155                 160

Thr Leu Lys Asp Ala Ile Asn Glu Ala Leu Arg Asp Trp Ile Thr Asn
                165                 170                 175

Leu Gln Thr Thr Tyr Tyr Val Ile Gly Ser Val Val Gly Pro His Pro
            180                 185                 190

Tyr Pro Ile Ile Val Arg Asn Phe Gln Lys Val Ile Gly Glu Glu Thr
        195                 200                 205

Lys Arg Gln Ile Leu Glu Lys Glu Gly Lys Leu Pro Asp Tyr Ile Leu
    210                 215                 220

Ala Cys Val Gly Gly Gly Ser Asn Ala Ala Gly Ile Phe Tyr Pro Phe
225                 230                 235                 240

Ile Asp Ser Gly Val Lys Leu Ile Gly Ile Glu Ala Gly Gly Glu Gly
                245                 250                 255

Leu Asn Thr Gly Lys His Ala Ala Ser Leu Leu Lys Gly Lys Val Gly
            260                 265                 270

Tyr Leu His Gly Ser Lys Thr Leu Val Leu Gln Asp Glu Trp Gly Gln
        275                 280                 285
```

Val Gln Ile Thr His Ser Val Ser Ala Gly Leu Asp Tyr Ser Gly Val
            290                 295                 300

Gly Pro Glu His Ala Tyr Trp Lys Glu Thr Gly Lys Val Phe Tyr Asp
305                 310                 315                 320

Ala Val Thr Asp Glu Glu Ala Leu Asp Ala Phe Leu Glu Leu Ser Arg
                325                 330                 335

Leu Glu Gly Ile Ile Pro Ala Leu Glu Ser Ser His Ala Leu Ala Tyr
            340                 345                 350

Leu Arg Lys Ile Asp Ile Arg Gly Lys Thr Val Ile Val Asn Leu Ser
            355                 360                 365

Gly Arg Gly Asp Lys Asp Leu Glu Ser Val Leu Asn His Pro Tyr Ile
            370                 375                 380

Arg Glu Arg Ile Gly
385

<210> SEQ ID NO 11
<211> LENGTH: 391
<212> TYPE: PRT
<213> ORGANISM: Caldanaerobacter subterraneus

<400> SEQUENCE: 11

Met Lys Gly Arg Phe Gly Arg Phe Gly Gly Gln Tyr Val Pro Glu Thr
1               5                   10                  15

Val Met Asn Ala Leu Ile Glu Leu Glu Arg Glu Phe Glu Glu Ala Lys
            20                  25                  30

Lys Asp Glu Lys Phe Met Glu Glu Tyr Arg Tyr Tyr Leu Lys Glu Tyr
        35                  40                  45

Ser Gly Arg Pro Thr Pro Leu Tyr Tyr Ala Glu Asn Leu Thr Lys Arg
    50                  55                  60

Leu Gly Gly Ala Lys Ile Tyr Leu Lys Arg Glu Asp Leu Asn His Thr
65                  70                  75                  80

Gly Ala His Lys Ile Asn Asn Val Leu Gly Gln Val Leu Leu Ala Lys
                85                  90                  95

Arg Met Gly Lys Lys Arg Ile Ile Ala Glu Thr Gly Ala Gly Gln His
            100                 105                 110

Gly Val Ala Thr Ala Thr Ala Ala Ala Met Phe Gly Met Glu Cys Glu
            115                 120                 125

Ile Phe Met Gly Glu Glu Asp Ile Lys Arg Gln Ala Leu Asn Val Phe
        130                 135                 140

Arg Met Lys Leu Leu Gly Ala Lys Val Thr Ala Val Thr Ser Gly Thr
145                 150                 155                 160

Arg Thr Leu Lys Asp Ala Val Asn Glu Ala Ile Arg Asp Trp Val Thr
                165                 170                 175

Asn Ile Glu Thr Thr Phe Tyr Val Ile Gly Ser Val Val Gly Pro His
            180                 185                 190

Pro Tyr Pro Thr Met Val Arg Asp Phe Gln Arg Val Ile Gly Asp Glu
            195                 200                 205

Thr Lys Glu Gln Ile Leu Glu Lys Glu Gly Arg Leu Pro Asp Tyr Val
        210                 215                 220

Val Ala Cys Val Gly Gly Gly Ser Asn Ala Met Gly Ile Phe Tyr Pro
225                 230                 235                 240

Phe Ile Glu Asp Lys Gly Val Lys Leu Val Gly Val Glu Ala Ala Gly
                245                 250                 255

Glu Gly Ile Glu Thr Gly Lys His Ala Ser Ala Met Ala Lys Gly Ser

```
              260                 265                 270
Val Gly Val Leu His Gly Met Met Thr Tyr Leu Leu Gln Asp Glu Glu
            275                 280                 285

Gly Lys Ile Leu Pro Val His Ser Ile Ser Ala Gly Leu Asp Tyr Pro
        290                 295                 300

Gly Val Gly Pro Glu His Ala Tyr Leu Lys Glu Ile Gly Arg Ala Glu
305                 310                 315                 320

Tyr Val Tyr Ala Thr Asp Glu Glu Ala Leu Ala Ala Phe Met Asp Leu
                325                 330                 335

Ser Arg Thr Glu Gly Ile Ile Pro Ala Leu Glu Ser Ala His Ala Leu
            340                 345                 350

Ala Tyr Ala Met Lys Leu Ala Lys Lys Leu Asp Glu Asp Lys Ile Ile
        355                 360                 365

Val Val Asn Leu Ser Gly Arg Gly Asp Lys Asp Val Asn Thr Val Ala
    370                 375                 380

Lys Val Met Gly Val Glu Leu
385                 390

<210> SEQ ID NO 12
<211> LENGTH: 391
<212> TYPE: PRT
<213> ORGANISM: Caldanaerobacter subterraneus

<400> SEQUENCE: 12

Met Lys Gly Arg Phe Gly Arg Phe Gly Gly Gln Tyr Val Pro Glu Thr
1               5                   10                  15

Val Met Asn Ala Leu Ile Glu Leu Arg Glu Phe Glu Glu Ala Lys
            20                  25                  30

Lys Asp Glu Lys Phe Met Glu Glu Tyr Arg Tyr Tyr Leu Lys Glu Tyr
        35                  40                  45

Ser Gly Arg Pro Thr Pro Leu Tyr Tyr Ala Glu Asn Leu Thr Lys Arg
    50                  55                  60

Leu Gly Gly Ala Lys Ile Tyr Leu Lys Arg Glu Asp Leu Asn His Thr
65                  70                  75                  80

Gly Ala His Lys Ile Asn Asn Val Leu Gly Gln Val Leu Leu Ala Lys
                85                  90                  95

Arg Met Gly Lys Lys Arg Ile Ile Ala Glu Thr Gly Ala Gly Gln His
            100                 105                 110

Gly Val Ala Thr Ala Thr Ala Ala Ala Met Phe Gly Met Glu Cys Glu
        115                 120                 125

Ile Phe Met Gly Glu Glu Asp Ile Lys Arg Gln Ala Leu Asn Val Phe
    130                 135                 140

Arg Met Lys Leu Leu Gly Ala Lys Val Thr Ala Val Thr Ser Gly Thr
145                 150                 155                 160

Arg Thr Leu Lys Asp Ala Val Asn Glu Ala Ile Arg Asp Trp Val Thr
                165                 170                 175

Asn Ile Glu Thr Thr Phe Tyr Val Ile Gly Ser Val Val Gly Pro His
            180                 185                 190

Pro Tyr Pro Thr Met Val Arg Asp Phe Gln Arg Val Ile Gly Asp Glu
        195                 200                 205

Thr Lys Glu Gln Ile Leu Glu Lys Glu Gly Arg Leu Pro Asp Tyr Val
    210                 215                 220

Val Ala Cys Val Gly Gly Gly Ser Asn Ala Met Gly Ile Phe Tyr Pro
225                 230                 235                 240
```

```
Phe Ile Glu Asp Lys Gly Val Lys Leu Ile Gly Val Glu Ala Ala Gly
                245                 250                 255
Glu Gly Ile Glu Thr Gly Lys His Ala Ser Ala Met Ala Lys Gly Ser
            260                 265                 270
Val Gly Val Leu His Gly Met Met Thr Tyr Leu Leu Gln Asp Glu Glu
        275                 280                 285
Gly Lys Ile Leu Pro Val His Ser Ile Ser Ala Gly Leu Asp Tyr Pro
    290                 295                 300
Gly Val Gly Pro Glu His Ala Tyr Leu Lys Glu Ile Gly Arg Ala Glu
305                 310                 315                 320
Tyr Val Tyr Ala Thr Asp Glu Glu Ala Leu Ala Ala Phe Met Asp Leu
                325                 330                 335
Ser Arg Thr Glu Gly Ile Ile Pro Ala Leu Glu Ser Ala His Ala Leu
            340                 345                 350
Ala Tyr Ala Met Lys Leu Ala Lys Lys Leu Asp Glu Asp Lys Ile Ile
        355                 360                 365
Val Val Asn Leu Ser Gly Arg Gly Asp Lys Asp Val Asn Thr Val Ala
    370                 375                 380
Lys Val Met Gly Val Glu Leu
385                 390

<210> SEQ ID NO 13
<211> LENGTH: 391
<212> TYPE: PRT
<213> ORGANISM: Defluviitoga tunisiensis

<400> SEQUENCE: 13

Met Lys Lys Gly Tyr Tyr Gly Gln Tyr Gly Gly Gln Tyr Val Pro Glu
1               5                   10                  15
Thr Leu Ile Pro Ala Leu Lys Glu Leu Glu Ala Ala Tyr Glu Glu Tyr
                20                  25                  30
Ser Lys Asp Pro Asp Phe Leu Lys Glu Tyr Asn Gly Leu Leu Ala Asp
            35                  40                  45
Tyr Ser Gly Arg Pro Thr Pro Leu Tyr Tyr Ala Asp Arg Phe Thr Glu
    50                  55                  60
Tyr Leu Asn Gly Ala Lys Ile Tyr Leu Lys Arg Glu Asp Leu Asn His
65                  70                  75                  80
Thr Gly Ala His Lys Ile Asn Asn Ala Leu Gly Gln Val Leu Leu Ala
                85                  90                  95
Lys Arg Met Gly Lys Lys Arg Ile Ile Ala Glu Thr Gly Ala Gly Gln
            100                 105                 110
His Gly Val Ala Thr Ala Thr Ala Ala Thr Lys Phe Gly Leu Glu Cys
        115                 120                 125
Val Ile Tyr Met Gly Ala Glu Asp Ile Lys Arg Gln Ser Leu Asn Val
    130                 135                 140
Tyr Lys Met Glu Met Leu Gly Ala Lys Val Val Pro Val Tyr Asn Gly
145                 150                 155                 160
Ser Gln Thr Leu Asn Glu Ala Val Asn Glu Ala Ile Arg Asp Trp Val
                165                 170                 175
Thr Asn Val Glu Asp Thr His Tyr Val Ile Gly Ser Val Val Gly Pro
            180                 185                 190
His Pro Tyr Pro Lys Ile Val Arg Asp Phe Gln Arg Ile Ile Gly Asp
        195                 200                 205
Glu Ala Lys Lys Gln Ile Ile Glu Lys Glu Gly Arg Leu Pro Asp Tyr
    210                 215                 220
```

```
Ile Ile Ala Cys Val Gly Gly Ser Asn Ala Ile Gly Ile Phe Tyr
225                 230                 235                 240

Pro Phe Val Glu Asp Gln Glu Val Lys Leu Ile Gly Val Glu Ala Ala
                245                 250                 255

Gly Lys Gly Leu Glu Thr Gly Leu His Ala Ala Leu Thr Ala Gly
                260                 265                 270

Lys Ile Gly Val Leu His Gly Ser Lys Ser Tyr Val Leu Gln Asp Glu
                275                 280                 285

Asn Gly Gln Ile Lys Leu Ala Tyr Ser Ile Ser Ala Gly Leu Asp Tyr
                290                 295                 300

Pro Gly Val Gly Pro Glu His Ser Tyr Leu Arg Asp Ile Lys Arg Ala
305                 310                 315                 320

Thr Tyr Thr Ser Val Thr Asp Glu Glu Ala Ile Glu Ala Phe Glu Leu
                325                 330                 335

Leu Thr Lys Leu Glu Gly Ile Ile Pro Ala Phe Glu Ser Ser His Ala
                340                 345                 350

Leu Ala Tyr Thr Met Lys Leu Ala Pro Gln Leu Asp Lys Asn Lys Ile
                355                 360                 365

Ile Ile Val Asn Leu Ser Gly Arg Gly Asp Lys Asp Val Asp Ala Tyr
370                 375                 380

Arg Asn Leu Asn Arg Asn Lys
385                 390

<210> SEQ ID NO 14
<211> LENGTH: 396
<212> TYPE: PRT
<213> ORGANISM: Desulfotomaculum kuznetsovii

<400> SEQUENCE: 14

Met Ser Leu Pro Asp Glu Arg Gly Tyr Phe Gly Ser Phe Gly Gly Arg
1               5                   10                  15

Tyr Val Pro Glu Thr Leu Met Pro Ala Leu Glu Glu Leu Thr Ala Ala
                20                  25                  30

Tyr Gln Glu Ala Arg Arg Asp Pro Ser Phe Trp Gln Glu Leu Glu Tyr
            35                  40                  45

Tyr Leu Gln Gln Tyr Val Gly Arg Pro Ser Pro Leu Tyr Phe Ala Arg
50                  55                  60

Arg Leu Ser Glu His Cys Arg Gly Ala Arg Ile Tyr Leu Lys Arg Glu
65                  70                  75                  80

Asp Leu Asn His Thr Gly Ala His Lys Ile Asn Asn Thr Ile Gly Gln
                85                  90                  95

Ile Leu Leu Ala Arg Arg Met Gly Lys Lys Arg Ile Ile Ala Glu Thr
                100                 105                 110

Gly Ala Gly Gln His Gly Val Ala Thr Ala Thr Ala Ala Ala Leu Phe
            115                 120                 125

Gly Met Glu Cys Ala Val Tyr Met Gly Glu Glu Asp Met Ala Arg Gln
130                 135                 140

Ala Leu Asn Val Phe Arg Met Arg Ile Leu Gly Ala Thr Val Val Gly
145                 150                 155                 160

Val Ala Ala Gly Ser Arg Thr Leu Lys Asp Ala Met Asn Glu Ala Met
                165                 170                 175

Arg Asp Trp Val Thr Asn Val Asp Thr Thr Tyr Tyr Leu Ile Gly Ser
                180                 185                 190

Val Ala Gly Pro His Pro Tyr Pro Val Met Val Arg Asp Phe Gln Arg
```

```
              195                 200                 205
Val Ile Gly Val Glu Thr Arg Arg Gln Val Gln Glu Gln Thr Gly Arg
210                 215                 220

Leu Pro Asp Val Ile Val Ala Cys Val Gly Gly Ser Asn Ala Met
225                 230                 235                 240

Gly Ile Phe His Pro Phe Leu Glu Asp Arg Glu Val Lys Leu Val Gly
                    245                 250                 255

Val Glu Ala Ala Gly Cys Gly Leu Glu Thr Gly Lys His Ala Ala Thr
                260                 265                 270

Leu Asn Arg Gly Arg Pro Gly Ile Leu His Gly Ser Lys Ser Tyr Val
            275                 280                 285

Leu Gln Asp Glu Asp Gly Gln Ile Asn Leu Ala His Ser Ile Ser Ala
290                 295                 300

Gly Leu Asp Tyr Pro Gly Val Gly Pro Glu His Ser Tyr Leu Lys Glu
305                 310                 315                 320

Thr Gly Arg Val Val Tyr Thr Ala Val Thr Asp Glu Glu Ala Leu Glu
                325                 330                 335

Ala Phe Gln Leu Leu Cys Arg Thr Glu Gly Ile Ile Pro Ala Leu Glu
                340                 345                 350

Ser Ala His Ala Leu Ala Gln Ala Val Lys Met Ala Gly Glu Met Pro
            355                 360                 365

Gln Asp Ala Ile Ile Val Val Asn Leu Ser Gly Arg Gly Asp Lys Asp
370                 375                 380

Val Gln Thr Val Ala Arg Ala Leu Gly Gly Glu Gly
385                 390                 395

<210> SEQ ID NO 15
<211> LENGTH: 393
<212> TYPE: PRT
<213> ORGANISM: Petrotoga mobilis

<400> SEQUENCE: 15

Met Lys Lys Ala Tyr Phe Gly Gln Tyr Gly Gly Arg Tyr Val Pro Glu
1               5                   10                  15

Thr Leu Ile Pro Ala Leu Glu Glu Leu Glu Glu Ala His Glu Lys Tyr
                20                  25                  30

Ser Lys Asp Pro Asp Phe Ile Asn Glu Tyr Gln Gly Leu Leu Lys Asp
            35                  40                  45

Tyr Cys Gly Arg Pro Thr Pro Leu Tyr Phe Ala Glu Arg Phe Thr Glu
50                  55                  60

Tyr Leu Asn Gly Pro Lys Ile Tyr Leu Lys Arg Glu Asp Leu Asn His
65                  70                  75                  80

Thr Gly Ala His Lys Ile Asn Asn Ala Leu Gly Gln Val Leu Leu Ala
                85                  90                  95

Lys Arg Met Asn Lys Lys Arg Ile Ile Ala Glu Thr Gly Ala Gly Gln
                100                 105                 110

His Gly Val Ala Thr Ala Thr Ala Ala Ala Arg Phe Gly Leu Glu Cys
            115                 120                 125

Ile Val Tyr Met Gly Ala Glu Asp Ile Arg Arg Gln Ala Leu Asn Val
130                 135                 140

Tyr Lys Met Arg Met Leu Gly Ala Lys Val Val Pro Val Tyr Ser Gly
145                 150                 155                 160

Ser Gln Thr Leu Lys Glu Ala Ile Asn Glu Ala Ile Arg Asp Trp Val
                165                 170                 175
```

-continued

Thr Asn Val Glu Asn Thr His Tyr Val Ile Gly Ser Val Val Gly Pro
                180                 185                 190

His Pro Tyr Pro Lys Ile Val Arg Asp Phe Gln Arg Val Ile Gly Asp
            195                 200                 205

Glu Ser Lys Asn Gln Ile Leu Glu Lys Glu Gly Arg Leu Pro Asp Tyr
        210                 215                 220

Ile Val Ala Cys Val Gly Gly Ser Asn Ala Met Gly Ile Phe Tyr
225                 230                 235                 240

Pro Phe Ile Glu Asp Lys Asp Val Glu Leu Ile Gly Val Glu Ala Ala
                245                 250                 255

Gly Lys Gly Leu Glu Thr Gly Gln His Ala Ala Ser Leu Thr Ala Gly
            260                 265                 270

Lys Ile Gly Val Leu His Gly Ser Lys Ser Tyr Val Leu Gln Asp Asp
        275                 280                 285

Asp Gly Gln Ile Gln Leu Ala Tyr Ser Ile Ser Ala Gly Leu Asp Tyr
    290                 295                 300

Pro Gly Val Gly Pro Glu His Ser Tyr Leu His Asp Glu Lys Arg Ala
305                 310                 315                 320

Gln Tyr Val Ser Ile Thr Asp Glu Glu Ala Leu Lys Gly Phe Glu Leu
                325                 330                 335

Leu Thr Lys Leu Glu Gly Ile Ile Pro Ala Phe Glu Ser Ser His Ala
            340                 345                 350

Ile Ala Tyr Ala Met Lys Ile Ala Pro Ser Leu Asp Lys Asp Lys Ile
        355                 360                 365

Met Val Ile Asn Leu Ser Gly Arg Gly Asp Lys Asp Val Asp Ser Tyr
370                 375                 380

Ile Lys Leu Gly Arg Glu Ala Leu Glu
385                 390

<210> SEQ ID NO 16
<211> LENGTH: 397
<212> TYPE: PRT
<213> ORGANISM: Aquifex aeolicus

<400> SEQUENCE: 16

Met Tyr Asn Tyr Pro Asp Glu Arg Gly Tyr Phe Gly Pro Phe Gly Gly
1               5                   10                  15

Lys Phe Val Pro Glu Thr Leu Met Tyr Ala Leu Glu Glu Leu Glu Glu
                20                  25                  30

Lys Tyr Arg Glu Leu Lys Ser Asp Pro Glu Phe Gln Lys Glu Leu Asp
            35                  40                  45

Tyr Tyr Leu Arg Glu Tyr Ala Gly Arg Pro Thr Pro Leu Tyr Phe Ala
        50                  55                  60

Glu Lys Leu Thr Lys Tyr Val Gly Gly Ala Lys Ile Tyr Leu Lys Arg
65                  70                  75                  80

Glu Asp Leu Leu His Thr Gly Ala His Lys Ile Asn Asn Thr Ile Gly
                85                  90                  95

Gln Cys Leu Leu Thr Lys Arg Met Gly Lys Lys Arg Val Ile Ala Glu
            100                 105                 110

Thr Gly Ala Gly Gln His Gly Val Ala Thr Ala Thr Ala Ser Ala Leu
        115                 120                 125

Phe Gly Leu Glu Cys Val Val Tyr Met Gly Glu Glu Asp Ala Glu Arg
    130                 135                 140

Gln Ala Leu Asn Val Phe Arg Met Lys Leu Leu Gly Ala Lys Val Glu
145                 150                 155                 160

Ile Val Lys Ser Gly Ser Arg Thr Leu Lys Asp Ala Ile Asn Glu Ala
                165                 170                 175

Leu Arg Asp Trp Val Thr Asn Val Glu Ser Thr His Tyr Val Ile Gly
            180                 185                 190

Ser Val Val Gly Pro His Pro Phe Pro Met Ile Val Arg Asp Phe Gln
        195                 200                 205

Ser Val Ile Gly Arg Glu Thr Lys Glu Gln Ile Leu Gln Lys Glu Gly
    210                 215                 220

Arg Leu Pro Asp Ala Ile Val Ala Cys Val Gly Gly Ser Asn Ala
225                 230                 235                 240

Met Gly Ile Phe Tyr Pro Phe Val Glu Asp Lys Gly Val Gln Leu Ile
                245                 250                 255

Gly Val Glu Ala Gly Gly Tyr Gly Leu Glu Thr Gly Gln His Ala Ala
            260                 265                 270

Ser Ile Cys Gly Gly Ser Val Gly Ile Leu His Gly Met Lys Ser Tyr
        275                 280                 285

Phe Leu Gln Asp Glu Glu Gly Gln Ile Gln Pro Thr His Ser Ile Ser
    290                 295                 300

Ala Gly Leu Asp Tyr Pro Gly Val Gly Pro Glu His Ala Leu Phe His
305                 310                 315                 320

Glu Ile Lys Arg Ala Lys Tyr Thr Thr Ala Thr Asp Glu Glu Ala Leu
                325                 330                 335

Glu Gly Phe Lys Leu Leu Ala Arg Thr Gly Ile Ile Pro Ala Leu
            340                 345                 350

Glu Ser Ala His Ala Val Ile Lys Ala Val Glu Val Ala Arg Glu Leu
        355                 360                 365

Gly Lys Asp Gly Ile Val Val Ile Asn Leu Ser Gly Arg Gly Asp Lys
    370                 375                 380

Asp Met Ala His Val Met Lys His Leu Ser Leu Glu Gly
385                 390                 395

<210> SEQ ID NO 17
<211> LENGTH: 415
<212> TYPE: PRT
<213> ORGANISM: Sulfurihydrogenibium azorense

<400> SEQUENCE: 17

Met Lys Lys Tyr Thr Phe Pro Asp Glu Arg Gly Tyr Tyr Gly Gln Phe
1               5                   10                  15

Gly Gly Lys Tyr Leu Pro Glu Thr Leu Ile Pro Ala Leu Glu Glu Leu
            20                  25                  30

Glu Gln Gln Tyr Leu Lys Ile Lys Asn Asp Gly Asp Phe Lys Arg Gln
        35                  40                  45

Leu Leu Tyr Tyr Leu Thr Glu Tyr Ala Gly Arg Pro Thr Pro Leu Tyr
    50                  55                  60

Phe Ala Ser Arg Leu Thr Gln Val Val Gly Gly Ala Lys Ile Tyr Leu
65                  70                  75                  80

Lys Arg Glu Asp Leu Leu His Thr Gly Ala His Lys Ile Asn Asn Thr
                85                  90                  95

Leu Gly Gln Val Leu Leu Thr Lys Arg Leu Gly Lys Lys Arg Ile Ile
            100                 105                 110

Ala Glu Thr Gly Ala Gly Gln His Gly Val Ser Thr Ala Thr Ala Ala
        115                 120                 125

Ala Leu Phe Gly Leu Glu Cys Thr Ile Tyr Met Gly Glu Glu Asp Ala

```
                130                 135                 140
Glu Arg Gln Ala Leu Asn Val Phe Arg Met Lys Leu Gly Ala Lys
145                 150                 155                 160

Val Glu Ile Val Lys Ser Gly Ser Arg Thr Leu Lys Asp Ala Val Asn
                165                 170                 175

Glu Ala Leu Arg Asp Trp Val Thr Asn Val Arg Thr Thr His Tyr Ile
            180                 185                 190

Ile Gly Ser Ala Leu Gly Pro His Pro Phe Pro Met Ile Val Arg Asp
                195                 200                 205

Phe Gln Ser Val Ile Gly Glu Val Lys Asn Gln Ile Leu Glu Ile
    210                 215                 220

Glu Gly Lys Leu Pro Asp Val Ile Val Ala Cys Val Gly Gly Gly Ser
225                 230                 235                 240

Asn Ala Ile Gly Ile Phe Tyr Pro Phe Ile Glu Asp Glu Glu Val Lys
                245                 250                 255

Leu Val Gly Val Glu Ala Gly Gly Tyr Gly Leu Glu Thr Gly Met His
                260                 265                 270

Ala Ala Ser Ile Val Gly Gly Ser Val Gly Val Leu His Gly Met Lys
                275                 280                 285

Ser Tyr Phe Leu Gln Asp Gln Trp Gly Gln Ile Glu Thr Thr His Ser
290                 295                 300

Ile Ser Ala Gly Leu Asp Tyr Pro Gly Val Gly Pro Glu His Ala Tyr
305                 310                 315                 320

Leu Lys Glu Ser Gly Arg Ala Thr Tyr Ile Thr Ala Thr Asp Glu Glu
                325                 330                 335

Ala Leu Glu Gly Phe Leu Leu Leu Ser Arg Thr Glu Gly Ile Ile Pro
            340                 345                 350

Ala Leu Glu Ser Ser His Ala Val Ile Lys Ala Val Glu Ile Ala Lys
                355                 360                 365

Asn Leu Asp Lys His Gln Ser Val Val Ile Asn Leu Ser Gly Arg Gly
            370                 375                 380

Asp Lys Asp Val Gln Ser Val Lys Asn Leu Leu Asp Thr Asp Lys Glu
385                 390                 395                 400

Leu Tyr Glu Arg Leu Leu Asn Lys Leu Lys Glu Lys Tyr Gly Val
                405                 410                 415

<210> SEQ ID NO 18
<211> LENGTH: 391
<212> TYPE: PRT
<213> ORGANISM: Thermoanaerobacter pseudethanolicus

<400> SEQUENCE: 18

Met Ser Gly Arg Phe Gly Arg Phe Gly Gly Gln Tyr Val Pro Glu Thr
1               5                   10                  15

Val Met Asn Ala Leu Ile Glu Leu Glu Arg Glu Phe Glu Lys Ala Lys
                20                  25                  30

Glu Asp Lys Asp Phe Met Glu Glu Tyr Arg Tyr Tyr Leu Arg Glu Tyr
            35                  40                  45

Ser Gly Arg Pro Thr Pro Leu Tyr Tyr Ala Glu Asn Leu Thr Lys Arg
        50                  55                  60

Leu Gly Gly Ala Lys Ile Tyr Leu Lys Arg Glu Asp Leu Asn His Thr
65              70                  75                  80

Gly Ala His Lys Ile Asn Asn Val Leu Gly Gln Ile Leu Leu Ala Lys
                85                  90                  95
```

```
Arg Met Asn Lys Lys Arg Val Ile Ala Glu Thr Gly Ala Gly Gln His
                100                 105                 110

Gly Val Ala Thr Ala Thr Ala Ala Met Phe Gly Met Glu Cys Glu
            115                 120                 125

Ile Phe Met Gly Glu Glu Asp Ile Lys Arg Gln Ser Leu Asn Val Phe
130                 135                 140

Arg Met Lys Leu Leu Gly Ala Lys Val Thr Pro Val Thr Thr Gly Thr
145                 150                 155                 160

Lys Thr Leu Lys Asp Ala Val Asn Glu Ala Ile Arg Asp Trp Val Thr
                165                 170                 175

Asn Ile Asp Asn Thr Phe Tyr Val Ile Gly Ser Val Val Gly Pro His
                180                 185                 190

Pro Tyr Pro Thr Met Val Arg Asp Phe Gln Arg Val Ile Gly Asp Glu
            195                 200                 205

Ala Lys Glu Gln Ile Leu Gln Lys Glu Gly Arg Leu Pro Asp Tyr Val
210                 215                 220

Ile Ala Cys Val Gly Gly Gly Ser Asn Ala Met Gly Ile Phe Tyr Pro
225                 230                 235                 240

Phe Ile Glu Asp Lys Glu Val Lys Leu Ile Gly Val Glu Ala Ala Gly
                245                 250                 255

Glu Gly Ile Glu Thr Gly Lys His Ala Ala Ala Met Ala Lys Gly Ser
            260                 265                 270

Val Gly Val Leu His Gly Met Met Thr Tyr Leu Leu Gln Asp Glu Glu
            275                 280                 285

Gly Arg Ile Met Pro Val Tyr Ser Ile Ser Ala Gly Leu Asp Tyr Pro
            290                 295                 300

Gly Val Gly Pro Glu His Ala Phe Leu Lys Glu Ser Asn Arg Ala Gln
305                 310                 315                 320

Tyr Val Tyr Ala Thr Asp Glu Glu Ala Leu Ala Ala Phe Met Asp Leu
                325                 330                 335

Ser Gln Thr Glu Gly Ile Ile Pro Ala Leu Glu Ser Ala His Ala Leu
            340                 345                 350

Ala Tyr Ala Met Lys Leu Ala Pro Asn Leu Thr Lys Asp Asn Ile Ile
            355                 360                 365

Ile Val Asn Leu Ser Gly Arg Gly Asp Lys Asp Val Asn Thr Val Ala
370                 375                 380

Lys Val Leu Gly Val Glu Leu
385                 390

<210> SEQ ID NO 19
<211> LENGTH: 404
<212> TYPE: PRT
<213> ORGANISM: Thermus thermophilus

<400> SEQUENCE: 19

Met Leu Thr Leu Pro Asp Phe Pro Leu Pro Asp Ala Arg Gly Arg Phe
1               5                   10                  15

Gly Pro Tyr Gly Gly Arg Tyr Val Pro Glu Thr Leu Ile Pro Ala Leu
            20                  25                  30

Glu Glu Leu Glu Ala Ala Tyr Arg Glu Ala Lys Lys Asp Pro Ala Phe
        35                  40                  45

Leu Glu Glu Leu Asp His Tyr Leu Arg Gln Phe Ala Gly Arg Pro Thr
50                  55                  60

Pro Leu Tyr His Ala Lys Arg Leu Ser Glu Tyr Trp Gly Gly Ala Gln
65                  70                  75                  80
```

```
Val Phe Leu Lys Arg Glu Asp Leu Leu His Thr Gly Ala His Lys Ile
            85                  90                  95

Asn Asn Thr Leu Gly Gln Ala Leu Leu Ala Arg Arg Met Gly Lys Arg
        100                 105                 110

Arg Val Ile Ala Glu Thr Gly Ala Gly Gln His Gly Val Ser Val Ala
        115                 120                 125

Thr Val Ala Ala Leu Phe Gly Leu Glu Cys Val Val Tyr Met Gly Glu
    130                 135                 140

Glu Asp Val Arg Arg Gln Ala Leu Asn Val Phe Arg Met Lys Leu Leu
145                 150                 155                 160

Gly Ala Glu Val Arg Pro Val Ala Gly Ser Arg Thr Leu Lys Asp
            165                 170                 175

Ala Thr Asn Glu Ala Ile Arg Asp Trp Ile Thr Asn Val Arg Thr Thr
        180                 185                 190

Phe Tyr Ile Leu Gly Ser Val Val Gly Pro His Pro Tyr Pro Met Met
        195                 200                 205

Val Arg Asp Phe Gln Ser Val Ile Gly Glu Glu Val Lys Arg Gln Ser
    210                 215                 220

Leu Glu Leu Phe Gly Arg Leu Pro Asp Ala Leu Ile Ala Ala Val Gly
225                 230                 235                 240

Gly Gly Ser Asn Ala Ile Gly Leu Phe Ala Pro Phe Ala Tyr Leu Pro
            245                 250                 255

Glu Gly Arg Pro Lys Leu Ile Gly Val Glu Ala Ala Gly Glu Gly Leu
        260                 265                 270

Ser Thr Gly Arg His Ala Ala Ser Ile Gly Ala Gly Lys Arg Gly Val
        275                 280                 285

Leu His Gly Ser Tyr Met Tyr Leu Leu Tyr Asp His Asp Gly Gln Ile
    290                 295                 300

Thr Pro Ala His Ser Val Ser Ala Gly Leu Asp Tyr Pro Gly Val Gly
305                 310                 315                 320

Pro Glu His Ser Tyr Tyr Ala Asp Ala Gly Val Ala Glu Tyr Ala Ser
            325                 330                 335

Val Thr Asp Glu Glu Ala Leu Glu Gly Phe Lys Leu Leu Ala Arg Leu
        340                 345                 350

Glu Gly Ile Ile Pro Ala Leu Glu Ser Ala His Ala Ile Ala Tyr Ala
        355                 360                 365

Ala Lys Val Val Pro Glu Met Asp Lys Asp Gln Val Val Val Ile Asn
    370                 375                 380

Leu Ser Gly Arg Gly Asp Lys Asp Val Thr Glu Val Met Arg Leu Leu
385                 390                 395                 400

Gly Gly Glu Leu

<210> SEQ ID NO 20
<211> LENGTH: 404
<212> TYPE: PRT
<213> ORGANISM: Thermus thermophilus

<400> SEQUENCE: 20

Met Leu Thr Leu Pro Asp Phe Pro Leu Pro Asp Ala Arg Gly Arg Phe
1               5                   10                  15

Gly Pro Tyr Gly Gly Arg Tyr Val Pro Glu Thr Leu Ile Pro Ala Leu
            20                  25                  30

Glu Glu Leu Glu Ala Ala Tyr Arg Glu Ala Lys Lys Asp Pro Ala Phe
        35                  40                  45
```

Leu Glu Glu Leu Asp His Tyr Leu Arg Gln Phe Ala Gly Arg Pro Thr
            50                  55                  60

Pro Leu Tyr His Ala Lys Arg Leu Ser Glu Tyr Trp Gly Gly Ala Gln
 65                  70                  75                  80

Val Tyr Leu Lys Arg Glu Asp Leu Leu His Thr Gly Ala His Lys Ile
                 85                  90                  95

Asn Asn Thr Leu Gly Gln Ala Leu Leu Ala Arg Arg Met Gly Lys Arg
            100                 105                 110

Arg Val Ile Ala Glu Thr Gly Ala Gly Gln His Gly Val Ser Val Ala
            115                 120                 125

Thr Val Ala Ala Leu Phe Gly Leu Glu Cys Val Val Tyr Met Gly Glu
130                 135                 140

Glu Asp Val Arg Arg Gln Ala Leu Asn Val Phe Arg Met Lys Leu Leu
145                 150                 155                 160

Gly Ala Glu Val Arg Pro Val Ala Ala Gly Ser Arg Thr Leu Lys Asp
                165                 170                 175

Ala Thr Asn Glu Ala Ile Arg Asp Trp Ile Thr Asn Val Arg Thr Thr
            180                 185                 190

Phe Tyr Ile Leu Gly Ser Val Val Gly Pro His Pro Tyr Pro Met Met
            195                 200                 205

Val Arg Asp Phe Gln Ser Val Ile Gly Glu Val Lys Arg Gln Ser
210                 215                 220

Leu Glu Leu Phe Gly Arg Leu Pro Asp Ala Leu Ile Ala Ala Val Gly
225                 230                 235                 240

Gly Gly Ser Asn Ala Ile Gly Leu Phe Ala Pro Phe Ala Tyr Leu Pro
                245                 250                 255

Glu Gly Arg Pro Lys Leu Ile Gly Val Glu Ala Ala Gly Glu Gly Leu
            260                 265                 270

Ser Thr Gly Arg His Ala Ala Ser Ile Gly Ala Gly Lys Arg Gly Val
            275                 280                 285

Leu His Gly Ser Tyr Met Tyr Leu Leu Tyr Asp His Asp Gly Gln Ile
290                 295                 300

Thr Pro Ala His Ser Val Ser Ala Gly Leu Asp Tyr Pro Gly Val Gly
305                 310                 315                 320

Pro Glu His Ser Tyr Tyr Ala Asp Ala Gly Val Ala Glu Tyr Ala Ser
                325                 330                 335

Val Thr Asp Glu Glu Ala Leu Glu Gly Phe Lys Leu Leu Ala Arg Leu
            340                 345                 350

Glu Gly Ile Ile Pro Ala Leu Glu Ser Ala His Ala Ile Ala Tyr Ala
            355                 360                 365

Ala Lys Val Val Pro Glu Met Asp Lys Asp Gln Val Val Val Ile Asn
370                 375                 380

Leu Ser Gly Arg Gly Asp Lys Asp Val Thr Glu Val Met Arg Leu Leu
385                 390                 395                 400

Gly Gly Glu Leu

<210> SEQ ID NO 21
<211> LENGTH: 394
<212> TYPE: PRT
<213> ORGANISM: Clostridium acetobutylicum

<400> SEQUENCE: 21

Met Asn Gly Arg Phe Gly Lys Phe Gly Gly Gln Tyr Val Pro Glu Thr
1               5                   10                  15

Leu Met Asn Ala Ile Asn Glu Leu Glu Val Glu Phe Asn Lys Ala Ile
            20                  25                  30

Asn Asp Glu Lys Phe Met Met Glu Tyr Lys Tyr Leu Glu Lys Tyr
        35                  40                  45

Val Gly Arg Glu Thr Pro Leu Tyr Phe Ala Glu Asn Met Thr Lys Asn
 50                  55                  60

Leu Gly Gly Ala Lys Ile Tyr Leu Lys Arg Glu Asp Leu Asn His Thr
 65                  70                  75                  80

Gly Ser His Lys Leu Asn Asn Ala Leu Gly Gln Val Leu Leu Ala Lys
                85                  90                  95

Arg Met Gly Lys Lys Arg Val Ile Ala Glu Thr Gly Ala Gly Gln His
            100                 105                 110

Gly Val Ala Thr Ala Thr Ala Ala Leu Phe Gly Leu Glu Cys Glu
            115                 120                 125

Val Phe Met Gly Ala Glu Asp Val Glu Arg Gln Ala Leu Asn Val Phe
130                 135                 140

Arg Met Lys Ile Leu Gly Ala Lys Val Asn Ser Val Lys Ser Gly Thr
145                 150                 155                 160

Asn Thr Leu Lys Asp Ala Ile Asn Ala Ala Met Arg Asp Trp Val Thr
                165                 170                 175

Asn Ile Asp Asn Thr Tyr Tyr Val Ile Gly Ser Val Met Gly Pro His
            180                 185                 190

Pro Tyr Pro Thr Ile Val Lys Asp Phe Gln Lys Ile Ile Gly Glu Glu
            195                 200                 205

Ala Arg Lys Gln Ile Leu Lys Ala Glu Gly Arg Leu Pro Asp Tyr Val
            210                 215                 220

Val Ala Cys Val Gly Gly Gly Ser Asn Ser Met Gly Ile Phe Tyr Pro
225                 230                 235                 240

Phe Ile Lys Asp Glu Gly Val Lys Leu Ile Gly Val Glu Ala Ala Gly
                245                 250                 255

Leu Gly Ile Asp Thr Pro Met His Ala Ala Thr Leu Thr Lys Gly Ser
            260                 265                 270

Val Gly Ile Ile His Gly Met Met Thr Tyr Val Leu Gln Asp Glu Asp
            275                 280                 285

Gly Gln Ile Thr Pro Ala Tyr Ser Val Ser Ala Gly Leu Asp Tyr Pro
290                 295                 300

Gly Val Gly Pro Gln His Ser Tyr Leu Lys Glu Lys Glu Arg Ala Ser
305                 310                 315                 320

Tyr Glu Ala Val Thr Asp Lys Glu Ala Leu Lys Ala Phe Leu Tyr Leu
                325                 330                 335

Ser Glu Lys Glu Gly Ile Ile Pro Ala Leu Glu Ser Ser His Ala Val
            340                 345                 350

Ala Tyr Ala Met Lys Leu Ala Pro Ser Leu Ser Lys Asp Glu Ile Val
            355                 360                 365

Ile Ile Asn Leu Ser Gly Arg Gly Asp Lys Asp Val Asn Thr Val Met
            370                 375                 380

Lys Asn Met Glu Glu Asn Lys Asn Gly Lys
385                 390

<210> SEQ ID NO 22
<211> LENGTH: 399
<212> TYPE: PRT
<213> ORGANISM: Legionella pneumophila

<400> SEQUENCE: 22

Met Ile Lys Lys Glu Leu Pro Asp Glu Phe Gly His Phe Gly Pro Tyr
1               5                   10                  15

Gly Gly Met Phe Val Ala Asp Thr Leu Val Ser Ala Leu Lys Gln Leu
            20                  25                  30

Glu His Ala Tyr Thr Lys Tyr Arg Asn Asp Gln Asp Phe Leu Ser Glu
        35                  40                  45

Leu His Thr Glu Leu Lys Asp Tyr Val Gly Arg Pro Asn Pro Leu Tyr
    50                  55                  60

His Ala Val His Leu Ser Lys Lys Ile Gly Ala Gln Ile Tyr Leu
65                  70                  75                  80

Lys Arg Glu Asp Leu Asn His Thr Gly Ala His Lys Ile Asn Asn Thr
                85                  90                  95

Ile Gly Gln Ala Leu Leu Ala Lys Arg Met Gly Lys Thr Arg Val Ile
            100                 105                 110

Ala Glu Thr Gly Ala Gly Gln His Gly Val Ala Thr Ala Thr Val Ala
        115                 120                 125

Ala Lys Phe Gly Phe Gln Cys Val Val Tyr Met Gly Ser Glu Asp Ile
    130                 135                 140

Lys Arg Gln Ser Ser Asn Val Tyr Arg Met Lys Leu Leu Gly Ala Glu
145                 150                 155                 160

Val Val Pro Val Thr Ser Gly Ser Lys Thr Leu Lys Asp Ala Leu Asn
                165                 170                 175

Glu Ala Leu Arg Asp Trp Val Ser His Val Asp Asp Thr Phe Tyr Ile
            180                 185                 190

Ile Gly Thr Val Ala Gly Pro His Pro Tyr Pro Gln Met Val Arg Asp
        195                 200                 205

Phe Gln Ala Ile Ile Gly Val Glu Ala Arg Ala Gln His Met Glu Lys
    210                 215                 220

Thr Gly Arg Leu Pro Asp Ala Leu Val Ala Cys Val Gly Gly Gly Ser
225                 230                 235                 240

Asn Ala Ile Gly Leu Phe Tyr Pro Phe Leu Asn Asp Gln Ser Val Met
                245                 250                 255

Ile Tyr Gly Val Glu Ala Gly Gly Lys Gly Ile Glu Thr Gly Glu His
            260                 265                 270

Ser Ala Ser Leu Ile Ala Gly Lys Pro Gly Val Leu His Gly Asn Arg
        275                 280                 285

Thr Tyr Leu Leu Cys Asp Glu Tyr Gly Gln Val Lys Asp Thr His Ser
    290                 295                 300

Val Ser Ala Gly Leu Asp Tyr Pro Gly Val Gly Pro Glu His Ala Tyr
305                 310                 315                 320

Leu Lys Asp Thr Gly Arg Val Ile Tyr Lys Ala Ile Asn Asp Ser Glu
                325                 330                 335

Ala Leu Asp Ala Phe Arg Leu Leu Thr His Thr Glu Gly Ile Ile Pro
            340                 345                 350

Ala Leu Glu Ser Ser His Ala Val Ala Tyr Ala Ile Gln Leu Ala Lys
        355                 360                 365

Thr Met Ser Lys Glu Gln Ser Ile Ile Val Asn Leu Ser Gly Arg Gly
    370                 375                 380

Asp Lys Asp Met His Thr Val Ala Ala Ile Asp Gly Ile Thr Ile
385                 390                 395

<210> SEQ ID NO 23

<211> LENGTH: 388
<212> TYPE: PRT
<213> ORGANISM: Pyrococcus abyssi

<400> SEQUENCE: 23

```
Met Trp Phe Gly Lys Phe Gly Gly Gln Tyr Val Pro Glu Thr Leu Met
1               5                   10                  15

Glu Pro Leu Arg Glu Leu Glu Lys Ala Tyr Lys Arg Leu Lys Asn Asp
            20                  25                  30

Glu Glu Phe Asn Arg Gln Leu Asp Tyr Tyr Leu Arg Thr Trp Ala Gly
        35                  40                  45

Arg Pro Thr Pro Leu Tyr Tyr Ala Glu Arg Leu Thr Lys Lys Val Gly
    50                  55                  60

Gly Ala Lys Ile Tyr Leu Lys Arg Glu Asp Leu Leu His Gly Gly Ala
65                  70                  75                  80

His Lys Thr Asn Asn Ala Ile Gly Gln Ala Leu Leu Ala Lys Phe Met
                85                  90                  95

Gly Lys Thr Arg Leu Ile Ala Glu Thr Gly Ala Gly Gln His Gly Val
            100                 105                 110

Ala Thr Ala Met Ala Gly Ala Leu Leu Gly Met Lys Val Asp Ile Tyr
        115                 120                 125

Met Gly Ala Glu Asp Val Glu Arg Gln Lys Met Asn Val Phe Arg Met
    130                 135                 140

Lys Leu Leu Gly Ala Asn Val Ile Pro Val His Thr Gly Ser Lys Thr
145                 150                 155                 160

Leu Lys Asp Ala Ile Asn Glu Ala Leu Arg Asp Trp Val Ala Thr Phe
                165                 170                 175

Glu Tyr Ser His Tyr Leu Ile Gly Ser Val Val Gly Pro His Pro Tyr
            180                 185                 190

Pro Ile Ile Val Arg Asp Phe Gln Ser Val Ile Gly Arg Glu Ala Arg
        195                 200                 205

Glu Gln Ile Leu Glu Ala Glu Gly Asp Leu Pro Asp Val Ile Val Ala
    210                 215                 220

Cys Val Gly Gly Gly Ser Asn Ala Met Gly Ile Phe Tyr Pro Phe Val
225                 230                 235                 240

Lys Asp Lys Ser Val Arg Leu Ile Gly Val Glu Ala Gly Gly Lys Gly
                245                 250                 255

Ile Glu Ser Gly Lys His Ser Ala Ser Leu Asn Ala Gly Glu Ile Gly
            260                 265                 270

Val Phe His Gly Met Leu Ser Tyr Phe Leu Gln Asp Glu Glu Gly Gln
        275                 280                 285

Ile Arg Thr Thr His Ser Ile Ala Pro Gly Leu Asp Tyr Pro Gly Val
    290                 295                 300

Gly Pro Glu His Ala Tyr Leu Lys Glu Ser Gly Arg Ala Glu Tyr Val
305                 310                 315                 320

Thr Val Thr Asp Glu Glu Ala Leu Arg Ala Phe His Glu Leu Ser Arg
                325                 330                 335

Thr Glu Gly Ile Ile Pro Ala Leu Glu Ser Ala His Ala Val Ala Tyr
            340                 345                 350

Ala Ile Lys Leu Ala Arg Glu Met Ser Arg Asp Val Ile Ile Val
        355                 360                 365

Asn Leu Ser Gly Arg Gly Asp Lys Asp Leu Asp Ile Val Leu Lys Val
    370                 375                 380

Ser Gly Asn Val
```

<210> SEQ ID NO 24
<211> LENGTH: 404
<212> TYPE: PRT
<213> ORGANISM: Methanocaldococcus jannaschii

<400> SEQUENCE: 24

```
Met Ser Ile Leu Lys Lys Tyr Lys Asp Met Tyr Pro Asp Glu Asn Gly
1               5                   10                  15

Lys Phe Gly Ile Tyr Gly Gly Lys Phe Val Pro Glu Thr Leu Met Pro
            20                  25                  30

Ala Ile Ala Glu Leu Glu Glu Ala Phe Lys Arg Phe Trp Ile Asn Asn
        35                  40                  45

Glu Gly Asn Phe Arg Glu Glu Phe Tyr Ala Leu Leu Arg Asp Tyr Val
    50                  55                  60

Gly Arg Pro Thr Pro Leu Tyr Tyr Ala Glu Arg Leu Ser Glu Glu Leu
65                  70                  75                  80

Gly Cys Lys Val Tyr Leu Lys Arg Glu Asp Leu Ala His Leu Gly Ala
                85                  90                  95

His Lys Ile Asn Asn Ala Leu Gly Gln Ala Leu Leu Ala Lys Lys Met
            100                 105                 110

Gly Lys Lys Arg Val Ile Ala Glu Thr Gly Ala Gly Gln His Gly Val
        115                 120                 125

Ala Thr Ala Ala Ala Cys Ala Lys Leu Gly Leu Glu Cys Ile Ile Tyr
    130                 135                 140

Met Gly Ala Lys Asp Val Glu Arg Gln Lys Leu Asn Val Phe Arg Met
145                 150                 155                 160

Glu Leu Met Gly Ala Lys Val Ile Pro Val Phe Gly Gly Ser Gln Thr
                165                 170                 175

Leu Lys Asp Ala Val Asn Glu Ala Leu Arg Asp Trp Thr Thr Asn Val
            180                 185                 190

Arg Thr Thr Tyr Tyr Leu Leu Gly Ser Ala Leu Gly Pro His Pro Tyr
        195                 200                 205

Pro Met Met Val Arg Glu Phe Gln Arg Val Ile Gly Lys Glu Leu Lys
    210                 215                 220

Glu Gln Ile Leu Glu Lys Glu Gly Arg Leu Pro Asp Val Ile Val Ala
225                 230                 235                 240

Cys Val Gly Gly Gly Ser Asn Ala Ile Gly Ala Phe Tyr Glu Phe Leu
                245                 250                 255

Asp Asp Asp Val Glu Leu Tyr Ala Val Glu Ala Gly Gly Lys Gly Ile
            260                 265                 270

Glu Thr Gly Met His Gly Ala Ser Leu Cys Ala Gly Val Gly Val
        275                 280                 285

Leu His Gly Ala Lys Ile Tyr Val Lys Glu Asp Glu Phe Gly Gln Ile
    290                 295                 300

Glu Glu Ser Tyr Ser Ile Ser Ala Gly Leu Asp Tyr Pro Gly Val Gly
305                 310                 315                 320

Pro Glu Leu Ser Phe Leu Lys Asp Glu Gly Arg Ile Lys Ala Val Cys
                325                 330                 335

Val Thr Asp Asp Glu Ala Leu Glu Ala Phe Gln Leu Leu Cys Arg Leu
            340                 345                 350

Glu Gly Ile Leu Pro Ala Leu Glu Ser Ser His Ala Leu Ala Tyr Ala
        355                 360                 365
```

Val Lys Leu Ala Asp Lys Leu Asp Lys Asp Asp Ile Met Val Ile Asn
370                 375                 380

Leu Ser Gly Arg Gly Asp Lys Asp Val Gln Thr Val Ala Lys Ala Leu
385                 390                 395                 400

Gly Arg Glu Ile

<210> SEQ ID NO 25
<211> LENGTH: 389
<212> TYPE: PRT
<213> ORGANISM: Thermococcus kodakarensis

<400> SEQUENCE: 25

Met Asp Asp Met Phe Phe Gly Arg Phe Gly Gln Phe Val Pro Glu
1               5                   10                  15

Thr Leu Ile Glu Pro Leu Lys Lys Leu Glu Arg Ala Tyr Lys Lys Phe
            20                  25                  30

Lys Asp Asp Pro Glu Phe Asn Glu Thr Leu Glu Tyr Tyr Leu Arg Asn
        35                  40                  45

Trp Ala Gly Arg Pro Thr Pro Leu Tyr Tyr Ala Glu Arg Leu Ser Lys
50                  55                  60

Lys Leu Gly Gly Ala Lys Ile Tyr Leu Lys Arg Glu Asp Leu Leu His
65                  70                  75                  80

Gly Gly Ala His Lys Thr Asn Asn Gly Ile Gly Gln Ala Leu Leu Ala
                85                  90                  95

Lys Phe Met Gly Lys Glu Arg Leu Ile Ala Glu Thr Gly Ala Gly Gln
            100                 105                 110

His Gly Val Ala Thr Ala Met Ala Gly Ala Leu Leu Gly Met Lys Val
        115                 120                 125

Asp Val Tyr Met Gly Ala Glu Asp Val Glu Arg Gln Lys Met Asn Val
130                 135                 140

Phe Arg Met Gly Leu Leu Gly Ala Arg Val Ile Pro Val Glu Ser Gly
145                 150                 155                 160

Ser Arg Thr Leu Lys Asp Ala Ile Asn Glu Ala Leu Arg Asp Trp Val
                165                 170                 175

Ala Thr Phe Glu Tyr Ser His Tyr Leu Ile Gly Ser Val Val Gly Pro
            180                 185                 190

Tyr Pro Tyr Pro Val Ile Val Arg Asp Phe Gln Ser Val Ile Gly Arg
        195                 200                 205

Glu Ala Arg Glu Gln Ile Leu Glu Ala Glu Gly Thr Leu Pro Asp Ala
210                 215                 220

Val Val Ala Cys Val Gly Gly Ser Asn Ala Met Gly Ile Phe Tyr
225                 230                 235                 240

Pro Phe Val Asn Asp Arg Val Arg Leu Ile Gly Val Glu Ala Gly Gly
                245                 250                 255

Lys Gly Leu Glu Thr Gly Leu His Ala Ala Ser Leu Asn Ala Gly Glu
            260                 265                 270

Leu Gly Val Phe His Gly Met Leu Ser Tyr Phe Leu Gln Asn Glu Glu
        275                 280                 285

Gly Gln Ile Thr Pro Thr His Ser Val Ser Ala Gly Leu Asp Tyr Pro
290                 295                 300

Gly Val Gly Pro Glu His Ala Tyr Leu Lys Asp Ser Gly Arg Ala Glu
305                 310                 315                 320

Tyr Val Thr Val Thr Asp Glu Glu Ala Leu Arg Ala Phe His Glu Leu
                325                 330                 335

Ser Arg Thr Glu Gly Ile Leu Pro Ala Leu Glu Ser Ala His Ala Val
            340                 345                 350

Ala Tyr Ala Met Lys Ile Ala Pro Glu Met Asp Lys Asp Glu Ile Ile
            355                 360                 365

Ile Val Asn Leu Ser Gly Arg Gly Asp Lys Asp Leu Asp Ile Val Arg
        370                 375                 380

Arg Val Gly Asn Val
385

<210> SEQ ID NO 26
<211> LENGTH: 389
<212> TYPE: PRT
<213> ORGANISM: Methanococcus aeolicus

<400> SEQUENCE: 26

Met Glu Tyr Lys Phe Gly Glu Tyr Gly Gly Gln Tyr Val Pro Glu Val
1               5                   10                  15

Leu Met Pro Ser Leu Lys Glu Leu Glu Lys Ala Tyr Lys Lys Tyr Lys
            20                  25                  30

Asp Asp Pro Glu Phe Lys Glu Glu Leu Glu Tyr Tyr Leu Lys Gln Tyr
        35                  40                  45

Ala Gly Arg Glu Thr Pro Leu Tyr Phe Ala Glu Asn Leu Thr Lys Lys
    50                  55                  60

Met Gly Gly Ala Lys Ile Tyr Leu Lys Arg Glu Asp Leu Leu Leu Gly
65                  70                  75                  80

Gly Ala His Lys Ile Asn Asn Ser Leu Gly Gln Ala Leu Leu Ala Lys
                85                  90                  95

Arg Ile Gly Lys Thr Arg Ile Ile Ala Glu Thr Gly Ala Gly Glu His
            100                 105                 110

Gly Leu Ser Thr Ala Met Val Gly Ala Leu Phe Gly Leu Lys Ala Lys
        115                 120                 125

Ile Tyr Met Gly Ala Val Asp Val Glu Arg Gln Lys Leu Asn Val Tyr
    130                 135                 140

Lys Met Arg Leu His Gly Ala Glu Val His Ala Val Gln Ser Gly Ser
145                 150                 155                 160

Lys Thr Leu Lys Asp Ala Ile Asn Glu Ala Leu Arg Asp Trp Val Glu
                165                 170                 175

Thr Phe Glu Asp Thr His Tyr Ile Ile Gly Ser Ala Val Gly Pro Tyr
            180                 185                 190

Pro Phe Pro Ser Met Val Arg Asp Phe Gln Ser Val Ile Gly Lys Glu
        195                 200                 205

Ala Lys Lys Gln Ile Leu Glu Ala Glu Gly Arg Leu Pro Asp Ser Ile
    210                 215                 220

Val Ala Cys Val Gly Gly Gly Ser Asn Ser Ile Gly Ile Phe Asn Glu
225                 230                 235                 240

Phe Lys Gln Asp Lys Glu Val Lys Leu Ile Gly Val Glu Ala Ala Gly
                245                 250                 255

Glu Gly Leu Asp Thr Asp Arg His Gly Ala Ala Ile Leu Lys Gly Lys
            260                 265                 270

Lys Gly Val Leu His Gly Met Leu Ser Lys Phe Leu Gln Asp Asp
        275                 280                 285

Gly Gln Ile Ala Glu Thr Tyr Ser Ile Ser Ala Gly Leu Asp Tyr Pro
    290                 295                 300

Gly Val Gly Pro Glu His Ala Tyr Leu Asp Glu Ile Lys Arg Val Glu
305                 310                 315                 320

Tyr Ala Gly Ile Thr Asp Val Glu Ala Leu Asp Ala Phe Ser Thr Leu
              325                 330                 335

Ser Lys Thr Glu Gly Ile Ile Pro Ala Leu Glu Ser Ser His Ala Val
          340                 345                 350

Ala His Gly Met Lys Ile Ala Lys Glu Met Asp Lys Asp Glu Ile Ile
              355                 360                 365

Ile Ile Asn Leu Ser Gly Arg Gly Asp Lys Asp Ile His Thr Val Met
          370                 375                 380

Asn Phe Ile Glu Phe
385

<210> SEQ ID NO 27
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gaaataattt tgtttaactt taagaaggag atatacatat g                          41

<210> SEQ ID NO 28
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gccggatctc agtggtggtg gtggtggtgc tcgag                                 35

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 29

His His His His His His
1               5

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Gly Gly Ser
1

METHOD FOR THE SYNTHESIS OF TRYPTOPHAN ANALOGS IN AQUEOUS SOLVENTS AT REDUCED TEMPERATURES

CROSS-REFERENCE TO RELATED APPLICATIONS

The present application claims priority to U.S. Provisional Pat. Appl. No. 62/637,262, filed on Mar. 1, 2018, which application is incorporated herein by reference in its entirety.

STATEMENT AS TO RIGHTS TO INVENTIONS MADE UNDER FEDERALLY SPONSORED RESEARCH AND DEVELOPMENT

This invention was made with government support under Grant No. GM117635 awarded by the National Institutes of Health. The government has certain rights in the invention.

REFERENCE TO A SEQUENCE LISTING

The instant application contains a Sequence Listing which has been submitted electronically in ASCII format and is hereby incorporated by reference in its entirety. Said ASCII copy, created on Mar. 21, 2019, is named 086544-1123769_022210PC_SL.txt and is 90,527 bytes in size.

BACKGROUND OF THE INVENTION

Noncanonical α-amino acids (ncAAs) resemble the building blocks of natural proteins but are not themselves used in protein synthesis. Despite this, ncAAs are prevalent precursors for functional synthetic compounds, including over 12% of the 200 top-selling pharmaceuticals.[1] However, ncAAs are challenging synthetic targets, since they possess at minimum two reactive functional groups (the amine and carboxylic acid) and typically have at least one stereocenter. As a result, synthetic routes to ncAAs typically require multiple steps, most of which use organic solvents.[2,3] One of the most direct routes to ncAAs is to add a nucleophile to the β-position of a serine-derived lactone[4-6] or aziridine[7-8] (FIG. 1A), but this approach has certain drawbacks, such as the need to pre-synthesize the water-sensitive electrophilic reactants.

Enzymes are widely applied to the synthesis of ncAAs since they circumvent many of the limitations of chemical methods. Not only do these catalysts function in aqueous media, but they also exhibit chemoselectivity that obviates the need for protecting groups, thereby trimming synthetic steps. In addition, the reactions are often highly stereoselective. Unfortunately, most enzymatic methods to synthesize ncAAs, such as those that rely on hydrolases or transaminases, require that the majority of the final product be synthesized in advance, usually by chemical means, with the enzyme only appearing at the end to set the stereochemistry. By contrast, enzymes like tryptophan synthase,[9-14] which uses the cofactor pyridoxal 5'-phosphate (PLP, FIG. 1B), can form ncAAs by nucleophilic substitution at the β-position of readily available amino acids like serine. In this reaction scheme, the enzyme forms an active electrophilic species, the amino-acrylate (FIG. 1C), directly in the active site, which is then intercepted by a nucleophilic substrate. These reactions can be run in aqueous conditions that would hydrolyze the serine-derived lactones or aziridines. Furthermore, the enzyme active site can bind the substrates to accelerate the reaction and control the regioselectivity of nucleophilic substitution.

The ncAA 4-cyanotryptophan (4-CN-Trp) was previously reported to exhibit blue fluorescence ($A_{max}$=405 nm) with a high quantum yield and long lifetime.[15] These properties, among others, make 4-CN-Trp an attractive small-fmolecule fluorophore for imaging studies in vitro and in vivo. However, the chemical synthesis requires multiple steps, including a low-yielding Pd-catalyzed cyanation reaction.

BRIEF SUMMARY OF THE INVENTION

Provided herein are methods for preparing amino acids according to Formula I:

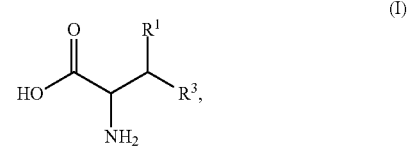

wherein $R^3$ is (A) or (B):

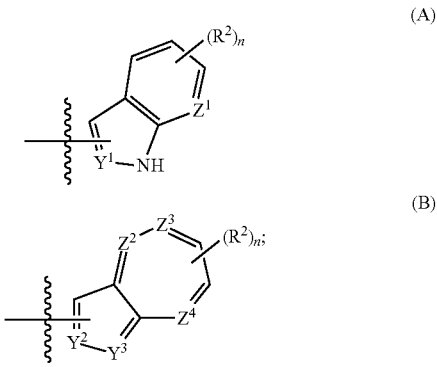

The methods include:
  combining i) an indole substrate or azulene substrate; ii) a serine substrate; and iii) an engineered tryptophan synthase β-subunit (TrpB) in a reaction mixture; and
  maintaining the reaction mixture under conditions sufficient to form the compound according to Formula I,
  wherein the engineered TrpB comprises a PLP binding loop mutation, a helix 1 mutation, a strand 7-8 mutation, or a combination thereof.
For compounds of Formula I:
  $R^1$ is H or $C_{1-8}$ alkyl, which is optionally substituted with one or more $R^{1a}$;
  each $R^{1a}$ is independently selected from the group consisting of halogen, —OH, —CN, —$N_3$, —$NO_2$, $C_{1-12}$ alkyl, $C_{6-14}$ aryl, $C_{2-12}$ alkenyl, $C_{1-12}$ alkynyl, $C_{1-12}$ alkoxy, $C_{7-26}$ arylalkyloxy, $C_{1-12}$ thioalkoxy, —N($R^{1b}$)$_2$, —C(O)$R^{1c}$, —C(O)N($R^{1b}$)$_2$, —N$R^{1b}$C(O)$R^{1c}$, and —OC(O)$R^{1c}$;
  each $R^{1b}$ is independently selected from the group consisting of H and $C_{1-6}$ alkyl;
  each $R^{1c}$ is independently selected from the group consisting of H, —OH, halogen, $C_{1-6}$ alkyl, $C_{1-6}$ alkoxy;
  $Y^1$-$Y^3$ and $Z^1$-$Z^4$ are independently selected from the group consisting of CH, $CR^2$, and N;
  each $R^2$ is independently selected from the group consisting of halogen, —OH, —CN, —$N_3$, —$NO_2$, $C_{1-12}$ alkyl, $C_{6-14}$ aryl, $C_{2-12}$ alkenyl, $C_{1-12}$ alkynyl, $C_{1-12}$ alkoxy, C$_{7-26}$ arylalkyloxy, C$_{1-12}$ thioalkoxy, —N(R$^{2a}$)$_2$, —C(O)R$^{2b}$, —C(O)N(R$^{2a}$)$_2$, —NR$^{2a}$C(O)R$^{2b}$, and —OC(O)R$^{2b}$;

each R$^{2a}$ is independently selected from the group consisting of H and C$_{1-6}$ alkyl;

each R$^{2b}$ is independently selected from the group consisting of H, —OH, halogen, C$_{1-6}$ alkyl, C$_{1-6}$ alkoxy; and subscript n is 0, 1, 2, or 3.

In some embodiments, the engineered TrpB is a thermophilic TrpB such as a *T. maritima* TrpB. In some embodiments, variants of thermophilic TrpBs exhibit enhanced activity at temperatures ranging from 20-50° C.

Also provided herein are new TrpB variants for preparing tryptophan analogs, such as 4-cyanotryptophan, which can be used for the synthesis of pharmaceuticals and natural product derivatives/analogs, and well as tools for chemical biology.

DETAILED DESCRIPTION OF THE INVENTION

Figure 1A:
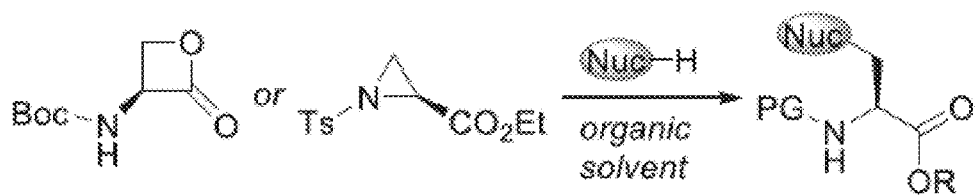
FIG. 1A shows amino acid synthesis by nucleophilic substitution at the β-position according to known methods using preformed lactone or aziridine. Boc, tert-butoxycarbonyl; Ts, 4-toluenesulfonyl; PG, protecting group.
Figure 1B:
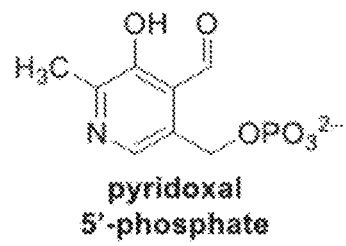
FIG. 1B shows the PLP cofactor used by TrpB enzymes.

Provided herein are improved methods and new materials for the synthesis of tryptophan analogs using engineered variants of the β-subunit of tryptophan synthases (TrpBs) such as *Thermotoga maritima* tryptophan synthase (TmTrpB). Previous work has demonstrated TmTrpB can be engineered to yield tryptophan analogs from L-serine and the corresponding indole analog. However, many tryptophan analogs remain challenging to synthesize, including 4-cyanotryptophan, 4-bromotryptophan, and 5,7-disubstituted tryptophans. Disclosed herein are new enzyme variants including Tm9D8*, which improves the yield of 4-cyanotryptophan and other tryptophan analogs. Further, engineering has shifted the temperature profile of Tm9D8* to allow almost full activity at 37° C., whereas previous variants required 75° C. to achieve full activity.

The enzyme variants Tm9D8 (P19G, E30G, I69V, K96L, P140L, N167D, L213P, G228S, T292S) and Tm9D8* (Tm9D8+I184F) have catalytic activity with substrates including L-serine and 4-cyanoindole, 4-bromoindole, 5-bromo-7-fluoroindole, and 5-chloro-7-iodoindole. Tm9D8 and Tm9D8* have higher activity with these substrates than both the wild-type enzyme and the previously studied variant Tm2F3, which lacks the mutations E30G, I184F, and G228S.

The enzyme variant Tm9D8 produces a maximum yield of 4-cyanotryptophan that is 1.8-fold that of Tm2F3. These mutations also improve the maximum yields of 4-bromotryptophan (1.1-fold), 5-bromo-7-fluorotryptophan (2.8-fold), and 5-chloro-7-iodotryptophan (8.7-fold). The maximum yield of 4-cyanotryptophan with Tm9D8* is 2.9-fold that of Tm2F3. The variant Tm9D8* F184L produces 4-cyanotryptophan with similar improvements in activity.

Tm9D8 and Tm9D8* have a shifted temperature-reactivity profile compared to that of Tm2F3. Specifically, Tm2F3 exhibits maximum activity at reaction temperatures near 75° C., whereas Tm9D8 and Tm9D8* exhibit maximum activity in the range of 37 to 50° C. Tm9D8 and Tm9D8* retain high thermostability (T$_{50}$=88 and 93° C., respectively).

I. DEFINITIONS

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the reagent" includes reference to one or more reagents known to those skilled in the art, and so forth.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The terms "tryptophan synthase β-subunit" and "TrpB" refer to a polypeptide (EC 4.2.1.20) that catalyzes the formation of tryptophan from serine (unsubstituted or substituted) and indole (unsubstituted or substituted). Tryptophan synthases are absent in animals, but they are expressed in a variety of species of plants, eubacteria, archaebacteria, protista, and fungi. The β-subunit catalyzes the condensation of indole and serine to form tryptophan in a PLP-dependent reaction.

The term "indole," by itself or as part of another functional group, refers to 2,3-benzopyrrole and analogs thereof. Unless otherwise specified, substituted indoles can be substituted with one or more moieties selected from halo, hydroxy, amino, alkylamino, alkoxy, arylalkyloxy, haloalkyl, carboxy, amido, nitro, oxo, and cyano.

The term "azulene," by itself or as part of another functional group, refers to bicyclo[5.3.0]decapentaene and analogs thereof. Unless otherwise specified, substituted azulenes can be substituted with one or more moieties selected from halo, hydroxy, amino, alkylamino, arylalkyloxy, alkoxy, haloalkyl, carboxy, amido, nitro, oxo, and cyano.

The term "serine," by itself or as part of another functional group, refers to 2-amino-3-hydroxypropanoic acid. Serines include L-serine ((2S)-2-amino-3-hydroxypropanoic acid) and derivatives thereof, as well as D-serine ((2R)-2-amino-3-hydroxypropanoic acid) and derivatives thereof. In some embodiments, the serine is L-serine or a derivative thereof. The term "3-substituted serine" refers to a 2-amino-3-hydroxypropanoic acid having an alkyl substituent covalently bonded to the 3-carbon (i.e., in the $\beta$ position with respect to the carboxylate functional group). The alkyl substituent can be further substituted as described below.

As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can refer to alkyl groups having up to 20 carbons atoms, such as, but not limited to heptyl, octyl, nonyl, decyl, etc. Alkyl groups can be unsubstituted or substituted. Unless otherwise specified, "substituted alkyl" groups can be substituted with one or more moieties selected from halo, hydroxy, amino, alkylamino, alkoxy, haloalkyl, carboxy, amido, nitro, oxo, and cyano.

As used herein, the term "alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_4$-6, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be unsubstituted or substituted. Unless otherwise specified, "substituted alkenyl" groups can be substituted with one or more moieties selected from halo, hydroxy, amino, alkylamino, alkoxy, haloalkyl, carboxy, amido, nitro, oxo, and cyano.

As used herein, the term "alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be unsubstituted or substituted. Unless otherwise specified, "substituted alkynyl" groups can be substituted with one or more moieties selected from halo, hydroxy, amino, alkylamino, alkoxy, haloalkyl, carboxy, amido, nitro, oxo, and cyano.

As used herein, the term "aryl" refers to an aromatic carbon ring system having any suitable number of ring atoms and any suitable number of rings. Aryl groups can include any suitable number of carbon ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be unsubstituted or substituted. Unless otherwise specified, "substituted aryl" groups can be substituted with one or more moieties selected from halo, hydroxy, amino, alkylamino, alkoxy, haloalkyl, carboxy, amido, nitro, oxo, and cyano.

As used herein, the term "cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, and $C_{6-8}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. Cycloalkyl groups can be unsubstituted or substituted. Unless otherwise specified, "substituted cycloalkyl" groups can be substituted with one or more moieties selected from halo, hydroxy, amino, alkylamino, alkoxy, haloalkyl, carboxy, amido, nitro, oxo, and cyano.

As used herein, the term "heterocyclyl" refers to a saturated ring system having from 3 to 12 ring members and from 1 to 4 heteroatoms selected from N, O and S. Additional heteroatoms including, but not limited to, B, Al, Si and P can also be present in a heterocycloalkyl group. The heteroatoms can be oxidized to form moieties such as, but not limited to, —S(O)— and —S(O)$_2$—. Heterocyclyl groups can include any number of ring atoms, such as, 3 to 6, 4 to 6, 5 to 6, 4 to 6, or 4 to 7 ring members. Any suitable number of heteroatoms can be included in the heterocyclyl groups, such as 1, 2, 3, or 4, or 1 to 2, 1 to 3, 1 to 4, 2 to 3, 2 to 4, or 3 to 4. Examples of heterocyclyl groups include, but are not limited to, aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. Heterocyclyl groups can be unsubstituted or substituted. Unless otherwise specified, "substituted heterocyclyl" groups can be substituted with one or more moieties selected from halo, hydroxy, amino, alkylamino, alkoxy, haloalkyl, carboxy, amido, nitro, oxo, and cyano.

As used herein, the term "alkoxy" refers to an alkyl group having an oxygen atom that connects the alkyl group to the point of attachment: i.e., alkyl-O—. As for alkyl group, alkoxy groups can have any suitable number of carbon atoms, such as $C_{1-6}$ or $C_{1-4}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. Alkoxy groups can be unsubstituted or substituted. Unless otherwise specified, "substituted alkoxy" groups can be substituted with one or more moieties selected from halo, hydroxy, amino, alkylamino, alkoxy, haloalkyl, carboxy, amido, nitro, oxo, and cyano.

As used herein, the terms "halo" and "halogen" refer to fluorine, chlorine, bromine and iodine.

As used herein, the term "haloalkyl" refers to an alkyl moiety as defined above substituted with at least one halogen atom.

As used herein, the term "acyl" refers to a moiety —C(O) R, wherein R is an alkyl group.

As used herein, the term "oxo" refers to an oxygen atom that is double-bonded to a compound (i.e., O=).

As used herein, the term "carboxy" refers to a moiety —C(O)OH. The carboxy moiety can be ionized to form the carboxylate anion. "Alkyl carboxylate" refers to a moiety —C(O)OR, wherein R is an alkyl group as defined herein.

As used herein, the term "amino" refers to a moiety —NR$_3$, wherein each R group is H or alkyl.

As used herein, the term "amido" refers to a moiety —NRC(O)R or —C(O)NR$_2$, wherein each R group is H or alkyl.

As used herein, the term "protecting group" refers to a chemical moiety that renders a functional group such as an amine or carboxylic acid unreactive, but is also removable so as to restore the reactive functional group. Examples of protecting groups include, but are not limited to, benzyloxycarbonyl; 9-fluorenylmethyloxycarbonyl (Fmoc); tert-butyloxycarbonyl (Boc); allyloxycarbonyl (Alloc); p-toluene sulfonyl (Tos); 2,2,5,7,8-pentamethylchroman-6-sulfonyl (Pmc); 2,2,4,6,7-pentamethyl-2,3-dihydrobenzofuran-5-sulfonyl (Pbf); mesityl-2-sulfonyl (Mts); 4-methoxy-2,3,6-trimethylphenylsulfonyl (Mtr); acetamido; phthalimido; and the like. Other protecting groups are known to those of skill in the art including, for example, those described by Green and Wuts (*Protective Groups in Organic Synthesis*, 4$^{th}$ Ed. 2007, Wiley-Interscience, New York).

The terms "protein," "peptide," and "polypeptide" are used interchangeably herein to refer to a polymer of amino acid residues, or an assembly of multiple polymers of amino acid residues. The terms apply to amino acid polymers in which one or more amino acid residues are an artificial chemical mimic of a corresponding naturally occurring amino acid, as well as to naturally occurring amino acid polymers and non-naturally occurring amino acid polymers.

The term "amino acid" includes genetically-encoded α-amino acids and their stereoisomers, as well as other amino acids as described herein, and their stereoisomers. "Stereoisomers" of amino acids refers to mirror image isomers of the amino acids, such as L-amino acids or D-amino acids. For example, a stereoisomer of an L-amino acid refers to the mirror image isomer, i.e., the D-amino acid.

Amino acids include those encoded by the genetic code, as well as those amino acids that are later modified, e.g., hydroxyproline, γ-carboxyglutamate and O-phosphoserine. Genetically encoded α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of genetically-encoded α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Amino acids also include, without limitation, amino acid analogs, amino acid mimetics, synthetic amino acids, N-substituted glycines, and N-methyl amino acids in either the L- or D-configuration that function in a manner similar to the genetically-encoded amino acids. For example, "amino acid analogs" have the same basic chemical structure as genetically encoded amino acids, i.e., an α carbon that is bound to a hydrogen, a carboxyl group, an amino group, but have modified R (i.e., side-chain) groups or modified peptide backbones, e.g., homoserine, norleucine, methionine sulfoxide, methionine methyl sulfonium. "Amino acid mimetics" refer to chemical compounds that have a structure that is different from the general chemical structure of an amino acid, but that functions in a manner similar to a genetically-encoded amino acid.

Amino acids may be referred to herein by either their commonly known three letter symbols or by the one-letter symbols recommended by the IUPAC-IUB Biochemical Nomenclature Commission. For example, an L-amino acid may be represented herein by its commonly known three letter symbol (e.g., Arg for L-arginine) or by an upper-case one-letter amino acid symbol (e.g., R for L-arginine). A D-amino acid may be represented herein by its commonly known three letter symbol (e.g., D-Arg for D-arginine) or by a lower-case one-letter amino acid symbol (e.g., r for D-arginine).

With respect to amino acid sequences, one of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a genetically-encoded amino acid such as an L-amino acid, a stereoisomer of a genetically-encoded amino acid such as a D-amino acid, an amino acid analog, an amino acid mimetic, a synthetic amino acid, an N-substituted glycine, and an N-methyl amino acid.

Conservative substitution tables providing functionally similar amino acids are well known in the art. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains other exemplary amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins,* 1993).

The term "oligonucleotide," "nucleic acid," "nucleotide," or "polynucleotide" refers to deoxyribonucleic acids (DNA) or ribonucleic acids (RNA) and polymers thereof in either single-, double- or multi-stranded form. The term includes, but is not limited to, single-, double- or multi-stranded DNA or RNA, genomic DNA, cDNA, DNA-RNA hybrids, or a polymer comprising purine and/or pyrimidine bases or other natural, chemically modified, biochemically modified, non-natural, synthetic or derivatized nucleotide bases. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), orthologs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991), Ohtsuka et al., *J. Biol. Chem.* 260:2605-2608 (1985), and Rossolini et al., *Mol. Cell. Probes* 8:91-98 (1994)). The term nucleic acid is used interchangeably with gene, cDNA, and mRNA encoded by a gene.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, for example, BLAST and BLAST 2.0 algorithms can be used, which are described in Altschul et al., (1990) *J. Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The BLAST algorithms provide a statistical analysis of the similarity between two sequences (see, e.g., Karlin and Altschul, *Proc. Nat'l. Acad. Sci. USA,* 90: 5873-5787 (1993)). One measure of similarity provided by the BLAST algorithm is the smallest sum probability (P(N)), which provides an indication of the probability by which a match between two nucleotide or amino acid sequences would occur by chance.

The term "site-directed mutagenesis" refers to various methods in which specific changes are intentionally made introduced into a nucleotide sequence (i.e., specific nucleotide changes are introduced at pre-determined locations). Known methods of performing site-directed mutagenesis include, but are not limited to, PCR site-directed mutagenesis, cassette mutagenesis, whole plasmid mutagenesis, and Kunkel's method.

The term "site-saturation mutagenesis," also known as "saturation mutagenesis," refers to a method of introducing random mutations at predetermined locations with a nucleotide sequence, and is a method commonly used in the context of directed evolution (e.g., the optimization of proteins (e.g., in order to enhance activity, stability, and/or stability), metabolic pathways, and genomes). In site-saturation mutagenesis, artificial gene sequences are synthesized using one or more primers that contain degenerate codons; these degenerate codons introduce variability into the position(s) being optimized. Each of the three positions within a degenerate codon encodes a base such as adenine (A), cytosine (C), thymine (T), or guanine (G), or encodes a degenerate position such as K (which can be G or T), M (which can be A or C), R (which can be A or G), S (which can be C or G), W (which can be A or T), Y (which can be C or T), B (which can be C, G, or T), D (which can be A, G, or T), H (which can be A, C, or T), V (which can be A, C, or G), or N (which can be A, C, G, or T). Thus, as a non-limiting example, the degenerate codon NDT encodes an A, C, G, or T at the first position, an A, G, or T at the second position, and a T at the third position. This particular combination of 12 codons represents 12 amino acids (Phe, Leu, Ile, Val, Tyr, His, Asn, Asp, Cys, Arg, Ser, and Gly). As another non-limiting example, the degenerate codon VHG encodes an A, C, or G at the first position, an A, C, or T at the second position, and G at the third position. This particular combination of 9 codons represents 8 amino acids (Lys, Thr, Met, Glu, Pro, Leu, Ala, and Val). As another non-limiting example, the "fully randomized" degenerate codon NNN includes, but is not limited to, all 64 codons for the 20 canonical amino acids.

In some instances, a mixture of degenerate primers is used. A mixture of degenerate primers can contain any number of different degenerate primers in any ratio. As a non-limiting example, a mixture of primers containing the NDT, VHG, and TGG primers can be used. Such a mixture can contain, for example, an amount of each primer in a 12:9:1 ratio (e.g., a NDT:VHG:TGG ratio of 12:9:1). Based on various considerations, non-limiting examples being desired redundancy, the desired presence of stop codons, and/or desired amino acid characteristics (e.g., the presence of nonpolar residues, charged residues, or small side chain residues), different combinations of degenerate primers can be used. Considerations and methods for choosing optimal combinations of degenerate primers will be known to one of skill in the art.

The term "nucleotide sequence encoding a peptide" means the segment of DNA involved in producing a peptide chain. The term can include regions preceding and following the coding region (leader and trailer) involved in the transcription/translation of a gene product and the regulation of the transcription/translation, as well as intervening sequences (introns) between individual coding segments (exons).

The term "homolog," as used herein with respect to an original enzyme or gene of a first family or species, refers to distinct enzymes or genes of a second family or species which are determined by functional, structural or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the function of the protein is similar to the function of the second protein, and/or if the amino acid sequence encoded by a gene has a similar amino acid sequence to that of the second gene. Alternatively, a protein has homology to a second protein if the two proteins have "similar" amino acid sequences. Thus, the term "homologous proteins" is intended to mean that the two proteins have similar amino acid sequences and/or similar functions. In particular embodiments, the homology between two proteins is indicative of its shared ancestry, related by evolution.

II. ENGINEERED TRPB FOR SYNTHESIS OF TRYPTOPHAN DERIVATIVES

Provided herein are methods for preparing compounds according to Formula I:

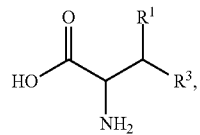

(I)

wherein $R^3$ is (A) or (B):

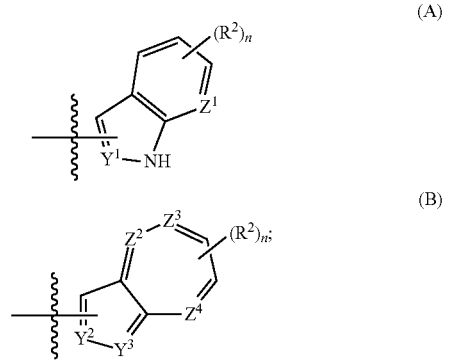

the method comprising:
combining i) an indole substrate or azulene substrate; ii) a serine substrate; and iii) an engineered tryptophan synthase β-subunit (TrpB) in a reaction mixture; and maintaining the reaction mixture under conditions sufficient to form the compound according to Formula I; wherein:
the TrpB comprises a PLP binding loop mutation, a helix 1 mutation, a strand 7-8 mutation, or a combination thereof;
$R^1$ is H or $C_{1-12}$ alkyl, which is optionally substituted with one or more $R^{1a}$;
each $R^{1a}$ is independently selected from the group consisting of halogen, —OH, —CN, —N$_3$, —NO$_2$, $C_{1-12}$ alkyl, $C_{6-14}$ aryl, $C_{2-12}$ alkenyl, $C_{1-12}$ alkynyl, $C_{1-12}$ alkoxy, $C_{1-12}$ thioalkoxy, —N(R$^{1b}$)$_2$, —C(O)R$^{1c}$, —C(O)N(R$^{1b}$)$_2$, —NR$^{1b}$C(O)R$^{1c}$, and —OC(O)R$^{1c}$;
each $R^{1b}$ is independently selected from the group consisting of H and $C_{1-6}$ alkyl;
each $R^{1c}$ is independently selected from the group consisting of H, —OH, halogen, $C_{1-6}$ alkyl, $C_{1-6}$ alkoxy;
$Y^1$-$Y^3$ and $Z^1$-$Z^4$ are independently selected from the group consisting of CH, CR$^2$, and N;
each $R^2$ is independently selected from the group consisting of halogen, —OH, —CN, —N$_3$, —NO$_2$, $C_{1-12}$ alkyl, $C_{6-14}$ aryl, $C_{2-12}$ alkenyl, $C_{1-12}$ alkynyl, $C_{1-12}$ alkoxy, $C_{7-26}$ arylalkyloxy, $C_{1-12}$ thioalkoxy, —N(R$^{2a}$)$_2$, —C(O)R$^{2b}$, —C(O)N(R$^{2a}$)$_2$, —NR$^{2a}$C(O)R$^{2b}$, and —OC(O)R$^{2b}$;
each $R^{2a}$ is independently selected from the group consisting of H and $C_{1-6}$ alkyl;
each $R^{2b}$ is independently selected from the group consisting of H, —OH, halogen, $C_{1-6}$ alkyl, $C_{1-6}$ alkoxy; and
subscript n is 0, 1, 2, or 3.

Tryptophan synthase (TrpS; EC 4.2.1.20) is a heterodimeric complex that catalyzes the formation of L-tryptophan (Trp) from L-serine (Ser) and indole glycerol phosphate (IGP). TrpS is a naturally promiscuous enzyme complex catalyzing 3-substitution reactions with haloindoles, methylindoles, and aminoindoles, along with an assortment of nonindole nucleophiles for C—S and C—N bond formation. Such ncAAs have diverse applications in chemical biology, serve as intermediates in the synthesis of natural products, and are privileged scaffolds for the development of pharmaceuticals.

The catalytic mechanism has been extensively studied for TrpS from *Escherichia coli* and *Salmonella typhimurium*, where it has been shown that the enzyme consists of two subunits, TrpA (α-subunit) and TrpB (β-subunit), both of which have low catalytic efficiencies in isolation. The activities of both subunits increase upon complex formation and are further regulated by an intricate and well-studied allosteric mechanism. IGP binding to the α-subunit stimulates pyridoxal phosphate (PLP)-dependent amino-acrylate formation in the β-subunit [E(A-A)], which in turn promotes retro-aldol cleavage of IGP in the α-subunit, releasing indole. Indole reacts with E(A-A) in a C—C bond-forming reaction, yielding L-tryptophan as product. These allosteric effects are mediated through the rigid-body motion of the communication (COMM) domain and a monovalent cation (MVC) binding site within the β-subunit, which undergo complex conformational transitions associated with open, partially closed, and fully closed states during the catalytic cycle.

Tryptophan synthase is typically found as a linearly arranged bi-enzyme complex. In *S. typhimurium*, the smaller α-subunit (27 kDa) adopts a TIM β/α barrel. The PLP-dependent β-subunit (43 kDa) is of a fold type II conformation and features a monovalent cation-binding site adjacent to its catalytic center. The active sites of the subunits are interconnected by a substrate tunnel for efficient channeling of the common metabolite, indole. A great degree of allosteric regulation by an intricate network of interactions is necessary to synchronize the catalytic activities in the spatially separated active sites of the tryptophan synthase complex. A variety of analytical tools have been employed to gain a more detailed mechanical and chemical understanding of the allosteric regulation mechanisms involved in catalysis, including biochemical solution experiments, mutational studies, and X-ray crystallography. The most essential feature allowing for the high enzymatic efficiency of tryptophan synthase is the direct channeling of the common intermediate, indole, through the hydrophobic 25-Å long substrate tunnel interconnecting the active sites of the subunits. Two alpha subunits and two beta subunits, referred to as TrpA (tryptophan-α) and TrpB (tryptophan-β), form an α-ββ-α complex. There are two main mechanisms for intersubunit communication. First, the COMM domain of the β-subunit and the α-loop2 of the α-subunit interact. Additionally, there are interactions between the αGly181 and βSer178 residues. The active sites are regulated allosterically and undergo transitions between open, inactive, and closed, active, states.

Figure 1C:
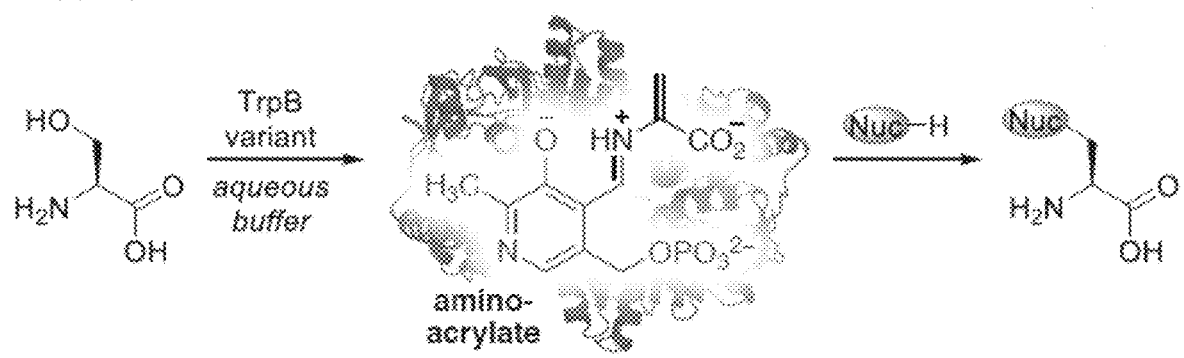
FIG. 1C shows a synthetic route according to the present disclosure in which an enzyme forms an amino-acrylate in situ from stable precursors like serine.
Figure 2A:
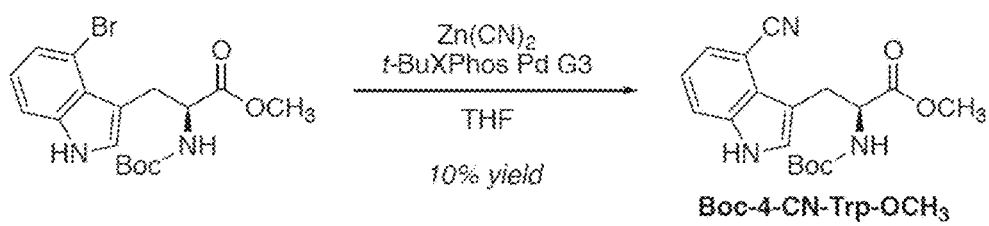
FIG. 2A shows the direct synthesis of 4-cyanotryptophan using a known, palladium-catalyzed route.
Figure 2B:
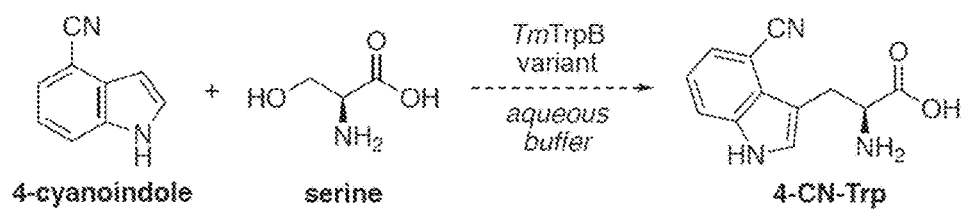
FIG. 2B shows the direct synthesis of 4-cyanotryptophan using new routes according to the present disclosure.

The β-subunit of tryptophan synthase from the thermophilic organism *Pyrococcus furiosus* (PfTrpB) has been engineered as a stand-alone ncAA synthase able to generate tryptophan (Trp) analogs from serine (Ser) and the corresponding substituted indole (FIG. 1C). See, Buller (*Proc. Natl. Acad. Sci. U.S.A.* 112, 14599-14604 (2015)); Romney (*J. Am. Chem. Soc.* 139, 10769-10776 (2017)); Murciano-Calles (*Angew. Chem. Int. Ed.* 55, 11577-11581 (2016). Further engineering of PfTrpB for improved C—C bond formation with indole analogs and threonine (Thr) led to PfTrpB$^{2B9}$ (eight mutations from wild-type PfTrpB), which exhibited a >1,000-fold improvement in (2S, 3S)-β-methyltryptophan (β-MeTrp) production relative to PfTrpB. See, Buller (Biochemistry, 55: 7043-7046 (2016)); Herger (*J. Am. Chem. Soc.*, 138: 8388-8391 (2016)); Boville (*Angew. Chem. Int. Ed.* 57: 14764-14768 (2018)).

TrpB is a PLP-binding protein characterized by "fold type II" that has been described, for example, by Grishin (*Protein Science*, 4: 1291-1304 (1995)) which is incorporated herein by reference in its entirety. Examples of other fold type II PLP-binding proteins include cysteine synthase (EC 4.2.99.8), cystathionine (EC 4.2.1.22), L-serine dehydratase (EC 4.2.1.13), D-serine dehydratase (EC 4.2.1.14), threonine dehydratase (EC 4.2.1.16), threonine synthase (EC 4.2.99.2), 1-aminocyclopropane-1-carboxylate deaminase (EC 4.1.99.4 NA), and alliin lyase (EC 4.4.1.4). TrpBs typically contain an N-terminal domain and a C-terminal domain, approximately equal in size, on either side of a PLP binding site. The cores of the both the N-terminal and C-terminal domains contain a helix/sheet/helix structure, as described by Hyde (*J. Biol. Chem.*, 263: 17857-17871 (19880) and Ro (*J. Biol. Chem.*, 274: 36439-36445 (1999)), which are incorporated herein by reference in their entirety.

The PLP-binding sites in TrpB include a lysine (Lys82 in *P. furiosis*, between helix 4 and helix 5) near the N-terminus which forms a Schiff base with PLP and a binding loop nearer to the C-terminus (positions 227-300 in *P. furiosis*) that interacts with the PLP phosphate group. A so-called "COMM domain" (residues 95-161 in *P. furiosis*, containing a portion of helix 5; strand 4; helix 6; strand 5; helix 7; helix 8; strand 6; and a portion of helix 9) provides communication between the α- and β-subunits of TrpS. The COMM domain enters a partially closed conformation and fully closed conformation during the enzyme's catalytic cycle.

Structural features of TrpBs, including those described above, can be readily identified in TrpB based on the primary amino acid sequence of a particular TrpB, homology modeling, inspection of crystallographic structures, or a combination thereof. In *T. maritima* TrpB, for example, the Schiff base lysine occurs at position 83, the phosphate binding loop occurs at positions 228-231, and the COMM domain resides at positions 96-162.

The methods of the present disclosure are based, in part, on the discovery that mutation of residues in the PLP binding loop of TrpB can allow for reorganization of the binding site and improved accommodation of substituted indole substrates, e.g., 4-substituted indoles such as 4-cyanoindole, and azulene substrates. TrpBs from mesophilic organisms and thermophilic organisms can be engineered in this manner. Surprisingly, variants of thermophilic enzymes were also found to exhibit high activity at temperatures ranging from 20-50° C. (e.g., 25° C. or 37° C.). This shifted temperature profile is advantageous because it provides for simplified development and manufacturing methods, as well as for the use of substrates that would be unstable in water at elevated temperatures. As such, TrpBs from thermophilic organisms can be engineered according to the present disclosure so as to obtain engineered enzymes with a shifted temperature/activity profile. Examples of thermophilic TrpBs that can serve as engineering templates include, but are not limited to, a *T. maritima* TrpB, a *P. furiosis* TrpB, an *A. fulgidus* TrpB, a *T. naphthophila* TrpB, a *T. petrophila* TrpB, a *T. neapolitana* TrpB, a *C. subterraneus* TrpB, a *D. tunisiensi* TrpB, a *D. kuznetsovii* TrpB, a *P. mobilis* TrpB, an *A. aeolicus* TrpB, an *S. azorense* TrpB, a *T. pseudethanolicus* TrpB, a *T. thermophilus* TrpB, a *P. abyssi* TrpB, an *M. jannaschii* TrpB, a *T. kodakarensis* TrpB, and an *M. aeolicus* TrpB. Examples of mesophilic TrpBs that can serve as engineering templates include, but are not limited to, an *S. typhimurium* TrpB, a *C. acetobutylicum* TrpB, an *L. pneumophila* TrpB, and an *E. coli* TrpB.

In some embodiments, the mutation in the PLP binding loop in the engineered TrpB is a mutation of a residue corresponding to any one of residues G227, G228, G229, and S230 in a *T. maritima* TrpB. The native residue at any of these positions can be mutated, for example, to Ala, Asp, Arg, Asn, Cys, Glu, Gln, Gly, His, Ile, Lys, Leu, Met, Phe, Pro, Ser, Thr, Trp, Tyr, or Val. In some embodiments, the mutation is made in a particular TrpB sequence at the residue corresponding to G228 in a *T. maritima* TrpB (TmTrpB G228). The mutation at the position corresponding to TmTrpB G228 can be, for example, a mutation of the native residue to Ser, Thr, Gin, Asn, His, or Tyr.

In some embodiments, the engineered TrpB comprises a polypeptide having at least 60% identity, at least 65% identity, at least 70% identity, at least 75% identity, at least 80% identity, at least 85% identity, at least 90% identity, or at least 95% identity to SEQ ID NO: 1, and one or mutations at positions corresponding to G227, G228, G229, and S230.

In some embodiments, the engineered TrpB comprises a polypeptide having at least 60% identity, at least 65% identity, at least 70% identity, at least 75% identity, at least 80% identity, at least 85% identity, at least 90% identity, or at least 95% identity to SEQ ID NO: 1, and a mutation corresponding to G228S.

In some embodiments, the engineered TrpB is a *T. maritima* TrpB comprising a polypeptide according to SEQ ID NO: 1, and one or mutations at residues selected from G227, G228, G229, and S230. In some embodiments, the engineered TrpB is a *T. maritima* TrpB comprising a polypeptide according to SEQ ID NO: 1 and a G228S mutation.

In some embodiments, the helix 1 mutation in the engineered TrpB is a mutation of a residue corresponding to any one of residues 15-31 in a *T. maritima* TrpB. In some embodiments, the helix 1 mutation is made at a position corresponding to a residue in helix 1 of *P. furiosis* TrpB (positions 13-29 in SEQ ID NO:2). In some embodiments, the helix 1 mutation is made in a particular TrpB sequence at the residue corresponding to E30 in a *T. maritima* TrpB (TmTrpB G228). The helix 1 mutation at the position corresponding to TmTrpB E30 can be, for example, a mutation of the native residue to Gly, Ala, Val, or Pro. In some embodiments, the strand 7-8 mutation in the engineered TrpB is a mutation of a residue corresponding to any one of residues 180-187 in a *T. maritima* TrpB. In some embodiments, the strand 7-8 mutation is made at a position corresponding to a residue in strand 7, in strand 8, or in the loop connecting strands 7 and 8 in *P. furiosis* TrpB (positions 179-186 in SEQ ID NO:2). In some embodiments, the strand 7-8 mutation is made at the residue corresponding to TmTrpB I184. The strand 7-8 mutation at the position corresponding to TmTrpB I184 can be, for example, a mutation of the native residue to Phe, Trp, or Tyr. In some embodiments, the strand 7-8 mutation at the position corresponding to TmTrpB I184 is a mutation of the native residue to Lys.

In some embodiments, the engineered TrpB comprises a polypeptide having at least 60% identity, at least 65% identity, at least 70% identity, at least 75% identity, at least 80% identity, at least 85% identity, at least 90% identity, or at least 95% identity to SEQ ID NO: 1, and a helix 1 mutation.

In some embodiments, the engineered TrpB comprises a polypeptide having at least 60% identity, at least 65% identity, at least 70% identity, at least 75% identity, at least 80% identity, at least 85% identity, at least 90% identity, or at least 95% identity to SEQ ID NO: 1, and a strand 7-8 mutation.

In some embodiments, the engineered TrpB comprises a polypeptide having at least 60% identity, at least 65% identity, at least 70% identity, at least 75% identity, at least 80% identity, at least 85% identity, at least 90% identity, or at least 95% identity to SEQ ID NO: 1, and one or mutations at positions corresponding to E30 or I184.

In some embodiments, the engineered TrpB comprises a polypeptide having at least 60% identity, at least 65% identity, at least 70% identity, at least 75% identity, at least 80% identity, at least 85% identity, at least 90% identity, or at least 95% identity to SEQ ID NO: 1, and one or mutations at corresponding to E30 or I184F.

In some embodiments, the engineered TrpB is a *T. maritima* TrpB comprising a polypeptide according to SEQ ID NO: 1, a G228S mutation, and an E30G mutation or an I184F mutation. In some embodiments, the engineered TrpB is a *T. maritima* TrpB comprising a polypeptide according to SEQ ID NO: 1, a G228S mutation, an E30G mutation, and an I184F mutation.

In some embodiments, the engineered TrpB further comprises one or more additional helix 1 mutations. In some embodiments, the helix 1 mutation corresponds to E17 in SEQ ID NO:2. In some embodiments, the helix 1 mutation corresponds to P19 in SEQ ID NO:1. In some embodiments, the helix 1 mutation is a mutation of the native residue to Gly, Ala, Val, or Pro. In some embodiments, the helix 1 mutation is a mutation of the native residue to Gly.

In some embodiments, the engineered TrpB further comprises a mutation in a beta strand of a particular TrpB sequence corresponding to strand 3 of *P. furiosis* TrpB (a "strand 3 mutation") corresponding to positions 65-71 in SEQ ID NO:2. In some embodiments, the strand 3 mutation corresponds to I69 in SEQ ID NO:2. In some embodiments, the strand 3 mutation corresponds to I68 in SEQ ID NO: 1. In some embodiments, the strand 3 mutation is a mutation of the native residue to Val, Leu, or Met. In some embodiments, the strand 3 mutation is a mutation of the native residue to Val.

In some embodiments, the engineered TrpB further comprises a mutation in an alpha helix of a particular TrpB sequence corresponding to helix 9 of *P. furiosis* TrpB (a "helix 9 mutation") corresponding to positions 161-175 in SEQ ID NO:2. In some embodiments, the helix 9 mutation corresponds to N167 in SEQ ID NO:2. In some embodiments, the helix 9 mutation corresponds to N166 in SEQ ID NO:1. In some embodiments, the helix 9 mutation is a mutation of the native residue to Asp or Glu. In some embodiments, the helix 9 mutation is a mutation of the native residue to Asp.

In some embodiments, the engineered TrpB further contains a "strand 13-14" mutation near the monovalent cation binding site, at a position corresponding to a residue in strand 13, in strand 14, or in the loop connecting strands 13 and 14 (e.g., between positions 281-296 in SEQ ID NO:1). In some embodiments, the strand 13-14 mutation modulates hydrogen bonding networks that affect the active site and accommodation of substituted indoles. In some embodiments, the engineered TrpB further comprises a mutation at a residue corresponding to T292 in SEQ ID NO:1 or SEQ ID NO:2. The mutation can be, for example, a mutation of the native residue to Ser, Thr, Gln, Asn, His, or Tyr. In some embodiments, the mutation corresponding to T292 in SEQ ID NO:2 or SEQ ID NO:2 is a mutation of the native residue to Ser.

In some embodiments, the engineered TrpB further comprises one or more mutations in a particular TrpB at positions corresponding to TmTrpB P19, I69, N167, and T292.

In some embodiments, the engineered TrpB comprises a polypeptide comprises a polypeptide having at least 60% identity, at least 65% identity, at least 70% identity, at least 75% identity, at least 80% identity, at least 85% identity, at least 90% identity, or at least 95% identity to SEQ ID NO: 1, and mutations at one more positions corresponding P19, E30, I69, K96, P140, N167, I184, L213, G228, or T292. In some embodiments, the polypeptide has mutations each position corresponding to P19, E30, I69, K96, P140, N167, I184, L213, G228, and T292.

In some embodiments, the engineered TrpB comprises a polypeptide comprises a polypeptide having at least 60% identity, at least 65% identity, at least 70% identity, at least 75% identity, at least 80% identity, at least 85% identity, at least 90% identity, or at least 95% identity to SEQ ID NO:1, and mutations corresponding to P19G, E30G, I69V, K96L, P140L, N167D, I184F, L213P, G228S, and T292S.

In some embodiments, the engineered TrpB further comprises one or more mutations corresponding to positions 2, 4, 5, 10, 11, 12, 13, 16, 20, 21, 35, 36, 41, 59, 67, 89, 95, 123, 127, 144, 146, 150, 178, 180, 181, 182, 220, 233, 267, 272, 274, 284, 321, 323, and 384 in SEQ ID NO:2.

In some embodiments, the engineered TrpB further comprises one or more mutations corresponding to positions 4, 6, 7, 12, 13, 14, 15, 18, 22, 23, 37, 38, 43, 61, 68, 90, 96, 124, 128, 145, 147, 151, 179, 181, 182, 183, 221, 234, 267, 272, 274, 284, 321, 323, and 381 in SEQ ID NO:1.

In some embodiments, the engineered TrpB is designated Tm9D8 and has the amino acid sequence set forth in SEQ ID NO:3. In some embodiments, the engineered TrpB is designated Tm9D8* and has the amino acid sequence set forth in SEQ ID NO:4.

Mutational methods of generating diversity include, for example, site-directed mutagenesis (Ling et al. (1997) *Anal Biochem.* 254(2): 157-178; Dale et al. (1996)*Methods Mol. Biol.* 57:369-374; Smith (1985) *Ann. Rev. Genet.* 19:423-462; Botstein & Shortle (1985) *Science* 229:1193-1201; Carter (1986) *Biochem. J.* 237:1-7; and Kunkel (1987) in *Nucleic Acids & Molecular Biology* (Eckstein, F. and Lilley, D. M. J. eds., Springer Verlag, Berlin)); mutagenesis using uracil containing templates (Kunkel (1985) *Proc. Natl. Acad. Sci. USA* 82:488-492; Kunkel et al. (1987) *Methods in Enzymol.* 154, 367-382; and Bass et al. (1988) *Science* 242:240-245); oligonucleotide-directed mutagenesis (*Methods in Enzymol.* 100: 468-500 (1983); *Methods in Enzymol.*

154: 329-350 (1987); Zoller & Smith (1982) *Nucleic Acids Res.* 10:6487-6500; Zoller & Smith (1983) *Methods in Enzymol.* 100:468-500; and Zoller & Smith (1987) *Methods in Enzymol.* 154:329-350); phosphorothioate-modified DNA mutagenesis (Taylor et al. (1985) *Nucl. Acids Res.* 13: 8749-8764; Taylor et al. (1985) *Nucl. Acids Res.* 13: 8765-8787; Nakamaye & Eckstein (1986) *Nucl. Acids Res.* 14: 9679-9698; Sayers et al. (1988) *Nucl. Acids Res.* 16:791-802; and Sayers et al. (1988) *Nucl. Acids Res.* 16: 803-814); mutagenesis using gapped duplex DNA (Kramer et al. (1984) *Nucl. Acids Res.* 12: 9441-9456; Kramer & Fritz (1987) *Methods in Enzymol.* 154:350-367; Kramer et al. (1988) *Nucl. Acids Res.* 16: 7207; and Fritz et al. (1988) *Nucl. Acids Res.* 16: 6987-6999).

Additional suitable methods include point mismatch repair (Kramer et al. (1984) *Cell* 38:879-887), mutagenesis using repair-deficient host strains (Carter et al. (1985) *Nucl. Acids Res.* 13: 4431-4443; and Carter (1987) *Methods in Enzymol.* 154: 382-403), deletion mutagenesis (Eghtedarzadeh & Henikoff (1986) *Nucl. Acids Res.* 14: 5115), restriction-selection and restriction-purification (Wells et al. (1986) *Phil. Trans. R. Soc. Lond. A* 317: 415-423), mutagenesis by total gene synthesis (Nambiar et al. (1984) *Science* 223: 1299-1301; Sakamar and Khorana (1988) *Nucl. Acids Res.* 14: 6361-6372; Wells et al. (1985) *Gene* 34:315-323; and Grundstrom et al. (1985) *Nucl. Acids Res.* 13: 3305-3316); double-strand break repair (Mandecki (1986); Arnold (1993) *Current Opinion in Biotechnology* 4:450-455; and *Proc. Natl. Acad. Sci. USA*, 83:7177-7181).

Additional details regarding various diversity generating methods can be found in the following U.S. patents, PCT publications, and EPO publications: U.S. Pat. No. 5,605,793 to Stemmer (Feb. 25, 1997), U.S. Pat. No. 5,811,238 to Stemmer et al. (Sep. 22, 1998) U.S. Pat. No. 5,830,721 to Stemmer et al. (Nov. 3, 1998), U.S. Pat. No. 5,834,252 to Stemmer, et al. (Nov. 10, 1998) U.S. Pat. No. 5,837,458 to Minshull, et a. (Nov. 17, 1998), WO 95/22625, Stemmer and Crameri, WO 96/33207 by Stemmer and Lipschutz, WO 97/20078 by Stemmer and Crameri; WO 97/35966 by Minshull and Stemmer, WO 99/41402 by Punnonen et al., WO 99/41383 by Punnonen et al., WO 99/41369 by Punnonen et al., WO 99/41368 by Punnonen et al., EP 752008 by Stemmer and Crameri, EP 0932670 by Stemmer, WO 99/23107 by Stemmer et al., WO 99/21979 by Apt et al., WO 98/31837 by del Cardayre et al., WO 98/27230 by Patten and Stemmer, WO 98/13487 by Stemmer et al., WO 00/00632, WO 00/09679, WO 98/42832 by Arnold et al., WO 99/29902 by Arnold et al., WO 98/41653 by Vind, WO 98/41622 by Borchert et al., WO 98/42727 by Pati and Zarling, WO 00/18906 by Patten et al., WO 00/04190 by del Cardayre et al., WO 00/42561 by Crameri et al., WO 00/42559 by Selifonov and Stemmer, WO 00/42560 by Selifonov et al., WO 01/23401 by Welch et al., and WO 01/64864 by Affholter.

Engineered TrpBs can include additional mutations, including but not limited to amino acid mutations that promote the formation and/or persistence of the amino-acrylate intermediate in the TrpB catalytic cycle. As used herein, the terms "amino-acrylate intermediate" and "E(A-A) intermediate" refer to a 4-substituted (E)-2-(((E)-(2-methyl-3-oxido-5-((phosphonooxy)-methyl)pyridin-4-yl) methylene)ammonio)but-2-enoate species according to Formula A-A:

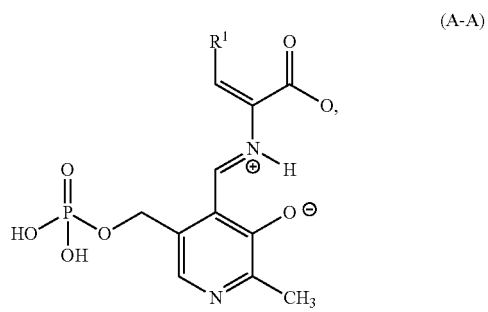

(A-A)

wherein $R^1$ is $C_{2-8}$ alkyl, which is optionally substituted with one or more $R^{1a}$ as described above. One of skill in the art will appreciate that the amino-acrylate intermediate can exist in different tautomeric forms, where the ionizable functional groups (i.e., carboxylate, phosphate, phenolate, iminium) are protonated or deprotonated.

The effects of a particular mutation can be assessed spectroscopically as described in detail below. For example, incubation of TrpB with a serine substrate leads to formation of the amino-acrylate intermediate and a detectable absorbance at 350 nm. Hydrolysis of the amino-acrylate intermediate can result in a partial or complete loss of the absorbance at 350 nm. Deamination of the hydrolyzed amino-acrylate, in turn, results in the formation of an α-keto acid having a distinct, detectable absorbance at 320 nm. Accordingly, the effects of a particular mutation in promoting product formation (e.g., via formation of the amino-acrylate intermediate and/or its persistence during the TrpB catalytic cycle) can be readily determined by assessing the absorbance spectrum of a mixture containing the TrpB and the serine substrate. This can include measuring the absorbance at 350 nm (e.g., observing an increase in absorbance at 350 nm) and/or measuring the absorbance at 320 nm (e.g., finding that the absorbance at 320 nm does not increase with time).

In some embodiments, the TrpB comprises an amino acid sequence that has about 55% or greater (e.g., about 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) identity to any of the amino acid sequences described herein (e.g., the amino acid sequences set forth in SEQ ID NO:3 and SEQ ID NO:4), provided that the TrpB contains at least one PLP binding loop mutation, helix 1 mutation, or strand 7-8 mutation as described above. In some embodiments, the TrpB comprises an amino acid sequence that has about 70% or greater (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) identity to any of the amino acid sequences described herein. In some embodiments, the TrpB comprises an amino acid sequence that has about 80% or greater (e.g., about 80%, 81%, 82%, 83%, 84%, 85%, 86%, 87%, 88%, 89%, 90%, 91%, 92%, 93%, 94%, 95%, 96%, 97%, 98%, 99%, or 100%) identity to any of the amino acid sequences described herein. In some embodiments, the TrpB comprises an amino acid sequence that has about 90% or greater (e.g., about 90%, 91%, 92%, 93%, 94%, 95%, 96%, 97%, 98%, 99%, or 100%) identity any of the amino acid sequences described herein. In some instances, the TrpB comprises an amino acid sequence that is about 95%, 96%, 97%, 98%, 99%, or 100% identical to any of the amino acid sequences described herein. The engineered TrpBs described herein can be used with or without N-terminal methionine residues (e.g., with or without the N-terminal methionine residues set forth in SEQ ID NOS: 1-26).

Tryptophan synthases from other organisms can be engineered with mutations as described above, at the amino acid positions corresponding to the analogous sites in *T. maritima* and/or *P. furiosus*. TrpBs from *A. fulgidus* (SEQ ID NO:5) or *E. coli* (SEQ ID NO:6), for example, can also be engineered for synthesis of tryptophan analogs. The TrpB can be an *S. typhimurium* TrpB (UniProt Accession No. P0A2K1; SEQ ID NO:7), a *T. naphthophila* TrpB (e.g., UniProt Accession No. D2C7C6; SEQ ID NO:8), a *T. petrophila* TrpB (e.g., UniProt Accession No. A5IKT3; SEQ ID NO:9), a *T. neapolitana* TrpB (e.g., UniProt Accession No. B9K6Z5; SEQ ID NO: 10), a *C. subterraneus* TrpB (e.g., UniProt Accession No. Q8R9M9; SEQ ID NO:11 or UniProt Accession No. A0A101E5G9; SEQ ID NO: 12), a *D. tunisiensi* TrpB (e.g., UniProt Accession No. A0A0C7P286; SEQ ID NO: 13), a *D. kuznetsovii* TrpB (e.g., UniProt Accession No. F6CML8; SEQ ID NO: 14), a *P. mobilis* TrpB (e.g., UniProt Accession No. A9BHQ3; SEQ ID NO:15), an *A. aeolicus* TrpB (e.g., UniProt Accession No. 066923; SEQ ID NO: 16), an *S. azorense* TrpB (e.g., UniProt Accession No. C1DUP2; SEQ ID NO:17), a *T. pseudethanolicus* TrpB (e.g., UniProt Accession No. B0K8T6; SEQ ID NO:18), a *T. thermophilus* TrpB (e.g., UniProt Accession No. P16609; SEQ ID NO: 19 or UniProt Accession No. F6DH06; SEQ ID NO:20), a *C. acetobutylicum* TrpB (e.g., UniProt Accession No. Q97EF5; SEQ ID NO:21), an *L. pneumophila* TrpB (e.g., UniProt Accession No. A5IBF7; SEQ ID NO:22), a *P. abyssi* TrpB (e.g., UniProt Accession No. Q9V1G8; SEQ ID NO:23), an *M. jannaschii* TrpB (e.g., UniProt Accession No. Q60179; SEQ ID NO:24), a *T. kodakarensis* TrpB (e.g., UniProt Accession No. Q9YGB0; SEQ ID NO:25), or an *M. aeolicus* TrpB (e.g., UniProt Accession No. A6UW25; SEQ ID NO:26).

The TrpB can be an *A. cryptum* TrpB (e.g., UniProt Accession No. A5FY57), an *A. ferrooxidans* TrpB (e.g., UniProt Accession No. B7J4S9), an *A. citrulli* TrpB (e.g., UniProt Accession No. A1TLG8), an *A. baylyi* TrpB (e.g., UniProt Accession No. Q6FEF 1), an *A. pleuropneumoniae* TrpB (e.g., UniProt Accession No. B0BU72), an *A. succinogenes* TrpB (e.g., UniProt Accession No. A6VPD9), an *A. hydrophila* TrpB (e.g., UniProt Accession No. A0KMD0), an *A. salmonicida* TrpB (e.g., UniProt Accession No. A4SKT1), an *A. fabrum* TrpB (e.g., UniProt Accession No. Q8UJB0), an *A. radiobacter* TrpB (e.g., UniProt Accession No. B9JG43), an *A. vitis* TrpB (e.g., UniProt Accession No. B9JXV6), an *A. salmonicida* TrpB (e.g., UniProt Accession No. B6EJA3), an *A. metalliredigens* TrpB (e.g., UniProt Accession No. A6TM76), an *A. mediterranea* TrpB (e.g., UniProt Accession No. B4S1J4), an *A. variabilis* TrpB (e.g., UniProt Accession No. Q3MBV3), an *A. flavithermus* TrpB (e.g., UniProt Accession No. B7GHQ9), an *A. pseudotrichonymphae* TrpB (e.g., UniProt Accession No. B6YQ32), an *A. vinelandii* TrpB (e.g., UniProt Accession No. C1DH66), a *B. anthracis* TrpB (e.g., UniProt Accession No. Q81TL8), a *B. cereus* TrpB (e.g., UniProt Accession No. C1ELF0), a *B. clausii* TrpB (e.g., UniProt Accession No. Q5WGS1), a *B. halodurans* TrpB (e.g., UniProt Accession No. Q9KCB0), a *B. licheniformis* TrpB (e.g., UniProt Accession No. Q65135), a *B. pumilus* TrpB (e.g., UniProt Accession No. A8FEJ8), a *B. subtilis* TrpB (e.g., UniProt Accession No. P07600), a *B. thuringiensis* TrpB (e.g., UniProt Accession No. A0RB64), a *B. velezensis* TrpB (e.g., UniProt Accession No. A7Z616), a *B. weihenstephanensis* TrpB (e.g., UniProt Accession No. A9VJW2), a *B. fragilis* TrpB (e.g., UniProt Accession No. Q5LBZ8), a *B. thetaiotaomicron* TrpB (e.g., UniProt Accession No. Q8AAD2), a *B. vulgatus* TrpB (e.g., UniProt Accession No. A6L7M5), a *B. indica* TrpB (e.g., UniProt Accession No. B2IF48), a *B. floridanus* TrpB (e.g., UniProt Accession No. Q7VR00), a *B. pennsylvanicus* TrpB (e.g., UniProt Accession No. Q492N6), a *B. bronchiseptica* TrpB (e.g., UniProt Accession No. Q7WD04), a *B. parapertussis* TrpB (e.g., UniProt Accession No. Q7W5G8), a *B. pertussis* TrpB (e.g., UniProt Accession No. Q7VTF 1), a *B. petrii* TrpB (e.g., UniProt Accession No. A9IIE0), a *B. diazoefficiens* TrpB (e.g., UniProt Accession No. Q89WE5), a *B. abortus* TrpB (e.g., UniProt Accession No. Q2YQW5), a *B. canis* TrpB (e.g., UniProt Accession No. A9M9U2), a *B. melitensis* TrpB (e.g., UniProt Accession No. Q8YE60), a *B. suis* TrpB (e.g., UniProt Accession No. B0CJK8), a *B. aphidicola* TrpB (e.g., UniProt Accession No. Q44685), a *C. jejuni* TrpB (e.g., UniProt Accession No. Q5HWB9), a *C. vibrioides* TrpB (e.g., UniProt Accession No. P12290), a *C. trachomatis* TrpB (e.g., UniProt Accession No. 084172), a *C. tepidum* TrpB (e.g., UniProt Accession No. Q8KF 11), a *C. violaceum* TrpB (e.g., UniProt Accession No. Q7NUD8), a *C. koseri* TrpB (e.g., UniProt Accession No. A8AG61), a *C. michiganensis* TrpB (e.g., UniProt Accession No. A5CRV6), a *C. beijerinckii* TrpB (e.g., UniProt Accession No. A6LU96), a *C. botulinum* TrpB (e.g., UniProt Accession No. B2V2T4), a *C. kluyveri* TrpB (e.g., UniProt Accession No. A5N7P0), a *C. novyi* TrpB (e.g., UniProt Accession No. A0PYH3), a *C. glutamicum* TrpB (e.g., UniProt Accession No. P06561), a *C. sakazakii* TrpB (e.g., UniProt Accession No. A7MMG1), a *D. aromatica* TrpB (e.g., UniProt Accession No. Q47HQ5), a *D. radiodurans* TrpB (e.g., UniProt Accession No. Q9RVT 1), a *D. amylolyticus* TrpB (e.g., UniProt Accession No. B8D4P0), a *D. shibae* TrpB (e.g., UniProt Accession No. A8LSF9), an *E. ictaluri* TrpB (e.g., UniProt Accession No. C5BDB7), an *E. minutum* TrpB (e.g., UniProt Accession No. B2KCI5), an *E. tasmaniensis* TrpB (e.g., UniProt Accession No. B2VKT2), an *E. fergusonii* TrpB (e.g., UniProt Accession No. B7LS 19), an *E. sibiricum* TrpB (e.g., UniProt Accession No. B 1YLS4), an *F. nodosum* TrpB (e.g., UniProt Accession No. A7HMG8), an *F. philomiragia* TrpB (e.g., UniProt Accession No. B0TWI3), an *F. tularensis* TrpB (e.g., UniProt Accession No. A7N9D2), an *F. nucleatum* TrpB (e.g., UniProt Accession No. Q8RGH8), an *G. stearothermophilus* TrpB (e.g., UniProt Accession No. P19868), an *G. thermodenitrificans* TrpB (e.g., UniProt Accession No. A4IQ82), an *G. violaceus* TrpB (e.g., UniProt Accession No. Q7NGX9), an *H. influenzae* TrpB (e.g., UniProt Accession No. Q4QKF5), an *H. hepaticus* TrpB (e.g., UniProt Accession No. Q7VGA7), an *H. pylori* TrpB (e.g., UniProt Accession No. P56142), an *H. somni* TrpB (e.g., UniProt Accession No. B0UU34), a *K. pneumoniae* TrpB (e.g., UniProt Accession No. B5XT02), a *K. versatilis* TrpB (e.g., UniProt Accession No. Q1ISI9), an *L. casei* TrpB (e.g., UniProt Accession No. P17167), an *L. casei* TrpB (e.g., UniProt Accession No. B3W6W6), an *L. paracasei* TrpB (e.g., UniProt Accession No. Q03CY3), an *L. plantarum* TrpB (e.g., UniProt Accession No. Q88WI0), an *L. lactis* TrpB (e.g., UniProt Accession No. A2RK24), an *L. xyli* TrpB (e.g., UniProt Accession No. Q6AF67), an *L. biflexa* TrpB (e.g., UniProt Accession No. B0SDM8), an *L. borgpetersenii* TrpB (e.g., UniProt Accession No. Q04U63), an *L. interrogans* TrpB (e.g., UniProt Accession No. Q72U05), an *L. cholodnii* TrpB (e.g., UniProt Accession No. B1XY48), an *L. innocua* TrpB (e.g., UniProt Accession No. Q92B81), an *L. monocytogenes* TrpB (e.g., UniProt Accession No. B8DHB4), an *L. welshimeri* TrpB (e.g., UniProt Accession No. A0AJ80), an *M. succiniciproducens* TrpB (e.g., UniProt Accession No. Q65TF0), an *M. voltae* TrpB (e.g., UniProt Accession No. P14638), an *M. labreanum* TrpB (e.g., UniProt Accession No. A2STA4), an *M. kandleri* TrpB (e.g., UniProt Accession No. Q8TX91), an *M. petroleiphilum* TrpB (e.g., UniProt Accession No. A2SHS4), an *M. flagellatus* TrpB (e.g., UniProt Accession No. Q1H0M1), an *M. extorquens* TrpB (e.g., UniProt Accession No. B7L1H4), an *M. nodulans* TrpB (e.g., UniProt Accession No. B819V8), an *M. populi* TrpB (e.g., UniProt Accession No. B 1ZG57), an *M. radiotolerans* TrpB (e.g., UniProt Accession No. B1LSI6), an *M. capsulatus* TrpB (e.g., UniProt Accession No. Q604P3), an *M. bovis* TrpB (e.g., UniProt Accession No. P66985), an *M. intracellulare* TrpB (e.g., UniProt Accession No. O68905), an *M. leprae* TrpB (e.g., UniProt Accession No. Q9CC54), an *M. tuberculosis* TrpB (e.g., UniProt Accession No. P9WFX9), an *N. gonorrhoeae* TrpB (e.g., UniProt Accession No. Q84GJ9), an *N. meningitidis* TrpB (e.g., UniProt Accession No. Q9JVC0), an *N. europaea* TrpB (e.g., UniProt Accession No. Q82WI2), an *N. multiformis* TrpB (e.g., UniProt Accession No. Q2Y7R4), an *N. aromaticivorans* TrpB (e.g., UniProt Accession No. Q2G8S7), an *O. iheyensis* TrpB (e.g., UniProt Accession No. Q8ESU4), an *O. anthropi* TrpB (e.g., UniProt Accession No. A6WX28), an *O. carboxidovorans* TrpB (e.g., UniProt Accession No. B6JCP2), a *P. distasonis* TrpB (e.g., UniProt Accession No. A6L9K4), a *P. denitrificans* TrpB (e.g., UniProt Accession No. A1B8L3), a *P. lavamentivorans* TrpB (e.g., UniProt Accession No. A7HPD3), a *P. multocida* TrpB (e.g., UniProt Accession No. P54203), a *P. atrosepticum* TrpB (e.g., UniProt Accession No. Q6D4U0), a *P. carotovorum* TrpB (e.g., UniProt Accession No. C6DGZ5), a *P. zucineum* TrpB (e.g., UniProt Accession No. B4RCL0), a *P. profundum* TrpB (e.g., UniProt Accession No. Q6LPA4), a *P. luminescens* TrpB (e.g., UniProt Accession No. Q7N486), a *P. torridus* TrpB (e.g., UniProt Accession No. Q6L271), a *P. naphthalenivorans* TrpB (e.g., UniProt Accession No. A1VRR7), a *P. marinus* TrpB (e.g., UniProt Accession No. A2BNV9), a *P. atlantica* TrpB (e.g., UniProt Accession No. Q15RZ5), a *P. aeruginosa* TrpB (e.g., UniProt Accession No. P07345), a *P. entomophila* TrpB (e.g., UniProt Accession No. Q1IH20), a *P. fluorescens* TrpB (e.g., UniProt Accession No. Q4KKP4), a *P. putida* TrpB (e.g., UniProt Accession No. P11080), a *P. savastanoi* TrpB (e.g., UniProt Accession No. Q849P2), a *P. syringae* TrpB (e.g., UniProt Accession No. P34817), a *P. lettingae* TrpB (e.g., UniProt Accession No. A8F8F7), a *P. ingrahamii* TrpB (e.g., UniProt Accession No. A1STT0), a *P. aerophilum* TrpB (e.g., UniProt Accession No. Q8ZV44), a *P. arsenaticum* TrpB (e.g., UniProt Accession No. A4WKQ9), a *P. islandicum* TrpB (e.g., UniProt Accession No. A1RVT1), a *P. horikoshii* TrpB (e.g., UniProt Accession No. O59265), an *R. solanacearum* TrpB (e.g., UniProt Accession No. Q8XXY0), an *R. etli* TrpB (e.g., UniProt Accession No. Q2KE82), an *R. leguminosarum* TrpB (e.g., UniProt Accession No. B5ZV70), an *R. loti* TrpB (e.g., UniProt Accession No. Q98CN7), an *R. meliloti* TrpB (e.g., UniProt Accession No. Q92TC9), an *R. sphaeroides* TrpB (e.g., UniProt Accession No. Q9X4E5), an *R. ferrireducens* TrpB (e.g., UniProt Accession No. Q21XI6), an *R. baltica* TrpB (e.g., UniProt Accession No. Q7UKG9), an *R. palustris* TrpB (e.g., UniProt Accession No. Q6NDN6), an *R. denitrificans* TrpB (e.g., UniProt Accession No. Q161H9), an *R. pomeroyi* TrpB (e.g., UniProt Accession No. Q5LV94), an *R. magnifica* TrpB (e.g., UniProt Accession No. A1AXS9), an *S. agona* TrpB (e.g., UniProt Accession No. B5F4M4), an *S. arizonae* TrpB (e.g., UniProt Accession No. A9MPY7), an *S. choleraesuis* TrpB (e.g., UniProt Accession No. Q57NT3), an *S. dublin* TrpB (e.g., UniProt Accession No. B5FU66), an *S. enteritidis* TrpB (e.g., UniProt Accession No. B5R3P4), an *S. heidelberg* TrpB (e.g., UniProt Accession No. B4TJK8), an *S. newport* TrpB (e.g., UniProt Accession No. B4T6X1), an *S. paratyphi* TrpB (e.g., UniProt Accession No. B5BIC1), an *S. schwarzengrund* TrpB (e.g., UniProt Accession No. B4TX38), an *S. typhi* TrpB (e.g., UniProt Accession No. P0A2K2), an *S. typhimurium* TrpB (e.g., UniProt Accession No. P0A2K1), an *S. proteamaculans* TrpB (e.g., UniProt Accession No. A8GF82), an *S. amazonensis* TrpB (e.g., UniProt Accession No. A1S712), an *S. baltica* TrpB (e.g., UniProt Accession No. A3D630), an *S. denitrificans* TrpB (e.g., UniProt Accession No. Q12LE2), an *S. figidimarina* TrpB (e.g., UniProt Accession No. Q084N8), an *S. halifaxensis* TrpB (e.g., UniProt Accession No. B0TP63), an *S. loihica* TrpB (e.g., UniProt Accession No. A3QF73), an *S. oneidensis* TrpB (e.g., UniProt Accession No. Q8ECV0), an *S. pealeana* TrpB (e.g., UniProt Accession No. A8H2X4), an *S. piezotolerans* TrpB (e.g., UniProt Accession No. B8CLM6), an *S. putrefaciens* TrpB (e.g., UniProt Accession No. A4Y845), an *S. woodyi* TrpB (e.g., UniProt Accession No. B1KK02), an *S. boydii* TrpB (e.g., UniProt Accession No. B2U0F2), an *S. dysenteriae* TrpB (e.g., UniProt Accession No. Q32GS9), an *S. flexneri* TrpB (e.g., UniProt Accession No. P0A880), an *S. fredii* TrpB (e.g., UniProt Accession No. C3MB99), an *S. medicae* TrpB (e.g., UniProt Accession No. A6UEI1), an *S. glossinidius* TrpB (e.g., UniProt Accession No. Q2NT52), an *S. aureus* TrpB (e.g., UniProt Accession No. Q2YXX2), an *S. epidermidis* TrpB (e.g., UniProt Accession No. Q8CPB1), an *S. saprophyticus* TrpB (e.g., UniProt Accession No. Q49XH8), an *S. maltophilia* TrpB (e.g., UniProt Accession No. B2FNZ 1), an *S. pneumoniae* TrpB (e.g., UniProt Accession No. C1C966), an *S. thermophilus* TrpB (e.g., UniProt Accession No. Q5M350), an *S. avermitilis* TrpB (e.g., UniProt Accession No. Q82A82), an *S. coelicolor* TrpB (e.g., UniProt Accession No. O05625), an *S. griseus* TrpB (e.g., UniProt Accession No. B1W0P0), a *T. gammatolerans* TrpB (e.g., UniProt Accession No. C5A1P4), a *T. onnurineus* TrpB (e.g., UniProt Accession No. B6YSU5), a *T. acidophilum* TrpB (e.g., UniProt Accession No. Q9HKD2), a *T. volcanium* TrpB (e.g., UniProt Accession No. Q97A51), a *T. aficanus* TrpB (e.g., UniProt Accession No. B7IHA8), a *T. elongatus* TrpB (e.g., UniProt Accession No. Q8DG49), a *T. denitrificans* TrpB (e.g., UniProt Accession No. Q3 SHL9), a *T. auensis* TrpB (e.g., UniProt Accession No. C4LC89), a *T. erythraeum* TrpB (e.g., UniProt Accession No. Q118P8), a *V. eiseniae* TrpB (e.g., UniProt Accession No. A1WSF1), a *V. okutanii* TrpB (e.g., UniProt Accession No. A5CVH4), a *V. campbellii* TrpB (e.g., UniProt Accession No. A7MRY0), a *V. cholerae* TrpB (e.g., UniProt Accession No. Q9KST6), a *V. fischeri* TrpB (e.g., UniProt Accession No. Q5E623), a *V. metschnikovii* TrpB (e.g., UniProt Accession No. Q9RCE8), a *V. tasmaniensis* TrpB (e.g., UniProt Accession No. B7VGU7), a *V. vulnificus* TrpB (e.g., UniProt Accession No. Q8D8B2), *X. axonopodis* TrpB (e.g., UniProt Accession No. Q8PJ28), *X. campestris* TrpB (e.g., UniProt Accession No. Q4UWD2), *X. oryzae* TrpB (e.g., UniProt Accession No. Q2P0U2), *X. fastidiosa* TrpB (e.g., UniProt Accession No. Q9PDK4), a *Y. enterocolitica* TrpB (e.g., UniProt Accession No. A1JPX6), a *Y. pestis* TrpB (e.g., UniProt Accession No. Q8ZEG9), or a variant thereof.

In some embodiments, the TrpB is recombinantly expressed and optionally isolated and/or purified for carrying out the in vitro tryptophan synthesis. In other embodiments, the TrpB is expressed in whole cells such as bacterial cells, archaeal cells, yeast cells, fungal cells, insect cells, plant cells, or mammalian cells, and these cells are used for carrying out the in vivo tryptophan synthesis. The wild-type or mutated gene can be expressed in a whole cell using an expression vector under the control of an inducible promoter or by means of chromosomal integration under the control of a constitutive promoter. Enzymatic activity can be screened in vivo or in vitro by following product formation by GC or HPLC.

Suitable bacterial host cells include, but are not limited to, BL21 *E. coli*, DE3 strain *E. coli*, *E. coli* M15, DH5α, DH10β, HB101, T7 Express Competent *E. coli* (NEB), *B. subtilis* cells, *Pseudomonas fluorescens* cells, and cyanobacterial cells such as *Chlamydomonas reinhardtii* cells and *Synechococcus elongates* cells. Non-limiting examples of archaeal host cells include *Pyrococcus furiosus*, *Metallosphera sedula*, *Thermococcus litoralis*, *Methanobacterium thermoautotrophicum*, *Methanococcus jannaschii*, *Pyrococcus abyssi*, *Sulfolobus solfataricus*, *Pyrococcus woesei*, *Sulfolobus shibatae*, and variants thereof. Fungal host cells include, but are not limited to, yeast cells from the genera *Saccharomyces* (e.g., *S. cerevisiae*), *Pichia* (*P. Pastoris*), *Kluyveromyces* (e.g., *K. lactis*), *Hansenula* and *Yarrowia*, and filamentous fungal cells from the genera *Aspergillus*, *Trichoderma*, and *Myceliophthora*. Suitable insect host cells include, but are not limited to, Sf9 cells from *Spodoptera frugiperda*, Sf21 cells from *Spodoptera frugiperda*, Hi-Five cells, BTI-TN-5B 1-4 *Trichophusia ni* cells, and Schneider 2 (S2) cells and Schneider 3 (S3) cells from *Drosophila melanogaster*. Non-limiting examples of mammalian host cells include HEK293 cells, HeLa cells, CHO cells, COS cells, Jurkat cells, NS0 hybridoma cells, baby hamster kidney (BHK) cells, MDCK cells, NIH-3T3 fibroblast cells, and any other immortalized cell line derived from a mammalian cell. Non-limiting examples of plant host cells include those from tobacco, tomato, potato, maize, rice, lettuce, and spinach. In general, cells from plants that have short generation times and/or yield reasonable biomass with standard cultivation techniques are preferable.

In certain embodiments, TrpBs inside living cells are provided. As a non-limiting example, bacterial cells (e.g., *E. coli*) can be used as host whole cell catalysts for in vivo tryptophan preparation, although any number of host whole cells may be used, including but not limited to the host cells described herein. In some embodiments, host whole cell catalysts containing TrpBs are found to significantly enhance the total turnover number (TTN) compared to the in vitro reactions using isolated TrpBs.

The expression vector comprising a nucleic acid sequence that encodes a TrpB can be a viral vector, a plasmid, a phage, a phagemid, a cosmid, a fosmid, a bacteriophage (e.g., a bacteriophage P1-derived vector (PAC)), a baculovirus vector, a yeast plasmid, or an artificial chromosome (e.g., bacterial artificial chromosome (BAC), a yeast artificial chromosome (YAC), a mammalian artificial chromosome (MAC), and human artificial chromosome (HAC)). Expression vectors can include chromosomal, non-chromosomal, and synthetic DNA sequences. Equivalent expression vectors to those described herein are known in the art and will be apparent to the ordinarily skilled artisan.

The expression vector can include a nucleic acid sequence encoding a TrpB that is operably linked to a promoter, wherein the promoter comprises a viral, bacterial, archaeal, fungal, insect, plant, or mammalian promoter. In certain embodiments, the promoter is a constitutive promoter. In some embodiments, the promoter is an inducible promoter. In other embodiments, the promoter is a tissue-specific promoter or an environmentally regulated or a developmentally regulated promoter.

In some embodiments, the nucleic acid sequence encodes a TrpB that comprises an amino acid sequence that has about 70% or greater (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) identity to any one of the amino acid sequences set forth herein (e.g., a polypeptide according to SEQ ID NO:3 or SEQ ID NO:4).

In some embodiments, the nucleic acid sequence encodes a TrpB that comprises an amino acid sequence that has about 80% or greater (e.g., about 80%, 81%, 82%, 83%, 84%, 85%, 86%, 87%, 88%, 89%, 90%, 91%, 92%, 93%, 94%, 95%, 96%, 97%, 98%, 99%, or 100%) identity to any of the amino acid sequences set forth herein. In some embodiments, the nucleic acid sequence encodes a TrpB that comprises an amino acid sequence that has about 90% or greater (e.g., about 90%, 91%, 92%, 93%, 94%, 95%, 96%, 97%, 98%, 99%, or 100%) identity to any of the amino acid sequences set forth herein. In some instances, the nucleic acid sequence encodes a TrpB that comprises an amino acid sequence that is about 95%, 96%, 97%, 98%, 99%, or 100% identical to any of the amino acid sequences set forth herein.

In some embodiments, the nucleic acid sequence encodes a TrpB that comprises an amino acid sequence that contains between about 5 and 385 (e.g., about 5-50, 50-100, 100-150, 150-200, 200-250, 250-300, 300-350, or 350-385; or about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, or 385) of the amino acids in any of the amino acid sequences set forth herein (e.g., SEQ ID NO:3 or SEQ ID NO:4). The amino acids may be contiguous, or separated by any number of amino acids.

It is understood that affinity tags may be added to the N- and/or C-terminus of a TrpB expressed using an expression vector to facilitate protein purification. Non-limiting examples of affinity tags include metal binding tags such as His6-tags (SEQ ID NO: 29) and other tags such as glutathione S-transferase (GST).

Non-limiting expression vectors for use in bacterial host cells include pCWori, pET vectors such as pET22 (EMD Millipore), pBR322 (ATCC37017), pQE™ vectors (Qiagen), pBluescript™ vectors (Stratagene), pNH vectors, lambda-ZAP vectors (Stratagene); ptrc99a, pKK223-3, pDR540, pRIT2T (Pharmacia), pRSET, pCR-TOPO vectors, pET vectors, pSyn_1 vectors, pChlamy_1 vectors (Life Technologies, Carlsbad, Calif.), pGEM1 (Promega, Madison, Wis.), and pMAL (New England Biolabs, Ipswich, Mass.). Non-limiting examples of expression vectors for use in eukaryotic host cells include pXT1, pSG5 (Stratagene), pSVK3, pBPV, pMSG, pSVLSV40 (Pharmacia), pcDNA3.3, pcDNA4/TO, pcDNA6/TR, pLenti6/TR, pMT vectors (Life Technologies), pKLAC1 vectors, pKLAC2 vectors (New England Biolabs), pQE™ vectors (Qiagen), BacPak baculoviral vectors, pAdeno-X™ adenoviral vectors (Clontech), and pBABE retroviral vectors. Any other vector may be used as long as it is replicable and viable in the host cell.

A number of compounds according to Formula I, as set forth above, can be prepared according to the methods disclosed herein. In some embodiments, $R^1$ is H. Alternatively, the compounds can contain unbranched or branched β-substituents ($R^1$) of varying length. $R^1$ can be, for example, optionally substituted methyl, optionally substituted ethyl, optionally substituted n-propyl, optionally substituted isopropyl, optionally substituted n-butyl, optionally substituted isobutyl, optionally substituted sec-butyl, optionally substituted tert-butyl, optionally substituted n-pentyl, optionally substituted isopentyl, optionally substituted n-hexyl, optionally substituted branched hexyl, optionally substituted n-heptyl, optionally substituted branched heptyl, optionally substituted n-octyl, and optionally substituted branched octyl. The $R^1$ groups can be substituted with one or more $R^{1a}$ groups as set forth above. In some embodiments, $R^1$ is selected from the group consisting of methyl, ethyl, n-propyl, isopropyl, n-butyl, isobutyl, sec-butyl, and tert-butyl.

In some embodiments, methods are provided for a preparing compound according to Formula II:

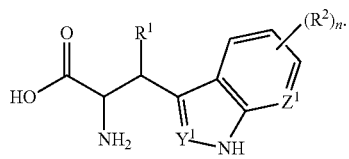

(II)

In some embodiments, $Y^1$ in compounds according to Formula I or Formula II is selected from the group consisting of CH and N. In some embodiments, $Y^1$ is CH, $Z^1$ is CH or N, and $R^1$ is selected from the group consisting of H, methyl, ethyl, n-propyl, isopropyl, n-butyl, isobutyl, sec-butyl, and tert-butyl, each of which is optionally substituted with $R^{1a}$. In some such embodiments, subscript n is 0, 1, or 2. In some embodiments, $Y^1$ is N, $Z^1$ is CH or N, and $R^1$ is selected from the group consisting of H, methyl, ethyl, n-propyl, isopropyl, n-butyl, isobutyl, sec-butyl, and tert-butyl, each of which is optionally substituted with $R^{1a}$. In some such embodiments, subscript n is 0, 1, or 2. In some embodiments, subscript n is 0 or 1. In some embodiments, $Y^1$ is CH, $Z^1$ is CH, and n is 0, 1, or 2.

In some embodiments, each $R^2$ in compounds of Formula I or Formula II is independently selected from the group consisting of —CN, halogen, $C_{1-6}$ alkyl, $C_{1-6}$ alkoxy, and $C_{7-16}$ arylalkyloxy. In some embodiments, each $R^2$ is independently selected from the group consisting of —CN, halogen, and $C_{1-6}$ alkyl. $R^2$ can be, for example, —CN, fluoro, chloro, bromo, methyl, ethyl, n-propyl, isopropyl, n-butyl, isobutyl, sec-butyl, tert-butyl, n-pentyl, isopentyl, n-hexyl, or branched hexyl. $R^2$ can be benzyloxy, methoxy, ethoxy, n-propoxy, isopropoxy, n-butoxy, isobutoxy, sec-butoxy, tert-butoxy, n-pentyloxy, isopentyloxy, n-hexyloxy, or branched hexyloxy. In some embodiments, subscript n is 1, 2, or 3, and $R^2$ is selected from —CN, fluoro, chloro, bromo, methyl, ethyl, n-propyl, isopropyl, n-butyl, isobutyl, sec-butyl, and tert-butyl. In some embodiments, subscript n is 1 or 2, and each $R^2$ is independently selected from fluoro, chloro, bromo, methyl, ethyl, n-propyl, isopropyl, n-butyl, isobutyl, sec-butyl, and tert-butyl. In some embodiments, subscript n is 1 and $R^2$ is selected from —CN, fluoro, chloro, and methyl. In some embodiments, compounds of Formula I or Formula II are substituted with $R^2$ at the indole 4 position.

In some embodiments, the compound has a structure according to Formula IIa:

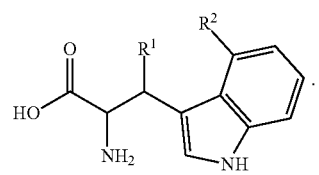

(IIa)

In some embodiments, the compound has a structure according to Formula IIb:

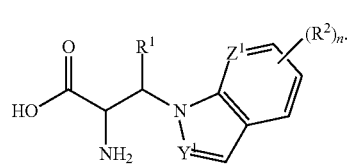

(IIb)

In some embodiments, $R^2$ is a 4-CN moiety.

In some embodiments, methods are provided for preparing compounds according to Formula III:

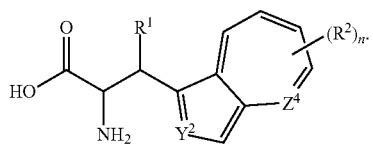

(III)

In some embodiments, $Y^2$ in compounds according to Formula I or Formula III is selected from the group consisting of CH and N. In some embodiments, $Y^2$ is CH, $Z^4$ is CH or N, and $R^1$ is selected from the group consisting of H, methyl, ethyl, n-propyl, isopropyl, n-butyl, isobutyl, sec-butyl, and tert-butyl, each of which is optionally substituted with $R^{1a}$. In some such embodiments, subscript n is 0, 1, or 2. In some embodiments, $Y^2$ is N, $Z^4$ is CH or N, and $R^1$ is selected from the group consisting of H, methyl, ethyl, n-propyl, isopropyl, n-butyl, isobutyl, sec-butyl, and tert-butyl, each of which is optionally substituted with $R^{1a}$. In some such embodiments, subscript n is 0, 1, or 2. In some embodiments, subscript n is 0 or 1. In some embodiments, $Y^2$ is CH, $Z^4$ is CH, and n is 0, 1, or 2.

In some embodiments, each $R^2$ in compounds of Formula III is independently selected from the group consisting of —CN, halogen, $C_{1-6}$ alkyl, $C_{1-6}$ alkoxy, and $C_{7-16}$ arylalkyloxy. In some embodiments, each $R^2$ is independently selected from the group consisting of —CN, halogen, and $C_{1-6}$ alkyl. $R^2$ can be, for example, —CN, fluoro, chloro, bromo, methyl, ethyl, n-propyl, isopropyl, n-butyl, isobutyl, sec-butyl, tert-butyl, n-pentyl, isopentyl, n-hexyl, or branched hexyl. $R^2$ can be benzyloxy, methoxy, ethoxy, n-propoxy, isopropoxy, n-butoxy, isobutoxy, sec-butoxy, tert-butoxy, n-pentyloxy, isopentyloxy, n-hexyloxy, or branched hexyloxy. In some embodiments, subscript n is 1, 2, or 3 in compounds of Formula III, and $R^2$ is selected from —CN, fluoro, chloro, bromo, methyl, ethyl, n-propyl, isopropyl, n-butyl, isobutyl, sec-butyl, and tert-butyl. In some embodiments, subscript n is 1 or 2, and each $R^2$ is independently selected from fluoro, chloro, bromo, methyl, ethyl, n-propyl, isopropyl, n-butyl, isobutyl, sec-butyl, and tert-butyl. In some embodiments, subscript n is 1 and R² is selected from —CN, fluoro, chloro, and methyl.

Compounds of Formula I and Formula II can be prepared using indole substrates including indole substrates according to Formula IV:

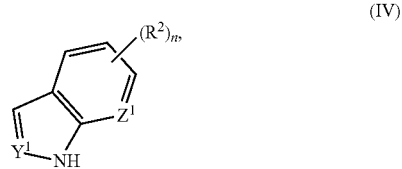

(IV)

wherein Y¹, Z¹, R², n are defined as set forth above. In the context of the present disclosure, the term "indole substrate" refers to indole itself, as well as other fused, bicyclic heterocycles according to Formula IV, e.g., indazoles, pyrazolo[3,4-b]pyridines, and pyrrolo[2,3-b]pyridines.

Compounds of Formula I and Formula III can be prepared using azulene substrates including azulene substrates according to Formula V:

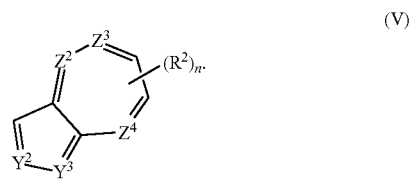

(V)

wherein Y², Y³, Z², Z³, and Z⁴ are defined as set forth above. In the context of the present disclosure, the term "azulene substrate" refers to azulene itself, as well as other fused, bicyclic carbocycles and heterocycles according to Formula V, e.g., cyclohepta[b]pyrroles, cyclohepta[c]pyrazoles, pyrazolo[3,4-b]azepines, pyrazolo[3,4-b][1,4]diazepines, pyrazolo[4,3-c][1,2,5]triazepines, pyrrolo[3,2-c][1,2,5]triazepines, pyrrolo[2,3-b][1,4]diazepines, and pyrrolo[2,3-b]azepanes. Indole substrates according to Formula IV and azulene substrates according to Formula V are commercially available or can be prepared according to known methods, including those described in U.S. Pat. Nos. 7,348,337, 9,334,275, 9,527,812, and WO 2014/056901.

Compounds of Formula I, Formula II, and Formula III can be prepared using serine substrates according to Formula VI,

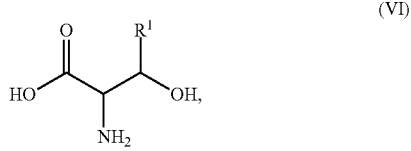

(VI)

wherein R¹ is defined as set forth above. Serine itself as well other β-substituted derivatives are commercially available, or can be synthesized enzymatically using glycine, an aldehyde R¹CHO, and aldolase (e.g., *T. maritima* threonine aldolase) as described, for example, in WO 2018/204691, which is incorporated herein by reference in its entirety.

The TrpB and other enzymes (e.g., aldolases) can be used in purified form, partially purified form, or as whole-cell (e.g., bacterial) catalysts, without purification. Many indole substrates, azulene substrates, and serine substrates can enter *E. coli* cells and interact with the enzymes inside the cells, where the reaction takes place. Thus tryptophan compounds can be made in a process wherein intact or partially permeabilized cells expressing the enzyme catalyst are suspended in buffer and combined with indole or azulene and serine (dissolved in appropriate solvent or in a form of suspension) and allowed to react. The process can also use purified or partially purified protein in place of whole cells. One skilled in the art will be able to identify appropriate processing conditions for a given set of substrates and a given enzyme.

The methods provided herein generally include forming reaction mixtures that comprise an indole substrate or azulene substrate, a serine substrate, and a TrpB as described above. In some embodiments, the method is carried out in vitro. In other embodiments, the TrpB is localized within a whole cell and the method is carried out in vivo. In some embodiments, the TrpB is expressed in a bacterial, archaeal, yeast or fungal host organism. In some embodiments, the method is carried out under anaerobic conditions. In other embodiments, the process is carried out under aerobic conditions.

The TrpBs can be, for example, purified prior to addition to a reaction mixture or secreted by a cell present in the reaction mixture. The reaction mixture can contain a cell lysate including the TrpB as well as other proteins and other cellular materials. Alternatively, a TrpB can catalyze the reaction within a cell expressing the TrpB. Any suitable amount of TrpB can be used in the methods. In general, the reaction mixtures will contain from about 0.01 mol % to about 10 mol % TrpB with respect to the indole substrate, the azulene substrate, or the serine substrate. The reaction mixtures can contain, for example, from about 0.01 mol % to about 0.1 mol % TrpB, or from about 0.1 mol % to about 1 mol % TrpB, or from about 1 mol % to about 10 mol % TrpB. The reaction mixtures can contain from about 0.05 mol % to about 5 mol % TrpB, or from about 0.05 mol % to about 0.5 mol % TrpB. The reaction mixtures can contain about 0.1, 0.2, 0.3, 0.4, 0.5, 0.6, 0.7, 0.8, 0.9, or about 1 mol % TrpB.

The concentration of the indole or azulene and the serine are typically in the range of from about 100 μM to about 1 M. The concentration can be, for example, from about 100 μM to about 1 mM, or about from 1 mM to about 100 mM, or from about 100 mM to about 500 mM, or from about 500 mM to 1 M. The concentration can be from about 500 μM to about 500 mM, 500 μM to about 50 mM, or from about 1 mM to about 50 mM, or from about 15 mM to about 45 mM, or from about 15 mM to about 30 mM. The concentration of indole or azulene and serine can be, for example, about 100, 200, 300, 400, 500, 600, 700, 800, or 900 μM. The concentration of indole or azulene and serine can be about 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, or 500 mM.

Reaction mixtures can contain additional reagents. As non-limiting examples, the reaction mixtures can contain buffers (e.g., M9-N buffer, 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate), cosolvents (e.g., dimethylsulfoxide, dimethylformamide, ethanol, methanol, isopropanol, glycerol, tetrahydrofuran, acetone, acetonitrile, and acetic acid), salts (e.g., NaCl, KCl, CaCl$_2$, and salts of Mn$^{2+}$ and Mg$^{2+}$), denaturants (e.g., urea and guanadinium hydrochloride), detergents (e.g., sodium dodecylsulfate and Triton-X 100), chelators (e.g., ethylene glycol-bis(2-aminoethylether)-N,N, N',N'-tetraacetic acid (EGTA), 2-({2-[Bis(carboxymethyl) amino]ethyl} (carboxymethyl)amino)acetic acid (EDTA), and 1,2-bis(o-aminophenoxy)ethane-N,N,N,N-tetraacetic acid (BAPTA)), sugars (e.g., glucose, sucrose, and the like), and reducing agents (e.g., sodium dithionite, NADPH, dithiothreitol (DTT), 3-mercaptoethanol (BME), and tris(2-carboxyethyl)phosphine (TCEP)). Buffers, cosolvents, salts, denaturants, detergents, chelators, sugars, and reducing agents can be used at any suitable concentration, which can be readily determined by one of skill in the art. In general, buffers, cosolvents, salts, denaturants, detergents, chelators, sugars, and reducing agents, if present, are included in reaction mixtures at concentrations ranging from about 1 µM to about 1 M. For example, a buffer, a cosolvent, a salt, a denaturant, a detergent, a chelator, a sugar, or a reducing agent can be included in a reaction mixture at a concentration of about 1 µM, or about 10 µM, or about 100 µM, or about 1 mM, or about 10 mM, or about 25 mM, or about 50 mM, or about 100 mM, or about 250 mM, or about 500 mM, or about 1 M. In some embodiments, a reducing agent is used in a sub-stoichiometric amount with respect to the olefin substrate and the diazo reagent. Cosolvents, in particular, can be included in the reaction mixtures in amounts ranging from about 1% v/v to about 75% v/v, or higher. A cosolvent can be included in the reaction mixture, for example, in an amount of about 5, 10, 20, 30, 40, or 50% (v/v).

Reactions are conducted under conditions sufficient to catalyze the formation of the amino acid product. The reactions can be conducted at any suitable temperature. In general, the reactions are conducted at a temperature of from about 4° C. to about 80° C. The reactions can be conducted, for example, at about 25° C., or about 37° C., or about 50° C., or about 75° C. In some embodiments, the reactions are conducted at a temperature of from about 20° C. to about 80° C. (e.g., 25-75° C., or 25-50° C., or 25-40° C.). The TrpBs or cells expressing or containing the TrpBs can be heat treated. In some embodiments, heat treatment occurs at a temperature of at least about 75° C. The reactions can be conducted at any suitable pH. In general, the reactions are conducted at a pH of from about 6 to about 10. The reactions can be conducted, for example, at a pH of from about 6.5 to about 9 (e.g., about 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0). The reactions can be conducted for any suitable length of time. In general, the reaction mixtures are incubated under suitable conditions for anywhere between about 1 minute and several hours. The reactions can be conducted, for example, for about 1 minute, or about 5 minutes, or about 10 minutes, or about 30 minutes, or about 1 hour, or about 2 hours, or about 4 hours, or about 8 hours, or about 12 hours, or about 24 hours, or about 48 hours, or about 72 hours. The reactions can be conducted for about 1 to 4 hours (e.g., 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, or 4 hours). Reactions can be conducted under aerobic conditions or anaerobic conditions. Reactions can be conducted under an inert atmosphere, such as a nitrogen atmosphere or argon atmosphere. In some embodiments, a solvent is added to the reaction mixture. In some embodiments, the solvent forms a second phase, and the indole addition to the amino-acrylate intermediate occurs in the aqueous phase. In some embodiments, the TrpB is located in the aqueous layer whereas the substrates and/or products occur in an organic layer. Other reaction conditions may be employed in the methods, depending on the identity of a particular TrpB, indole, azulene, or serine.

Reactions can be conducted in vivo with intact cells expressing an engineered TrpB as described herein. The in vivo reactions can be conducted with any of the host cells used for expression of the enzymes. A suspension of cells can be formed in a suitable medium supplemented with nutrients (such as mineral micronutrients, glucose and other fuel sources, and the like). Product yields from reactions in vivo can be controlled, in part, by controlling the cell density in the reaction mixtures. Cellular suspensions exhibiting optical densities ranging from about 0.1 to about 50 at 600 nm can be used for the amino acid-forming reactions. Other densities can be useful, depending on the cell type, specific TrpBs, or other factors.

The methods can be assessed in terms of the diastereoselectivity and/or enantioselectivity of indole addition to the amino-acrylate intermediate—that is, the extent to which the reaction produces a particular isomer, whether a diastereomer or enantiomer. A perfectly selective reaction produces a single isomer, such that the isomer constitutes 100% of the product. As another non-limiting example, a reaction producing a particular enantiomer constituting 90% of the total product can be said to be 90% enantioselective. A reaction producing a particular diastereomer constituting 30% of the total product, meanwhile, can be said to be 30% diastereoselective.

In general, the methods include reactions that are from about 1% to about 99% diastereoselective. The reactions are from about 1% to about 99% enantioselective. The reaction can be, for example, from about 10% to about 90% diastereoselective, or from about 20% to about 80% diastereoselective, or from about 40% to about 60% diastereoselective, or from about 1% to about 25% diastereoselective, or from about 25% to about 50% diastereoselective, or from about 50% to about 75% diastereoselective. The reaction can be about 10%, 15%, 20%, 25%, 30%, 35%, 40%, 45%, 50%, 55%, 60%, 65%, 70%, 75%, 80%, 85%, 90%, or about 95% diastereoselective. The reaction can be from about 10% to about 90% enantioselective, from about 20% to about 80% enantioselective, or from about 40% to about 60% enantioselective, or from about 1% to about 25% enantioselective, or from about 25% to about 50% enantioselective, or from about 50% to about 75% enantioselective. The reaction can be about 10%, 15%, 20%, 25%, 30%, 35%, 40%, 45%, 50%, 55%, 60%, 65%, 70%, 75%, 80%, 85%, 90%, or about 95% enantioselective. Accordingly some embodiments provide methods wherein the reaction is at least 30% to at least 90% diastereoselective. In some embodiments, the reaction is at least 30% to at least 90% enantioselective. Preferably, the reaction is at least 80% (e.g., at least about 80%, 81%, 82%, 83%, 84%, 85%, 86%, 87%, 88%, 89%, 90%, 91%, 92%, 93%, 94%, 95%, 96%, 97%, 98%, 99%, or 100%) enantioselective. More preferably, the reaction is at least 90% (e.g., at least about 90%, 91%, 92%, 93%, 94%, 95%, 96%, 97%, 98%, 99%, or 100%) enantioselective.

III. EXAMPLES

Example 1. TrpB Engineering for Improved Synthesis of Tryptophan Variants

General Experimental Methods.

Chemicals and reagents were purchased from commercial sources and used without further purification. The proton NMR spectrum was recorded on a Bruker 400 MHz (100 MHz) spectrometer equipped with a cryogenic probe. Proton chemical shifts are reported in ppm (δ) relative to tetramethylsilane and calibrated using the residual solvent resonance (DMSO, δ 2.50 ppm). The NMR spectrum was recorded at ambient temperature (about 25° C.). Preparative reversed-phase chromatography was performed on a Biotage Isolera One purification system, using C18 silica as the stationary phase, with CH3OH as the strong solvent and H2O (0.1% HCl by weight) as the weak solvent. Liquid chromatography/mass spectrometry (LCMS) was performed on an Agilent 1290 UPLC-LCMS equipped with a C-18 silica column (1.8 μm, 2.1×50 mm) using $CH_3CN/H_2O$ (0.1% acetic acid by volume): 5% to 95% $CH_3CN$ over 4 min; 1 mL/min. The optical purity of the products was determined by derivatization with N-(5-fluoro-2,4-dinitrophenyl)alanamide (FDNP-alanamide)[22] as described below.

Cloning, Expression, and Purification of TmTrpB Variants.

TmTrpB (UNIPROT ID P50909) was previously cloned into pET22(b)+ between the NdeI and XhoI sites with a 6× C-terminal His-tag (SEQ ID NO: 29).[17] This study used the previously described variant Tm2F316 as the parent for subsequent evolution. All variants were expressed in BL21 (DE3) E. cloni® Express cells. Cultures were started from single colonies in 5 mL Terrific Broth supplemented with 100 μg/mL ampicillin (TBamp) and incubated overnight at 37° C. and 230 rpm. For expression, 2.5 mL of overnight culture were used to inoculate 250 mL TBamp in a 1-L flask, which was incubated at 37° C. and 250 rpm for three hours to reach OD600 0.6 to 0.8. Cultures were chilled on ice for 20 minutes and expression was induced with a final concentration of 1 mM isopropyl β-D-thiogalactopyranoside (IPTG). Expression proceeded overnight (approximately 20 hours) at 25° C. and 250 rpm. Cells were harvested by centrifugation at 5,000 g for five minutes at 4° C. and stored at −20° C.

Thawed cell pellets were resuspended in 9 mL of lysis buffer containing 50 mM potassium phosphate buffer, pH 8.0 (KPi buffer) with 1 mg/mL hen egg white lysozyme (HEWL), 200 μM PLP, 2 mM MgCl2, 0.02 mg/mL DNase I. Pellets were vortexed until completely resuspended, and then cells were lysed with BugBuster® according to manufacturer's recommendations. Lysates were then heat treated at 75° C. for 10 minutes. The lysate was clarified by centrifugation for 15 minutes at 15,000 g and 4° C. and the supernatant collected. Purification was performed with an AKTA purifier FPLC system (GE Healthcare) and a 1-mL Ni-NTA column. Protein was eluted by applying a linear gradient of 100 mM to 500 mM imidazole in 25 mM KPi buffer and 100 mM NaCl. Fractions containing purified protein were dialyzed into 50 mM KPi buffer, flash frozen in liquid nitrogen, and stored at −80° C. Protein concentrations were determined using the Bio-Rad Quick Start™ Bradford Protein Assay.

Construction of Random Mutagenesis Libraries.

Random mutagenesis libraries were generated from the gene encoding Tm2F3 by adding 200 to 400 μM MnCl2 to a Taq PCR reaction as reported previously.[16,23] PCR fragments were treated with DpnI for two hours at 37° C. and purified by gel extraction. The purified library was then cloned into an empty pET22(b)+ vector via Gibson assembly and transformed into BL21(DE3) E. cloni® Express cells.[24]

```
Forward primer (NdeI)
                                    SEQ ID NO: 27
GAAATAATTTTGTTTAACTTTAAGAAGGAGATATACATATG Reverse primer (XhoI)
                                    SEQ ID NO: 28
GCCGGATCTCAGTGGTGGTGGTGGTGGTGCTCGAG
```

Construction of Recombination Libraries.

Recombination libraries used primers with a degenerate codon to cause a 50/50 amplification of mutant and wild-type residues at a given site (E30G, I184F, G228S). PCR with Phusion® Polymerase (NEB) produced four fragments of the Tm2F3 gene (NdeI to E30, E30 to 1184, 1184 to G228, G228 to XhoI). Fragments were treated with DpnI for two hours at 37° C. and purified by gel extraction. The fragments were assembled by PCR with flanking primers that correspond to the NdeI and XhoI sites of the pET-22(b)+ vector. The assembled gene was then cloned into an empty pET22(b)+ vector via Gibson assembly and transformed into BL21(DE3) E. cloni® Express cells.[24]

Construction of Site-Saturation Libraries.

Site saturation libraries were generated using NEB Q5® site directed mutagenesis kit per manufacturer's instructions using Tm9D8 as the parent. Primers were designed using NEBaseChanger® software and incorporated the degenerate codons NDT (encoding for Ile, Asn, Ser, Gly, Asp, Val, Arg, His, Leu, Phe, Tyr, and Cys), VHG (encoding for Met, Thr, Lys, Glu, Ala, Val, Gln, Pro, and Leu), and TGG (Trp) at the residue of interest. Primers were mixed as reported previously.[25] Following PCR, samples were treated with KLD Enzyme Mix for five minutes, and transformed into BL21 (DE3) E. cloni® Express cells.

Library Expression and Screening.

BL21(DE3) E. cloni® cells carrying variant plasmids were cultured in 96-well deep-well plates along with parent and negative controls as described previously.[16,23] Overnight cultures were grown by inoculating 300 μL TBamp with a single colony followed by incubation at 37° C. and 250 rpm with 80% humidity. The following day 20 μL of the overnight culture were added to 630 μL TBamp and incubated at 37° C. and 250 rpm with 80% humidity for 3 hours. Cells were then chilled on ice for 20 minutes and induced by addition of IPTG (final concentration 1 mM) followed by incubation at 25° C. and 250 rpm overnight (approximately 20 hours). Cells were harvested by centrifugation at 5,000 g for 5 minutes and the supernatant decanted before storage at −20 OC. Cell plates were thawed and resuspended in 300 μL/well 50 mM KPi buffer with 1 mg/mL HEWL, 200 μM PLP, 2 mM MgCl2, and 0.02 mg/mL DNase. Cells were lysed by a 30-minute incubation at 37° C. and heat treatment in a 75° C. water bath for 30 minutes (recombination and site saturation) to 180 minutes (random mutagenesis). Lysate was clarified by centrifugation at 5,000 g for 10 minutes.

Random Mutagenesis Screen.

Reactions were performed in a UV-treated 96-well assay plate with a total volume of 200 μL/well comprised of 40 μL heat-treated lysate, 5 μM 4-cyanoindole, and 50 μM serine with 5% (v/v) DMSO in 50 mM KPi buffer. Reactions proceeded in a 75° C. water bath for 24 hours. Plates were centrifuged briefly to collect condensation and assayed by measuring absorption at 350 nm.

Recombination and Site Saturation Screen.

Reactions were performed in 96-well deep-well plates with a total volume of 200 μL/well comprised of 40 μL heat-treated lysate, 5 M 4-cyanoindole, and 50 μM serine with 5% (v/v) DMSO in 50 mM KPi buffer. Reactions were sealed with Teflon sealing mats and incubated in a 75° C. water bath for 24 hours. Plates were briefly chilled on ice and centrifuged to collect condensation. Each well was charged with 500 µL of 1 M aq. HCl and 500 µL of ethyl acetate. The plate was sealed with a Teflon sealing mat followed by vigorous agitation to dissolve all precipitates and partition the product and substrate between the aqueous and organic phases, respectively. The plates were centrifuged for 2 minutes at 5,000 g and then 200 µL of the aqueous phase was transferred to a 96-well UV-treated assay plate. Activity was determined by measuring the absorption at 300 nm.

Calibration for Measuring HPLC Yield.

Using an authentic standard, mixtures of 4-cyanoindole and 4-cyanotryptophan in varied ratios (9:1, 3:1, 1:1, 1:3, and 1:9) were prepared in 1:1 1-M aq. HCl/CH$_3$CN with a total concentration of 1 mM. Each mixture was prepared in duplicate, then analyzed by LCMS. The ratios of the product and substrate peaks at 254 nm and 280 nm (reference 360 nm, bandwidth 100 nm) were correlated to the actual ratios by a linear relationship.

Figure 3:
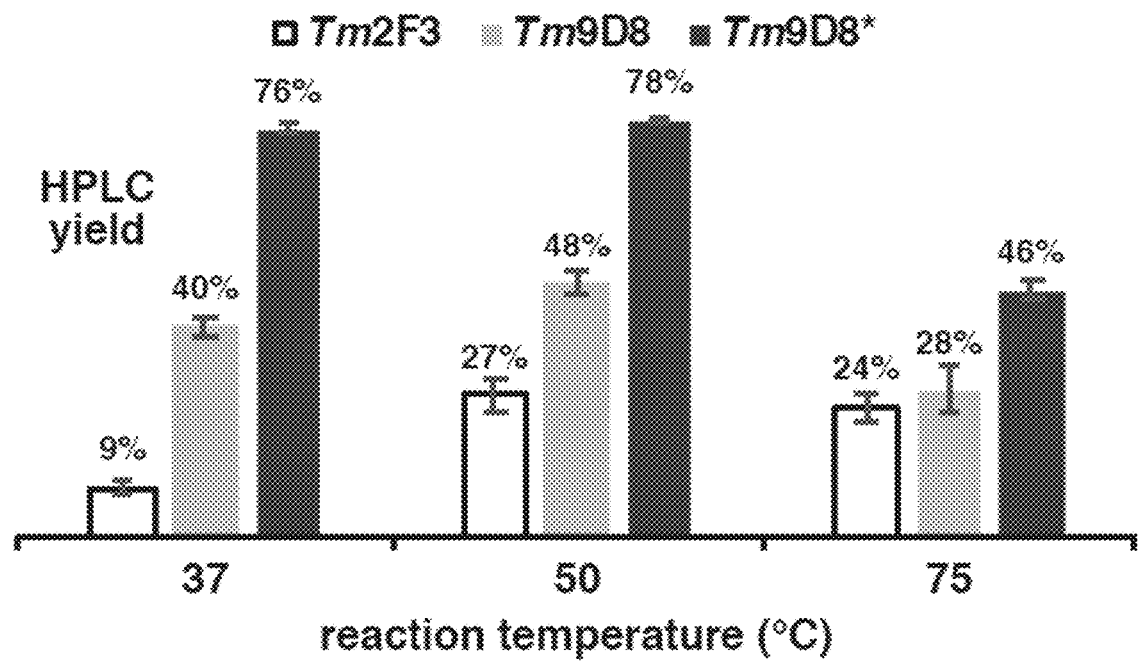
FIG. 3 shows the production of 4-cyanotryptophan at different temperatures from equimolar 4-cyanoindole and serine (maximum of 1000 turnovers).
Figures 4, 5:
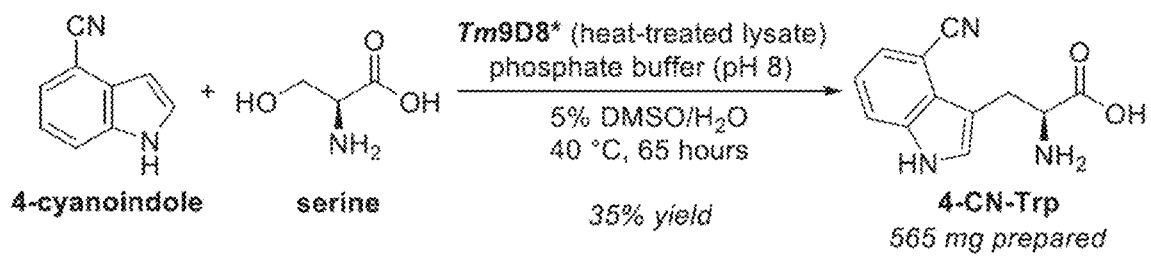
FIG. 4 shows the enzymatic preparation of 4-cyanotryptophan.
FIG. 5 shows the HPLC yield of Trp analogs with TrpB variants. Reactions had 0.02 mol % catalyst (maximum 5000 turnovers) and 1 eq of serine relative to indole substrates. Reactions for Tm2F3 and Tm9D8 were run at 50° C. Reactions for Tm9D8* were run at 37° C. Circles indicate cite of C—C bond formation.

Reactions for FIG. 3 and FIG. 5.

A 2-mL glass HPLC vial was charged with 20 mM nucleophile substrate as 10 µL of a 400-mM solution in DMSO. Next, 20 mM serine and purified enzyme (4 µM or 20 µM) were added as a solution in 190 µL of 50 mM KPi buffer. Reactions were heated at 37° C., 50° C., or 75° C. for 24 hours. The reaction was then diluted with 800 µL of 1:1 1 M aq. HCl/CH3CN and vortexed thoroughly. The reaction mixture was then subjected to centrifugation at >20,000 g for 10 minutes and the supernatant analyzed by HPLC. The identity of the product was confirmed by comparison to an authentic standard. The yield was determined by comparing the integrations of the HPLC peaks corresponding to product and starting material.

Determination of T$_{50}$ Values.

A mastermix of 1 µM purified enzyme was prepared in 50 mM KPi buffer and 95 µL added to 12 PCR tubes. Ten test samples were incubated in a thermocycler for 60 minutes with a temperature gradient from 79° C. to 99° C., while the two control samples were incubated at room temperature. All tubes were centrifuged for three minutes to pellet precipitated enzyme, and then 75 µL of the supernatant was transferred from each tube to a UV-treated 96-well assay plate. Enzyme activity was determined by adding an additional 75 µL of 50 mM KPi buffer containing 1 mM indole and 1 mM serine to each well. Reactions were incubated for 45 min at 50° C. (Tm9D8 and Tm9D8*) or 75° C. (Tm2F3) then briefly centrifuged to collect condensation. Activity was determined by measuring the absorption at 290 nm. Activity was correlated to incubation temperature, and the half-denaturation temperatures (T50) were determined. Measurements were conducted in triplicate.

Determination of Optical Purity.

The optical purity of products was estimated by derivatization with FDNP-alanamide. In a 2-mL vial, a 200 uL reaction was carried out as described above. After 24 hours of incubation at 37° C., 100 µL of 1 M aq. NaHCO$_3$ was added to the reaction, and 125 µL of the reaction mixture (up to 1.1 µmol product) was transferred into two 2-mL vials. FDNP-alanamide (33 µL of a 33-mM solution in acetone, 1.1 µmol) was added to each vial, followed by incubation at 37° C. and 230 rpm. After two hours, the reaction mixture was cooled to room temperature and then diluted with 1:1 CH3CN/1 M aq. HCl (600 µL). The resulting solution was analyzed directly by LCMS. Each amino acid was derivatized with both racemic and enantiopure FDNP-alanamide for comparison. Absolute stereochemistry was inferred by analogy to L-tryptophan. All products were >99% ee.

Increasing Activity with 4-Cyanoindole.

As the starting enzyme, a variant designated Tm2F3 (Table 1) was chosen, which is derived from *T. maritima* TrpB and has seven mutations. This variant was selected because in previous studies it exhibited high activity with other 4-substituted indole substrates.[16] In addition, this variant, like its wild-type progenitor, tolerated high reaction temperatures (up to 75° C.), which accelerated the reaction. In the development of Tm2F3, it was found that activating mutations were distributed throughout the protein sequence without any obvious patterns. Moving forward, global random mutagenesis was performed on the Tm2F3 gene to identify additional beneficial mutations to would be impossible to predict.

TABLE 1

Summary of *T. maritima* TrpB variants

| Designation | Mutations | T$_{50}$ (° C.) |
|---|---|---|
| Tm2F3 | P19G, I69V, K96L, P140L, N167D, L213P, T292S | 91.5 ± 09 |
| Tm9D8 | Tm2F3 + E30G, G228S | 88.2 ± 0.7 |
| Tm9D8* | Tm9D8 + I184F | 92.7 ± 0.2 |

It was observed from test reactions that conversion of 4-cyanoindole to 4-CN-Trp was accompanied by an increase in absorption at 350 nm. This spectral shift allowed us to screen the enzyme library rapidly by running reactions in 96-well plates and then monitoring the change in absorption at 350 nm using a plate reader. After screening 1,760 clones, a new variant Tm9D8 (E30G and G228S), that appeared to exhibit a 2.5-fold increase in the yield of 4-CN-Trp, was identified. Strangely, when Tm9D8 was tested in vials, it was found to be no more active than the parent, Tm2F3 (FIG. 3). It was hypothesized that although the plate and vial reactions were ostensibly conducted at the same temperature (75° C.), the reaction mixtures in the plate may have actually been at lower temperature, due to the inherent difficulties in heating a 96-well plate uniformly. Tm9D8 and Tm2F3 were retested at lower temperatures, and it was found that Tm9D8 was almost 2-fold better at 50° C. and almost five-fold better at 37° C. Notably, Tm9D8 performed better at 37° C. than Tm2F3 did at 75° C. This ability to function at a lower temperature is not only advantageous for process development, but also creates the possibility of synthesizing 4-CN-Trp in vivo.

Previously, introduction of the mutation I184F into Tm2F3 was found to improve the production of 4-CN-Trp.[16] An 8-variant recombination library was therefore constructed in which positions 30, 184, and 228 could either be the wild-type or the mutated residues. Screening this set would reveal if E30G and G228S were both responsible for the first-round improvement and whether I184F was still beneficial in this new variant. It was found that the best variant, Tm9D8*, indeed retained all three mutations, boosting production of 4-CN-Trp to ~76-78% at both 37° C. and 50° C. Libraries in which positions 30, 184, and 228 were separately randomized among all twenty canonical amino acids were also tested; screening showed that glycine and serine were favored at positions 30 and 228, respectively. At position 184, leucine also improved activity compared to the native isoleucine, but rescreening showed this mutation was not as beneficial as phenylalanine. Mutating position 184 to lysine was found to be highly activating, giving 4.5-fold improvement relative to Tm2F3 while producing the N-alkylated product. This supports the hypothesis that residue 184 contributes to the orientations of the indole in the active site. Thus, Tm9D8* was utilized for production of 4-CN-Trp.

In addition, a TmD9D8 variant having an I184K mutation exhibited N-alkylation activity. This variant demonstrated a 5-fold improvement in activity as compared to Tm2F3, providing the N-alkylated product depicted below:

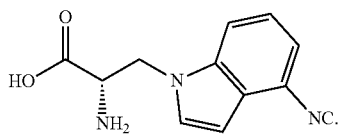

Effect of Evolution on TrpB Activity.

4-Cyanoindole is an especially challenging substrate because its nucleophilicity is attenuated both electronically, due to the electron-withdrawing influence of the cyano group, and sterically, since substituents at the 4-position occlude the site of C—C bond formation. However, the new variant Tm9D8* exhibits improved activity with this substrate and even functions well at 37° C. The high expression level of the protein (~40 mg Tm9D8* per L culture), the availability of the starting materials, and the convenient reaction setup and product recovery make this an effective method for laboratory preparation of 4-CN-Trp.

Mutations discovered to enhance activity with 4-cyanoindole also improved activity for other structurally and electronically distinct substrates, such as 4-bromoindole (1) and disubstituted indoles 4 and S. In all cases, the final variant Tm9D8* gave higher yield at 37° C. than the starting variant Tm2F3 did at 50° C. This general boost in activity at lower temperature is valuable because it not only facilitates process development, but also enables future exploration of substrates that might be unstable in water at elevated temperature. The mutations, however, did not engender general tolerance for 4-substitution, since the enzyme showed negligible activity with 4-nitroindole (2). Surprisingly, activity with 5-nitroindole (3) decreased dramatically, even though Tm2F3 had originally been evolved for activity with this substrate.[16] These data suggest that the mutations have significantly reconfigured the active site compared to Tm2F3, although activity with the native substrate indole remains high for all variants.

Role of Mutations.

The seven mutations in the parent protein Tm2F3 were all previously identified in a TrpB homolog from *Pyrococcus furiosus*, which had been evolved through global random mutagenesis and screening to accept 4-nitroindole as a nucleophilic substrate. Although the *P. furiosus* homolog has only 64% sequence identity to *T. maritima* TrpB,[17] it was found that these seven mutations were activating in both protein scaffolds. This demonstrates that beneficial mutations discovered in one species of enzyme can be used for improved activity in other species. Furthermore, the homologous variants had distinct substrate profiles, with the *T. maritima* variant performing better with 4- or 5-substituted indoles like those shown in FIG. 4.

Figure 6A:
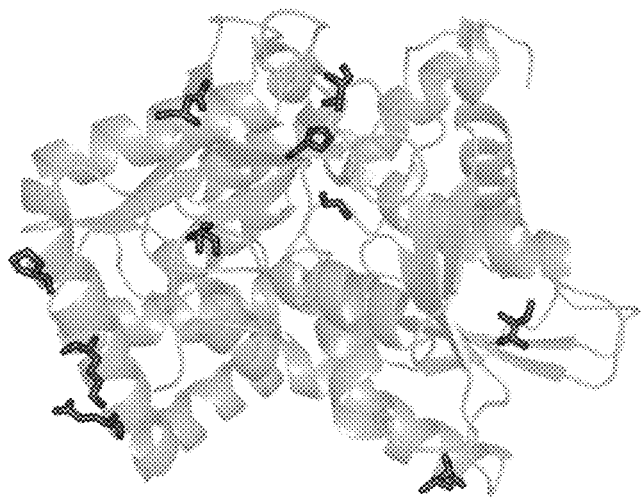
FIG. 6A shows a homology model of the *T. maritima* TrpB active site showing the whole protein structure with mutated sites.

To date, our efforts to solve crystal structures of *T. maritima* TrpB variants have been unsuccessful. A homology model 18-20 based on a 1.65-A crystal structure of *S. typhimurium* TrpB (PDB ID: 4hpx, 58% sequence identity) 21 was construction with the PLP-bound amino-acrylate in the active site. From this model, it is apparent that of the ten mutations in Tm9D8*, only two of them reside in the active site (I184F and G228S), with the other eight scattered throughout the protein structure (FIG. 6A). The precise effects of these eight mutations are uncertain, but previous studies suggested that they stabilize the closed state of the enzyme, 16,17 which is known to promote product formation.

Figure 6B:
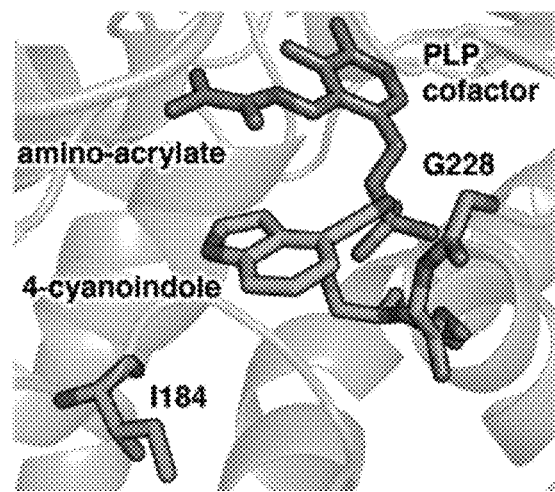
FIG. 6B shows a homology model of the *T. maritima* TrpB active site showing the PLP-bound amino-acrylate with 4-cyanoindole in a reactive binding pose.

The G228S mutation is striking not only because it is an active-site mutation, but also because it is predicted to occur at the beginning of a loop (GGGS (SEQ ID NO: 30)) that binds the phosphate moiety of the PLP cofactor. To speculate on the role of this mutation, 4-cyanoindole was modeled in the putative binding pose necessary for C—C bond formation (FIG. 6B). It is immediately evident that the 4-cyano substituent would point directly toward the phosphate-binding loop and G228 in particular. Thus, it may be that the G228S mutation reorganizes the cofactor-binding site to create space for substituents at the 4-position. A survey of 5,738 TrpB homologs revealed that this GGGS sequence (SEQ ID NO: 30) is almost universally conserved. This variant therefore serves as an example of how mutations of universally conserved residues can benefit reactions with non-natural substrates.

By applying global random mutagenesis to TrpB from *T. maritima*, variants with improved activity for the production of 4-CN-Trp directly from 4-cyanoindole and serine have been developed. Whereas the parent protein struggled to form 4-CN-Trp at 75° C., this new variant exhibits considerable activity even at 37° C., enabling production of 4-CN-Trp under mild conditions. The TrpB-catalyzed reactions occur in aqueous media with readily available starting materials and without the need for protecting groups. Thus, it is believed that the TrpB platform will serve as a powerful tool to develop more efficient and direct routes to ncAAs that minimize the reliance on organic solvents.

Example 2. Large-Scale Production of 4-Cyanotryptophan

The enzyme Tm9D8* was prepared in four 250 mL TBamp expression cultures according to the procedure described above. The cell pellet (16.6 grams) was lysed by resuspension in 66 mL of 50 mM KPi buffer that contained 7.6 mg PLP, 72 mg HEWL, and 6.7 mg DNase. BugBuster® (7.8 mL, 10× concentration) was added, and then the suspension was shaken at 230 RPM and 37° C. for 15 minutes. The suspension was subjected to centrifugation at 4,500 g and 4° C. (5 minutes) and then immersed in a water bath at 75° C. After 30 minutes, the heat-treated lysate was cooled on ice, then subjected to centrifugation at 15,000 g and 4° C. (15 minutes). In a 500-mL Erlenmeyer flask, 4-cyanoindole (1.0 g, 7.0 mmol) and serine (810 mg, 7.7 mmol) were suspended in DMSO (35 mL) and 50 mM KPi buffer (750 mL). Heat-treated lysate (75 mL) was added, then the reaction mixture was incubated at 40° C. and 60 rpm. After 65 hours, the reaction mixture was cooled on ice for 90 minutes. The precipitate was collected by filtration, washed twice with ethyl acetate and twice with water, then dried in vacuo to afford 4-CN-Trp as an off-white solid (493 mg, 31% yield). The mother liquor was further purified on a Biotage Isolera One purification system with a 60-g C-18 silica column to afford an additional 71 mg of product (35% total yield).

Although the final variant requires relatively high catalyst loading (0.1 mol %) to achieve the yields in FIG. 3, its expression level is sufficiently high that enzyme from a 1-L culture can synthesize over 500 mg of 4-CN-Trp at 40° C. (FIG. 4). Since the reaction is performed in aqueous media, most of the product precipitates directly from the reaction mixture and can be purified by simple wash steps. The new variant also retains excellent thermostability (T50 ~90° C.) (Table 1), which allows it to be prepared as heat-treated lysate, facilitating removal of cell debris, and used in the presence of organic solvents, improving solubility of hydrophobic substrates.

Example 3. Study of TrpB Activity/Temperature Profile

The activity of Tm9D8* at 30° C. was tested with a set of 5-substituted indole analogues (5-OH—, 5-OMe-, 5-Br—, 5-CN-indole). Each reaction was prepared by charging a 2 mL glass HPLC vial with 10 µL of a 0.4 M solution of the indole analogue in DMSO, followed by the addition of 190 µL of a solution containing enzyme, serine, and potassium phosphate buffer (50 mM, pH 8.0). This gave final concentrations of 4 µM enzyme (0.02 mol %, 5000 maximum turnovers), 20 mM serine, 20 mM indole analogue, and 5% DMSO in a total volume of 200 µL. The reactions were then incubated in a 30° C. water bath for 6 hours and then worked up with 800 L of a 1:1 1 M aq. HCl/CH3CN mixture and vortexed. The reactions were transferred to microcentrifuge tubes and subjected to centrifugation at >10,000 g for 10 min and analyzed via LCMS. Product yield was calculated by comparing the integrations of the product and nucleophile absorbance peaks at 254 nm.

| Substrate | Rxn Temp (° C.) | Area Product | Area Substrate | Approximate Yield | Max TTN | Approximate TTN |
|---|---|---|---|---|---|---|
| 5-OH-indole | 30 | 3396.2 | 0 | 100% | 5000 | 5000 |
| 5-OMe-indole | 30 | 2591.6 | 1213.4 | 68.1% | 5000 | 3405 |
| 5-Br-indole | 30 | 1615.2 | 1449.2 | 52.7% | 5000 | 2635 |
| 5-CN-indole | 30 | 109.2 | 2968.7 | 3.5% | 5000 | 177 |

Example 4. Preparation of Substituted Tryptophans and Azulenylalanine

TrpB variants were tested with other indole analogs to see how the mutations affected specificity (FIG. 5). To highlight the improved activity at lower temperature, reactions with Tm2F3 and Tm9D8 were screened at 50° C., whereas reactions with Tm9D8* were screened at 37° C. Although Tm2F3 already exhibits good activity (3,250 turnovers at 50° C.) with 4-bromoindole (1), the activity is improved in the later variants, with Tm9D8* performing a similar number of turnovers (3,750), but at lower temperature (37° C.). All variants, however, exhibited negligible activity with 4-nitroindole (2), suggesting that the active site is highly sensitive to the geometry of substituents at the 4-position.

Previously, *T. maritima* TrpB variants had excelled in reactions with 5-substituted indoles.[16,17] However, 5-nitroindole (3) exhibited significantly inferior results with the later variants compared to Tm2F3. The later variants, however, exhibited significant improvements with 5,7-disubstituted substrates, providing almost quantitative conversion of 4 to product, even at 37° C. With substrate 5, the activity is almost an order of magnitude improved from the starting variant.

Initial activity of evolved TrpB enzymes toward azulene was detected by reacting 40 M enzyme with 10 mM azulene and 10 mM serine for a maximum total turnover number of 250. The reactions were set up by charging a 2 mL glass HPLC vial with 10 µL of a 0.2 M solution of the azulene in DMSO, followed by the addition of 190 µL of a solution containing enzyme, serine, and potassium phosphate buffer (50 mM, pH 8.0). The reactions were incubated at either 75° C. or 37° C. for 24 hours. Yield was calculated based on the integration of the AzAla absorbance peak at 254 nm as detected by LC and the area of their extracted mass peaks as detected by MS. While nearly all enzyme performed the reaction with what appeared to be >50% yield (the only exception being Pf0A9 E104G), the best enzyme was identified to be Tm9D8* at 37° C., converting roughly 75% of the azulene to AzAla (see table), corresponding to ~180 TTN.

| Enzyme | Rxn Temp (° C.) | Expected mass (ionized) | RT Product | Area Product | RT Extracted Mass | Area Extracted Mass |
|---|---|---|---|---|---|---|
| PfTrpB 2B9 | 75 | 216 | 0.85 | 6471.65 | 0.86 | 10384676.00 |
| Pf7E6 | 75 | 216 | 0.84 | 5207.93 | 0.86 | 8699469.00 |
| pf0A9 E104G | 75 | 216 | 0.85 | 58.54 | 0.87 | 110092.22 |
| Tm9D8 | 75 | 216 | 0.84 | 5966.23 | 0.86 | 10727975.00 |
| Tm9D8* | 75 | 216 | 0.84 | 6242.00 | 0.86 | 11016502.00 |
| Tm9D8* | 37 | 216 | 0.83 | 7247.31 | 0.86 | 13535750.00 |

Example 5. Preparative Scale Synthesis and Characterization of AzAla

To confirm that AzAla was indeed the product, the reaction was scaled up to 100 µmol in a volume of 10 mL. Tm9D8* enzyme from a 50 mL expression (1.2 g *E. coli* pellet) was used as heat-treated lysate, and added to a solution of 10 mM azulene, 10 mM serine, 5% DMSO. The reaction was allowed to proceed in a 37° C. water bath for 72 hours and then was frozen and lyophilized. Once dry, toluene was added to the material and heated at 75° C. for one minute to remove excess DMSO and then was decanted off. The mixture was resuspended in 1:1 1 M aq. HCl/CH3CN until solubilized (~15 mL). Organic solvent was removed in vacuo and the aqueous solution was then filtered prior to loading onto a C-18 silica column for reversed-phase chromatographic separation via a Biotage Isolera One purification system. The column was washed with $H_2O$ (0.1% aq. HCl) and 1% MeOH for 3 column volumes (CV), 10% MeOH for 5 CV, followed by a linear gradient from 20%-40% MeOH over 15 CV. Residual material was washed off the column with 100% MeOH for 3 CV. AzAla eluted during the linear gradient and was collected and concentrated in vacuo. AzAla-HCl was the resuspended in pure water and transferred to a tared vial and lyophilized overnight. AzAla-HCl was obtained as a deep blue powder; 10.3 mg, 40% yield. The $^1$H NMR spectrum was taken by resuspending 2.7 mg in pure D20 and referenced to the residual solvent peak (4.790 ppm): $^1$H NMR (400 MHz, deuterium oxide) δ 8.42 (dd, J=9.6, 7.7 Hz, 2H), 7.91-7.81 (m, 1H), 7.72 (t, J=9.9 Hz, 1H), 7.43 (d, J=3.9 Hz, 1H), 7.28 (q, J=10.1 Hz, 2H), 4.33 (dd, J=7.4, 5.6 Hz, 1H), 3.79 (dd, J=15.2, 5.6 Hz, 1H), 3.68 (dd, J=15.2, 7.4 Hz, 1H). High-resolution mass spectrometry was performed on an Agilent

IV. REFERENCES (1) Smith, et al. "Top 200 Pharmaceutical Products by Retail Sales in 2016." Poster.
(2) Ager, D. J. "Synthesis of Unnatural/Nonproteinogenic α-Amino Acids." In *Amino Acids, Peptides and Proteins in Organic Chemistry: Origins and Synthesis of Amino Acid*; Hughes, A. B., Ed.; Wiley Online Library, 2010; Vol. 1, pp 495-526.
(3) Brittain, et al. *Org. Biomol. Chem.* 2017, 16 (1), 10-20.
(4) Arnold, et al. *J. Am. Chem. Soc.* 1985, 107, 7105-7109.
(5) Arnold et al *J. Am. Chem. Soc.* 1987, 109 (15), 4649-4659.
(6) Arnold, et al. *J. Am. Chem. Soc.* 1988, 110 (7), 2237-2241.
(7) Tanner. *Angew. Chem. Int. Ed* 1994, 33 (6), 599-619.
(8) Ishikawa. Heterocycles 2012, 85 (12), 2837-2877.
(9) Corr, et al. *Tetrahedron* 2016, 72 (46), 7306-7310.
(10) Smith, et al. *Org. Lett.* 2014, 16 (10), 2622-2625.
(11) Perni, et al. *AMB Express* 2013, 3 (1), 66.
(12) Winn, et al. *Bioorg. Ved (Chem. Lett.* 2008, 18 (16), 4508-4510.
(13) Goss, et al. *Chem. Commun.* 2006, No. 47, 4924-4925.
(14) Lee, et al. *Med. Chem. Let.* 1992, 2 (12), 1563-1564.
(15) Hilaire, et al. *Proc. Nat. Acad Sci.* 2017, 114 (23), 6005-6009.
(16) Romney, et al. *J. Am. Chem. Soc.* 2017, 139 (31), 10769-10776.
(17) Murciano-Calles, et al. *Angew. Chem. Int. Ed.* 2016, 55 (38), 11577-11581.
(18) Biasini, et al. *Nucleic Acids Res.* 2014, 42 (Web Server issue), W252-8.
(19) Arnold, et al. *Bioinformatics* 2006, 22 (2), 195-201.
(20) Benkert, et al. *Bioinformatics* 2011, 27 (3), 343-350.
(21) Niks, et al. *Biochemistry* 2013, 52 (37), 6396-6411.
(22) Bruckner, et al. *J Chromatograph. A* 1991, 555, 81-95.
(23) Buller, et al. *Proc. Nat. Acad Sci.* 2015, 112 (47), 14599-14604.
(24) Gibson, et al. *Nature Methods* 2009, 6 (5), 343-345.
(25) Kille, et al. *ACS Synth. Biol.* 2013, 2 (2), 83-92.

Although the foregoing has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

```
INFORMAL SEQUENCE LISTING

SEQ ID NO: 1 T. maritima TrpB)
MKGYFGPYGGQYVPEILMPALEELEAAYEEIMKDESFWKEFNDLLRDYAG
RPTPLYFARRLSEKYGARIYLKREDLLHTGAHKINNAIGQVLLAKKMGKT
RIIAETGAGQHGVATATAAALFGMECVIYMGEEDTIRQKPNVERMKLLGA
KVVPVKSGSRTLKDAINEALRDWITNLQTTYYVIGSVVGPHPYPIIVRNF
QKVIGEETKKQILEKEGRLPDYIVACVGGGSNAAGIFYPFIDSGVKLIGV
EAGGEGLETGKHAASLLKGKIGYLHGSKTFVLQDDWGQVQVTHSVSAGLD
YSGVGPEHAYWRETGKVLYDAVTDEEALDAFIELSRLEGIIPALESSHAL
AYLKKINIKGKVVVVNLSGRGDKDLESVLNHPYVRERIR SEQ ID NO: 2 (wild type PfTrpB)
MWFGEFGGQYVPETLIEPLKELEKAYKRFKDDEEFNRQLNYYLKTWAGRP
TPLYYAKRLTEKIGGAKIYLKREDLVHGGAHKTNNAIGQALLAKFMGKTR
LIAETGAGQHGVATAMAGALLGMKVDIYMGAEDVERQKMNVFRMKLLGAN
VIPVNSGSRTLKDAINEALRDWVATFEYTHYLIGSVVGPHPYPTIVRDFQ
SVIGREAKAQILEAEGQLPDVIVACVGGGSNAMGIFYPFVNDKKVKLVGV
EAGGKGLESGKHSASLNAGQVGVFHGMLSYFLQDEEGQIKPTHSIAPGLD
YPGVGPEHAYLKKIQRAEYVTVTDEEALKAFHELSRTEGIIPALESAHAV
AYAMKLAKEMSRDEIIIVNLSGRGDKDLDIVLKVSGNV SEQ ID NO: 3 (Tm9D8)
MKGYFGPYGGQYVPEILMGALEELEAAYEGIMKDESFWKEFNDLLRDYAG
RPTPLYFARRLSEKYGARVYLKREDLLHTGAHKINNAIGQVLLAKLMGKT
RIIAETGAGQHGVATATAAALFGMECVIYMGEEDTIRQKLNVERMKLLGA
KVVPVKSGSRTLKDAIDEALRDWITNLQTTYYVIGSVVGPHPYPIIVRNF
QKVIGEETKKQIPEKEGRLPDYIVACVSGGSNAAGIFYPFIDSGVKLIGV
EAGGEGLETGKHAASLLKGKIGYLHGSKTFVLQDDWGQVQVSHSVSAGLD
YSGVGPEHAYWRETGKVLYDAVTDEEALDAFIELSRLEGIIPALESSHAL
AYLKKINIKGKVVVVNLSGRGDKDLESVLNHPYVRERIR SEQ ID NO: 4 (Tm9D8*)
MKGYFGPYGGQYVPEILMGALEELEAAYEGIMKDESFWKEFNDLLRDYAG
RPTPLYFARRLSEKYGARVYLKREDLLHTGAHKINNAIGQVLLAKLMGKT
RIIAETGAGQHGVATATAAALFGMECVIYMGEEDTIRQKLNVERMKLLGA
KVVPVKSGSRTLKDAIDEALRDWITNLQTTYYVFGSVVGPHPYPIIVRNF
QKVIGEETKKQIPEKEGRLPDYIVACVSGGSNAAGIFYPFIDSGVKLIGV
EAGGEGLETGKHAASLLKGKIGYLHGSKTFVLQDDWGQVQVSHSVSAGLD
YSGVGPEHAYWRETGKVLYDAVTDEEALDAFIELSRLEGIIPALESSHAL
AYLKKINIKGKVVVVNLSGRGDKDLESVLNHPYVRERIR SEQ ID NO: 5 A. fulgidus TrpB
MRCWLENLSGGRKMKFGEFGGRFVPEVLIPPLEELEKAYDRFKDDEEFKARLEYYLKSYA
GRPTPLYFAENLSRELGVKIYLKREDLLHGGAHKINNTIGQALLAKFMGKKRVIAETGAG
QHGVATAMAAALLGLEAEIYMGAEDYERQKMNVFRMELLGAKVTAVESGSRTLKDAINEA
```

INFORMAL SEQUENCE LISTING

LRDWVESFEHTHYLIGSVVGPHPFPTIVRDFQAVIGKEARRQIIEAEGGMPDAIIACVGG
GSNAMGIFHPFLNDDVRLIGVEAGGEGIESGRHSASLTAGSKGVLHGMLSYFLQDEEGMM
LDTHSVSAGLDYPGVGPEHAYLKETGRCEYVTVNDEEALRAFKTLSKLEGIIPALESAHA
IAYAMKMAEEMQRDDVLVVNLSGRGDKDMDIVRRLA

SEQ ID NO: 6 E. coli TrpB
MTTLLNPYFGEFGGMYVPQILMPALRQLEEAFVSAQKDPEFQAQFNDLLKNYAGRPTALT
KCQNITAGTNTTLYLKREDLLHGGAHKTNQVLGQALLAKRMGKTEIIAETGAGQHGVASA
LASALLGLKCRIYMGAKDVERQSPNVFRMRLMGAEVIPVHSGSATLKDACNEALRDWSGS
YETAHYMLGTAAGPHPYPTIVREFQRMIGEETKAQILEREGRLPDAVIACVGGGSNAIGM
FADFINETNVGLIGVEPGGHGIETGEHGAPLKHGRVGIYFGMKAPMMQTEDGQIEESYSI
SAGLDFPSVGPQHAYLNSTGRADYVSITDDEALEAFKTLCLHEGIIPALESSHALAHALK
MMRENPDKEQLLVVNLSGRGDKDIFTVHDILKARGEI SEQ ID NO: 7 S. typhimurium TrpB
MTTLLNPYFGEFGGMYVPQILMPALNQLEEAFVSAQKDPEFQAQFADLLKNYAGRPTALT
KCQNITAGTRTTLYLKREDLLHGGAHKTNQVLGQALLAKRMGKSEIIAETGAGQHGVASA
LASALLGLKCRIYMGAKDVERQSPNVFRMRLMGAEVIPVHSGSATLKDACNEALRDWSGS
YETAHYMLGTAAGPHPYPTIVREFQRMIGEETKAQILDKEGRLPDAVIACVGGGSNAIGM
FADFINDTSVGLIGVEPGGHGIETGEHGAPLKHGRVGIYFGMKAPMMQTADGQIEESYSI
SAGLDFPSVGPQHAYLNSIGRADYVSITDDEALEAFKTLCRHEGIIPALESSHALAHALK
MMREQPEKEQLLVVNLSGRGDKDIFTVHDILKARGEI SEQ ID NO: 8 T. naphthophila TrpB
MKGYFGPYGGQYVPEILMPALEELEAAYEGIMKDGSFWREFNDLLRDYAGRPTPLYFARR
LSEKYNARIYLKREDLLHTGAHKINNAIGQVLLAKRMGKTRIIAETGAGQHGVATATAAA
LFGMECVIYMGEEDTIRQKPNVERMKLLGAKVVPVKSGSRTLKDAINEALRDWITNLQTT
YYVIGSVVGPHPYPIIVRNFQKVIGEETKKQILEKEGRLPDYIVACVGGGSNAAGIFYPF
IDSGVKLIGVEAGGEGLETGKHAASLLKGKIGYLHGSKTFVLQDDWGQVQVTHSVSAGLD
YSGVGPEHAYWRETGKVLYDAVTDEEALDAFIELSRLEGIIPALESSHALAYLKKINIKG
KVVVVNLSGRGDKDLESVLNHPYVRERIG SEQ ID NO: 9 T. petrophila TrpB
MKGYFGPYGGQYVPEILMPALEELEAAYEGIMKDGSFWREFNDLLRDYAGRPTPLYFARR
LSEKYNARIYLKREDLLHTGAHKINNAIGQVLLAKRMGKTRIIAETGAGQHGVATATAAA
LFGMECVIYMGEEDTIRQKPNVERMKLLGAKVVPVKSGSRTLKDAINEALRDWITNLQTT
YYVIGSVVGPHPYPIIVRNFQKVIGEETKKQILEKEGRLPDYIVACVGGGSNAAGIFYPF
IDSGVKLIGVEAGGEGLETGKHAASLLKGKIGYLHGSKTFVLQDDWGQVQVTHSVSAGLD
YSGVGPEHAYWRETGKVLYDAVTDEEALDAFIELSRLEGIIPALESSHALAYLKKINIKG
KVVVVNLSGRGDKDLESVLNHPYVRERIG SEQ ID NO: 10 T. neapolitana TrpB
MKGYFGPYGGQYVPEILMPALEELEAAYESITKDESFWEEFNRLLMDYAGRPTPLYFAER
LSKKYGAKIYLKREDLLHTGAHKINNALGQVLLAKRMGKTRIIAETGAGQHGVATATAAA
LFGMECVIYMGEEDTIRQKPNVERMKLLGAKVVPVKSGSRTLKDAINEALRDWITNLQTT
YYVIGSVVGPHPYPIIVRNFQKVIGEETKRQILEKEGKLPDYILACVGGGSNAAGIFYPF
IDSGVKLIGIEAGGEGLNTGKHAASLLKGKVGYLHGSKTLVLQDEWGQVQITHSVSAGLD
YSGVGPEHAYWKETGKVFYDAVTDEEALDAFLELSRLEGIIPALESSHALAYLRKIDIRG
KTVIVNLSGRGDKDLESVLNHPYIRERIG SEQ ID NO: 11 C. subterraneus TrpB
MKGRFGRFGGQYVPETVMNALIELEREFEEAKKDEKFMEEYRYYLKEYSGRPTPLYYAEN
LTKRLGGAKIYLKREDLNHTGAHKINNVLGQVLLAKRMGKKRIIAETGAGQHGVATATAA
AMFGMECEIFMGEEDIKRQALNVFRMKLLGAKVTAVTSGTRTLKDAVNEAIRDWVTNIET
TFYVIGSVVGPHPYPTMVRDFQRVIGDETKEQILEKEGRLPDYVVACVGGGSNAMGIFYP
FIEDKGVKLVGVEAAGEGIETGKHASAMAKGSVGVLHGMMTYLLQDEEGKILPVHSISAG
LDYPGVGPEHAYLKEIGRAEYVYATDEEALAAFMDLSRTEGIIPALESAHALAYAMKLAK
KLDEDKIIVVNLSGRGDKDVNTVAKVMGVEL SEQ ID NO: 12 C. subterraneus TrpB
MKGRFGRFGGQYVPETVMNALIELEREFEEAKKDEKFMEEYRYYLKEYSGRPTPLYYAEN
LTKRLGGAKIYLKREDLNHTGAHKINNVLGQVLLAKRMGKKRIIAETGAGQHGVATATAA
AMFGMECEIFMGEEDIKRQALNVFRMKLLGAKVTAVTSGTRTLKDAVNEAIRDWVTNIET
TFYVIGSVVGPHPYPTMVRDFQRVIGDETKEQILEKEGRLPDYVVACVGGGSNAMGIFYP
FIEDKGVKLIGVEAAGEGIETGKHASAMAKGSVGVLHGMMTYLLQDEEGKILPVHSISAG
LDYPGVGPEHAYLKEIGRAEYVYATDEEALAAFMDLSRTEGIIPALESAHALAYAMKLAK
KLDEDKIIVVNLSGRGDKDVNTVAKVMGVEL SEQ ID NO: 13 D. tunisiensi TrpB
MKKGYYGQYGGQYVPETLIPALKELEAAYEEYSKDPDFLKEYNGLLADYSGRPTPLYYAD
RFTEYLNGAKIYLKREDLNHTGAHKINNALGQVLLAKRMGKKRIIAETGAGQHGVATATA
ATKFGLECVIYMGAEDIKRQSLNVYKMEMLGAKVVPVYNGSQTLNEAVNEARDWVTNVE
DTHYVIGSVVGPHPYPKIVRDFQRIIGDEAKKQIIEKEGRLPDYIIACVGGGSNAIGIFY
PPVEDQEVKLIGVEAAGKGLETGLHAAALTAGKIGVLHGSKSYVLQDENGQIKLAYSISA
GLDYPGVGPEHSYLRDIKRATYTSVTDEEAIEAFELLTKLEGIIPAFESSHALAYTMKLA
PQLDKNKIIVNLSGRGDKDVDAYRNLNRNK

INFORMAL SEQUENCE LISTING

SEQ ID NO: 14 D. kuznetsovii TrpB
MSLPDERGYFGSFGGRYVPETLMPALEELTAAYQEARRDPSFWQELEYYLQQYVGRPSPL
YFARRLSEHCRGARIYLKREDLNHTGAHKINNTIGQILLARRMGKKRIIAETGAGQHGVA
TATAAALFGMECAVYMGEEDMARQALNVFRMRILGATVVGVAAGSRTLKDAMNEAMRDWV
TNVDTTYYLIGSVAGPHPYPVMVRDFQRVIGVETRRQVQEQTGRLPDVIVACVGGGSNAM
GIFHPFLEDREVKLVGVEAAGCGLETGKHAATLNRGRPGILHGSKSYVLQDEDGQINLAH
SISAGLDYPGVGPEHSYLKETGRVVYTAVTDEEALEAFQLLCRTEGIIPALESAHALAQA
VKMAGEMPQDAIIVVNLSGRGDKDVQTVARALGGEG SEQ ID NO: 15 *P. mobilis* TrpB
MKKAYFGQYGGRYVPETLIPALEELEEAHEKYSKDPDFINEYQGLLKDYCGRPTPLYFAE
RFTEYLNGPKIYLKREDLNHTGAHKINNALGQVLLAKRMNKKRIIAETGAGQHGVATATA
AARFGLECIVYMGAEDIRRQALNVYKMRMLGAKVVPVYSGSQTLKEAINEAIRDWVTNVE
NTHYVIGSVVGPHPYPKIVRDFQRVIGDESKNQILEKEGRLPDYIVACVGGGSNAMGIFY
PFIEDKDVELIGVEAAGKGLETGQHAASLTAGKIGVLHGSKSYVLQDDDGQIQLAYSISA
GLDYPGVGPEHSYLHDEKRAQYVSITDEEALKGFELLTKLEGIIPAFESSHAIAYAMKIA
PSLDKDKIMVINLSGRGDKDVDSYIKLGREALE SEQ ID NO: 16 *A. aeolicus* TrpB
MYNYPDERGYFGPFGGKFVPETLMYALEELEEKYRELKSDPEFQKELDYYLREYAGRPTP
LYFAEKLTKYVGGAKIYLKREDLLHTGAHKINNTIGQCLLTKRMGKKRVIAETGAGQHGV
ATATASALFGLECVVYMGEEDAERQALNVFRMKLLGAKVEIVKSGSRTLKDAINEALRDW
VTNVESTHYVIGSVVGPHPFPMIVRDFQSVIGRETKEQILQKEGRLPDAIVACVGGGSNA
MGIFYPFVEDKGVQLIGVEAGGYGLETGQHAASICGGSVGILHGMKSYFLQDEEGQIQPT
HSISAGLDYPGVGPEHALFHEIKRAKYTTATDEEALEGFKLLARTEGIIPALESAHAVIK
AVEVARELGKDGIVVINLSGRGDKDMAHVMKHLSLEG SEQ ID NO: 17 *S. azorense* TrpB
MKKYTFPDERGYYGQFGGKYLPETLIPALEELEQQYLKIKNDGDFKRQLLYYLTEYAGRP
TPLYFASRLTQVVGGAKIYLKREDLLHTGAHKINNTLGQVLLTKRLGKKRIIAETGAGQH
GVSTATAAALFGLECTIYMGEEDAERQALNVFRMKLLGAKVEIVKSGSRTLKDAVNEALR
DWVTNVRTTHYIIGSALGPHPFPMIVRDFQSVIGEEVKNQILEIEGKLPDVIVACVGGGS
NAIGIFYPFIEDEEVKLVGVEAGGYGLETGMHAASIVGGSVGVLHGMKSYFLQDQWGQIE
TTHSISAGLDYPGVGPEHAYLKESGRATYITATDEEALEGFLLLSRTEGIIPALESSHAV
IKAVEIAKNLDKHQSVVINLSGRGDKDVQSVKNLLDTDKELYERLLNKLKEKYGV SEQ ID NO: 18 *T. pseudethanolicus* TrpB
MSGRFGRFGGQYVPETVMNALIELEREFEKAKEDKDFMEEYRYYLREYSGRPTPLYYAEN
LTKRLGGAKIYLKREDLNHTGAHKINNVLGQILLAKRMNKKRVIAETGAGQHGVATATAA
AMFGMECEIFMGEEDIKRQSLNVFRMKLLGAKVTPVTTGTKTLKDAVNEAIRDWVTNIDN
TFYVIGSVVGPHPYPTMVRDFQRVIGDEAKEQILQKEGRLPDYVIACVGGGSNAMGIFYP
FIEDKEVKLIGVEAAGEGIETGKHAAAMAKGSVGVLHGMMTYLLQDEEGRIMPVYSISAG
LDYPGVGPEHAFLKESNRAQYVYATDEEALAAFMDLSQTEGIIPALESAHALAYAMKLAP
NLTKDNIIIVNLSGRGDKDVNTVAKVLGVEL SEQ ID NO: 19 *T. thermophilus* TrpB
MLTLPDFPLPDARGRFGPYGGRYVPETLIPALEELEAAYREAKKDPAFLEELDHYLRQFA
GRPTPLYHAKRLSEYWGGAQVFLKREDLLHTGAHKINNTLGQALLARRMGKRRVIAETGA
GQHGVSVATVAALFGLECVVYMGEEDVRRQALNVFRMKLLGAEVRPVAAGSRTLKDATNE
AIRDWITNVRTTFYILGSVVGPHPYPMMVRDFQSVIGEEVKRQSLELFGRLPDALIAAVG
GGSNAIGLFAPFAYLPEGRPKLIGVEAAGEGLSTGRHAASIGAGKRGVLHGSYMYLLYDH
DGQITPAHSVSAGLDYPGVGPEHSYYADAGVAEYASVTDEEALEGFKLLARLEGIIPALE
SAHAIAYAAKVVPEMDKDQVVVINLSGRGDKDVTEVMRLLGGEL SEQ ID NO: 20 *T. thermophilus* TrpB
MLTLPDFPLPDARGRFGPYGGRYVPETLIPALEELEAAYREAKKDPAFLEELDHYLRQFA
GRPTPLYHAKRLSEYWGGAQVYLKREDLLHTGAHKINNTLGQALLARRMGKRRVIAETGA
GQHGVSVATVAALFGLECVVYMGEEDVRRQALNVFRMKLLGAEVRPVAAGSRTLKDATNE
AIRDWITNVRTTFYILGSVVGPHPYPMMVRDFQSVIGEEVKRQSLELFGRLPDALIAAVG
GGSNAIGLFAPFAYLPEGRPKLIGVEAAGEGLSTGRHAASIGAGKRGVLHGSYMYLLYDH
DGQITPAHSVSAGLDYPGVGPEHSYYADAGVAEYASVTDEEALEGFKLLARLEGIIPALE
SAHAIAYAAKVVPEMDKDQVVVINLSGRGDKDVTEVMRLLGGEL SEQ ID NO: 21 *C. acetobutylicum* TrpB
MNGRFGKFGGQYVPETLMNAINELEVEFNKAINDEKFMMEYKYYLEKYVGRETPLYFAEN
MTKNLGGAKIYLKREDLNHTGSHKLNNALGQVLLAKRMGKKRVIAETGAGQHGVATATAA
ALFGLECEVFMGAEDVERQALNVFRMKILGAKVNSVKSGTNTLKDAINAAMRDWVTNIDN
TYYVIGSVMGPHPYPTIVKDFQKIIGEEARKQILKAEGRLPDYVVACVGGGSNSMGIFYP
FIKDEGVKLIGVEAAGLGIDTPMHAATLTKGSVGIIHGMMTYVLQDEDGQITPAYSVSAG
LDYPGVGPQHSYLKEKERASYEAVTDKEALKAFLYLSEKEGIIPALESSHAVAYAMKLAP
SLSKDEIVIINLSGRGDKDVNTVMKNMEENKNGK SEQ ID NO: 22 *L. pneumophila* TrpB
MIKKELPDEFGHFGPYGGMFVADTLVSALKQLEHAYTKYRNDQDFLSELHTELKDYVGRP
NPLYHAVHLSKKIGGAQIYLKREDLNHTGAHKINNTIGQALLAKRMGKTRVIAETGAGQH
GVATATVAAKFGFQCVVYMGSEDIKRQSSNVYRMKLLGAEVVPVTSGSKTLKDALNEALR
DWVSHVDDTFYIIGTVAGPHPYPQMVRDFQAIIGVEARAQHMEKTGRLPDALVACVGGGS

INFORMAL SEQUENCE LISTING

NAIGLFYPFLNDQSVMIYGVEAGGKGIETGEHSASLIAGKPGVLHGNRTYLLCDEYGQVK
DTHSVSAGLDYPGVGPEHAYLKDTGRVIYKAINDSEALDAFRLLTHTEGIIPALESSHAV
AYAIQLAKTMSKEQSIIVNLSGRGDKDMHTVAAIDGITI

SEQ ID NO: 23 *P. abyssi* TrpB
MWFGKFGGQYVPETLMEPLRELEKAYKRLKNDEEFNRQLDYYLRTWAGRPTPLYYAERLT
KKVGGAKIYLKREDLLHGGAHKTNNAIGQALLAKFMGKTRLIAETGAGQHGVATAMAGAL
LGMKVDIYMGAEDVERQKMNVFRMKLLGANVIPVHTGSKTLKDAINEALRDWVATFEYSH
YLIGSVVGPHPYPIIVRDFQSVIGREAREQILEAEGDLPDVIVACVGGGSNAMGIFYPFV
KDKSVRLIGVEAGGKGIESGKHSASLNAGEIGVFHGMLSYFLQDEEGQIRTTHSIAPGLD
YPGVGPEHAYLKESGRAEYVTVTDEEALRAFHELSRTEGIIPALESAHAVAYAIKLAREM
SRDDVIIVNLSGRGDKDLDIVLKVSGNV SEQ ID NO: 24 *M. jannaschii* TrpB
MSILKKYKDMYPDENGKFGIYGGKFVPETLMPAIAELEEAFKRFWINNEGNFREEFYALL
RDYVGRPTPLYYAERLSEELGCKVYLKREDLAHLGAHKINNALGQALLAKKMGKKRVIAE
TGAGQHGVATAAACAKLGLECIIYMGAKDVERQKLNVFRMELMGAKVIPVFGGSQTLKDA
VNEALRDWTTNVRTTYYLLGSALGPHPYPMMVREFQRVIGKELKEQILEKEGRLPDVIVA
CVGGGSNAIGAFYEFLDDDVELYAVEAGGKGIETGMHGASLCAGEVGVLHGAKIYVKEDE
FGQIEESYSISAGLDYPGVGPELSFLKDEGRIKAVCVTDDEALEAFQLLCRLEGILPALE
SSHALAYAVKLADKLDKDDIMVINLSGRGDKDVQTVAKALGREI SEQ ID NO: 25 *T. kodakarensis* TrpB
MDDMFFGRFGGQFVPETLIEPLKKLERAYKKFKDDPEFNETLEYYLRNWAGRPTPLYYAE
RLSKKLGGAKIYLKREDLLHGGAHKTNNGIGQALLAKFMGKERLIAETGAGQHGVATAMA
GALLGMKVDVYMGAEDVERQKMNVFRMGLLGARVIPVESGSRTLKDAINEALRDWVATFE
YSHYLIGSVVGPYPYPVIVRDFQSVIGREAREQILEAEGTLPDAVVACVGGGSNAMGIFY
PPFVNDRVRLIGVEAGGKGLETGLHAASLNAGELGVFHGMLSYFLQNEEGQITPTHSVSAG
LDYPGVGPEHAYLKDSGRAEYVTVTDEEALRAFHELSRTEGILPALESAHAVAYAMKIAP
EMDKDEIIIVNLSGRGDKDLDIVRRVGNV SEQ ID NO: 26 *M. aeolicus* TrpB
MEYKFGEYGGQYVPEVLMPSLKELEKAYKKYKDDPEFKEELEYYLKQYAGRETPLYFAEN
LTKKMGGAKIYLKREDLLLGGAHKINNSLGQALLAKRIGKTRIIAETGAGEHGLSTAMVG
ALFGLKAKIYMGAVDVERQKLNVYKMRLHGAEVHAVQSGSKTLKDAINEALRDWVETFED
THYIIGSAVGPYPFPSMVRDFQSVIGKEAKKQILEAEGRLPDSIVACVGGGSNSIGIFNE
FKQDKEVKLIGVEAGEGLDTDRHGAAILKGKKGVLHGMLSKFLQDDDGQIAETYSISAG
LDYPGVGPEHAYLDEIKRVEYAGITDVEALDAFSTLSKTEGIIPALESSHAVAHGMKIAK
EMDKDEIIIINLSGRGDKDIHTVMNFIEF

SEQ ID NO: 27
GAAATAATTTTGTTTAACTTTAAGAAGGAGATATACATATG

SEQ ID NO: 28
GCCGGATCTCAGTGGTGGTGGTGGTGGTGCTCGAG

What is claimed is:

1. A method for preparing a compound according to Formula I:

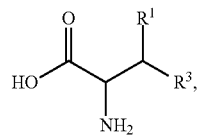

wherein $R^3$ is (A) or (B):

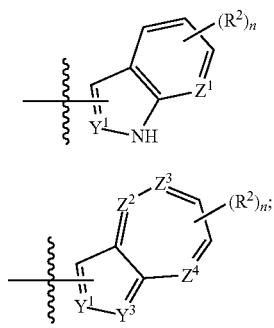

the method comprising:
combining i) an indole substrate or azulene substrate; a serine substrate; and an engineered tryptophan synthase β-subunit (TrpB) selected from the group consisting of a T. maritima TrpB, a P. furiosis TrpB, an A. fulgidus TrpB, a T. naphthophila TrpB, a T. petrophila TrpB, a T. neapolitana TrpB, a C. subterraneus TrpB, a D. tunisiensi TrpB, a D. kuznetsovii TrpB, a P. mobilis TrpB, an A. aeolicus TrpB, an S. azorense TrpB, a T. pseudethanolicus TrpB, a T. thermophilus TrpB, a P. abyssi TrpB, an M. jannaschii TrpB, a T. kodakarensis TrpB, and an M. aeolicus TrpB in a reaction mixture; and maintaining the reaction mixture under conditions sufficient to form the compound according to Formula I;

wherein:
the engineered TrpB comprises a pyridoxal phosphate (PLP) binding loop mutation, a helix 1 mutation, a strand 7-8 mutation, or a combination thereof; and
wherein the PLP binding loop mutation is a mutation of a residue corresponding to any one of residues G227, G228, G229, and S230 in a T. maritima TrpB, the helix 1 mutation is a mutation at a position corresponding to E30 in a T. maritima TrpB, and the strand 7-8 mutation is a mutation at a position corresponding to I184 in a T. maritima TrpB;

$R^1$ is H or $C_{1-8}$ alkyl, which is optionally substituted with one or more $R^{1a}$; each $R^{1a}$ is independently selected from the group consisting of halogen, —OH, —CN, —$N_3$,
—$NO_2$, $C_{1-12}$ alkyl, $C_{6-14}$ aryl, $C_{2-12}$ alkenyl, $C_{1-12}$ alkynyl, $C_{1-12}$ alkoxy,
$C_{1-12}$ thioalkoxy, —$N(R^{1b})_2$, —$C(O)R^{1c}$, —$C(O)N(R^{1b})_2$, —$NR^{1b}C(O)R^{1c}$, and —$OC(O)R^{1c}$;
each $R^{1b}$ is independently selected from the group consisting of H and $C_{1-6}$ alkyl;

each $R^{1c}$ is independently selected from the group consisting of H, —OH, halogen,
$C_{1-6}$ alkyl, $C_{1-6}$ alkoxy;
$Y^1$-$Y^3$ and $Z^1$-$Z^4$ are independently selected from the group consisting of CH, $CR^2$, and N;
each $R^2$ is independently selected from the group consisting of halogen, —OH, —CN, $N_3$,
—$NO_2$, $C_{1-12}$ alkyl, $C_{6-14}$ aryl, $C_{2-12}$ alkenyl, $C_{1-12}$ alkynyl, $C_{1-12}$ alkoxy,
$C_{7-26}$ arylalkyloxy, $C_{1-12}$ thioalkoxy, —$N(R^{2a})_2$, —$C(O)R^{2b}$, —$C(O)N(R^{2a})_2$,
—$NR^{2a}C(O)R^{2b}$, and —$OC(O)R^{2b}$;
each $R^{2a}$ is independently selected from the group consisting of H and $C_{1-6}$ alkyl; each $R^{2b}$ is independently selected from the group consisting of H, —OH, halogen,
$C_{1-6}$ alkyl, $C_{1-6}$ alkoxy; and subscript n is 0, 1, 2, or 3.

2. The method of claim 1, wherein the engineered TrpB contains the PLP binding loop mutation and the helix 1 mutation.

3. The method of claim 1, wherein the engineered TrpB contains the PLP binding loop mutation, the helix 1 mutation, and the strand 7-8 mutation.

4. The method of claim 1, wherein the engineered TrpB further comprises one or more mutations at positions corresponding to P19, I69, K96, P140, N167, L213, and T292 in a T. maritima TrpB.

5. The method of claim 1, wherein the reaction mixture is maintained at a temperature ranging from about 20° C. to about 50° C.

6. The method of claim 1, wherein the compound has a structure according to Formula II:

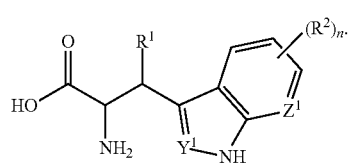

7. The method of claim 1, wherein the compound has a structure according to Formula IIa:

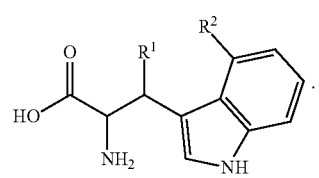

8. The method of claim 1, wherein the compound has a structure according to Formula IIb:

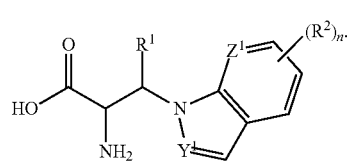

9. The method of claim 1, wherein the compound has a structure according to Formula III:

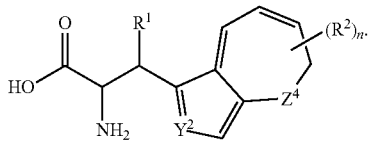

(III)

10. The method of claim 1, wherein each R² is independently selected from the group consisting of —CN, —NO₂, and halogen.

11. The method of claim 1, wherein the compound of Formula I is 4-cyanotryptophan.

12. An engineered tryptophan synthase (β-subunit (TrpB) selected from the group consisting of a *T. maritima* TrpB, a *P. furiosis* TrpB, an *A. fulgidus* TrpB, a *T. naphthophila* TrpB, a *T. petrophila* TrpB, a *T. neapolitana* TrpB, a *C. subterraneus* TrpB, a *D. tunisiensi* TrpB, a *D. kuznetsovii* TrpB, a *P. mobilis* TrpB, an *A. aeolicus* TrpB, an *S. azorense* TrpB, a *T. pseudethanolicus* TrpB, a *T thermophilus* TrpB, a *P. abyssi* TrpB, an *M. jannaschii* TrpB, a *T. kodakarensis* TrpB, and an *M. aeolicus* TrpB, wherein said TrpB comprises a polypeptide having a pyridoxal phosphate (PLP) binding loop mutation, a helix 1 mutation, a strand 7-8 mutation, or a combination thereof, wherein the PLP binding loop mutation is a mutation of a residue corresponding to any one of residues G227, G228, G229, and S230 in a *T. maritima* TrpB, the helix 1 mutation is a mutation at a position corresponding to E30 in a *T. maritima* TrpB, and the strand 7-8 mutation is a mutation at a position corresponding to 1184 in a *T. maritima* TrpB.

13. The engineered TrpB of claim 12, further comprising one or more mutations at positions corresponding to P19, E30, I69, N167, I184, and T292 in a *T. maritima* TrpB.

* * * * *